(12) United States Patent
Fukami et al.

(10) Patent No.: US 6,326,375 B1
(45) Date of Patent: Dec. 4, 2001

(54) SPIRO COMPOUNDS

(75) Inventors: Takehiro Fukami; Akio Kanatani; Akane Ishihara; Yasuyuki Ishii; Toshiyuki Takahashi; Yuji Haga; Toshihiro Sakamoto, all of Tsukuba; Takahiro Itoh, Okazaki, all of (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/640,784

(22) Filed: Aug. 18, 2000

(30) Foreign Application Priority Data

Aug. 20, 1999 (JP) .................................................. 11-233573
May 10, 2000 (JP) .................................................. 12-137692

(51) Int. Cl.$^7$ ........................ A61K 31/438; C07D 491/10
(52) U.S. Cl. ............................ 514/278; 546/17; 546/18; 544/323; 544/336; 514/253; 514/275
(58) Field of Search .................................. 514/278, 275, 514/253; 546/17, 18; 544/323, 336

(56) References Cited

FOREIGN PATENT DOCUMENTS

| 0 615 977 | 9/1994 | (EP) . |
| 99/29696 | 6/1999 | (WO) . |
| 00/27845 | 5/2000 | (WO) . |

*Primary Examiner*—Charanjit S. Aulakh
(74) *Attorney, Agent, or Firm*—Wenderoth, Lind & Ponack, L.L.P.

(57) ABSTRACT

Spiro compounds of the general formula (I):

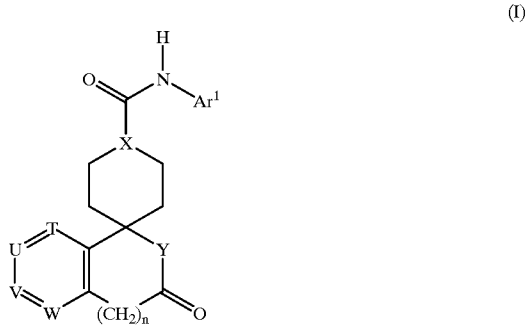

wherein $Ar^1$ represents an optionally substituted aryl or heteroaryl;

n represents 0 or 1;

T, U, V and W each represent a nitrogen atom or an optionally substituted methine group, wherein at least two of which represent said methine group;

X represents nitrogen;

Y represents an optionally substituted imino or oxygen atom, which exhibit neuropeptide Y receptor (NPY) antagonistic activities and are useful as agents for the treatment of various diseases related to NPY, for example, cardiovascular disorders, central nervous system disorders, metobolic diseases and the like.

19 Claims, No Drawings

SPIRO COMPOUNDS

BACKGROUND OF THE INVENTION

1. Field of the Invention

The present invention is useful in medical fields. In more detail, novel Spiro compounds of this invention are useful as neuropeptide Y receptor antagonists and as agents for the treatment of various kinds of cardiovascular disorders, central nervous system disorders, metabolic diseases, and the like.

2. Description of the Prior Art

Neuropeptide Y (hereinafter referred to as NPY), a peptide consisting of 36 amino acids, was first isolated from porcine brain by Tatemoto et al. in 1982 [Nature, 296: 659 (1982)]. NPY is widely distributed in central nervous system and peripheral nervous system and plays various roles as one of the most abundant peptide in the nervous system. That is, NPY acts as an orexigenic substance in the central nervous system and markedly promotes fat accumulation via the mediation of the secretion of various hormones or the action of the nervous system. It is known that the continuous intracerebroventricular administration of NPY induces obesity and insulin resistance based on these actions (International Journal of Obesity, vol.19: 517 (1995); Endocrinology, vol.133: 1753 (1993)). It is also known that NPY has central effects, such as depression, anxiety, schizophrenia, pain, dementia and the like (Drugs, vol. 52, 371(1996). Further, in the periphery, NPY coexists with norepinephrine in sympathetic ending and is involved in the tonicity of the sympathetic nervous system. It is known that peripheral administration of NPY causes vasoconstriction and enhances the activities of other vasoconstrictive substances such as norepinephrine (British Journal of Pharmacology, vol.95: 419 (1988)). It is also reported that NPY could participate in the development of cardiac hypertrophy as a result of the sympathic stimulation (Proceeding National Academic Science USA, Vol. 97, 1595(2000)).

On the other hand, it is reported that NPY is also involved in the secretory function of sexual hormones and growth hormone, sexual behavior and reproductive function, gastrointestinal motility, bronchoconstriction, inflammation and alcohol preference (Life Science, vol. 55, 551(1994); The Journal of Allergy and Immunology, vol. 101, S345(1998); Nature, vol. 396, 366(1998)).

NPY has a variety of pharmacological effects which result from NPY binding to the NPY receptors. Other NPY related peptides, including peptide YY and pancreatic polypeptide also bind to the NPY receptors. It is known that these pharmacological effects are mediated by the action of, at least, five receptor subtypes with or without synergistic interactions. (Trends in Neuroscience, vol.20, 294(1997)).

Y1: It is reported that the central effect mediated by NPY Y1 receptor includes the remarkable orexigenic effect (Endocrinology, vol. 137, 3177(1996); Endocrinology, vol. 141, 1011(2000)). Further, the Y1 receptor is reported to be involved in anxiety and pain (Nature, Vol. 259, 528(1993); Brain Research, vol. 859, 361(2000)). In addition, the pressor effects mediated by the strong action of vasoconstriction in the periphery by NPY is also reported to be mediated by Y1 (FEBS Letters, vol. 362, 192(1995); Nature Medicine, vol. 4, 722(1998)).

Y2: It is known that the inhibitory effect on the release of various neurotransmitters in the sympathetic nerve endings is mediated by the NPY Y2 receptor (British Journal of Pharmacology, vol. 102, 41(1991); Synapse, vol. 2, 299(1988)). In periphery, NPY causes constriction of blood vessel or vas deferens directly or via the control of release of various neurotransmitters (The Journal of Pharmacology and Experimental Therapeutics, vol. 261, 863 (1992); British Journal of Pharmacology, vol. 100, 190 (1990)). In addition, inhibition of lipolysis in adipose tissues is known (Endocrinology, vol. 131, 1970(1992)). Further, the inhibition of ion secretion in the gastrointestinal tract is reported (British Journal of Pharmacology, vol. 101 247(1990)).

On the other hand, the inhibitory effect on the central nervous system functions such as memory and anxiety is also reported (Brain Research, vol. 503, 73(1989); Peptides, vol. 19, 359(1998)).

Y3: It is reported that NPY Y3 receptor is mainly located at brainstem and in the heart and is related to regulation of blood pressure and heart rate (The Journal of Pharmacology and Experimental Therapeutics, vol. 258, 633(1991); Peptides, vol. 11, 545(1990)). Further, it is known that the Y3 receptor is involved in the control of catecholamine secretion in adrenal gland ((The Journal of Pharmacology and Experimental Therapeutics, vol. 244, 468(1988); Life Science, vol. 50, PL7(1992)).

Y4: NPY Y4 receptor has high affinity for pancreatic polypeptide. The related pharmacological effects reported to be mediated by the Y4 receptor include the inhibition of pancreatic secretion and the gastro-intestinal motility (Gastroenterology, vol.85, 1411(1983)). Further, it is reported that NPY enhances the secretion of the sexual hormone in the central nervous system (Endocrinology, vol. 140, 5171(1999)).

Y5: The effect mediated by NPY Y5 receptor includes feeding stimulation and accumulation of fat (Nature, vol. 382, 168(1996)); American Journal of Physiology, vol. 277, R1428(1999)). It is reported that the NPY Y5 receptor also mediates some CNS effects, such as seizure and epilepsy, or pain and the morphine withdrawal symptoms (Natural Medicine, vol. 3, 761(1997); Proceeding Academic Science USA, vol. 96, 13518(1999); The Journal of Pharmacology and Experimental Therapetics, vol. 284, 633(1998)). In the periphery, the Y5 receptor is reported to be involved in diuresis and hypoglicemic effect caused by NPY (British Journal of Pharmacology, vol.120, 1335 (1998); Endocrinology, vol.139, 3018(1998)). NPY is also reported to enhance cardiac hypertrophy as a result of the sympathic accentuation (Proceeding National Academic Science USA, Vol. 97, 1595(2000)).

The effects of NPY occur by binding to the NPY receptors in the central or peripheral nervous system. Therefore, the action of NPY can be prevented by blocking the binding to NPY receptors. Substances antagonize NPY binding to NPY receptors may be useful for the prophylaxis or treatment of various diseases related to NPY, such as cardiovascular disorders (for example hypertension, nephropathy, heart disease, vasospasm), central nervous system disorders (for example bulimia, depression, anxiety, seizure, epilepsy, dementia, pain, alcoholism, drug withdrawal), metabolic diseases (for example obesity, diabetes, hormone abnormality), sexual and reproductive dysfunction, gastrointestinal motility disorder, respiratory disorder, inflammation or glaucoma and the like (Trends in Pharmacological Sciences, 15: 153 (1994); Life Science,. 55, 551(1994); Drugs, vol. 52, 371(1996); The Journal of Allergy and Immunology, vol. 101, S345(1998); Nature, vol. 396, 366 (1998); The Journal of Pharmacology and Experimental Therapeutics, vol. 284, 633(1998); Trends in Pharmacological Science, vol. 20, 104(1999); Proceeding National Academic Science USA, vol. 97, 1595(2000)).

Recently, according to the investigation of the present inventors, it has been found that some kind of NPY receptor antagonist is useful in the prophylaxis or treatment of hypercholesterolemia, hyperlipidemia and arteriosclerosis [International application publication WO99/27965].

SUMMARY OF THE INVENTION

The object of the present invention is to provide novel medicines which exhibit NPY antagonistic activities.

The present inventors have discovered that the compounds of the general formula (I):

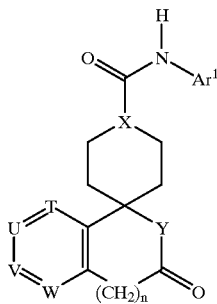

(I)

wherein $Ar^1$ represents aryl or heteroaryl which may be substituted, the substituent being selected from the group consisting of halogen, nitro, lower alkyl, halo (lower)alkyl, hydroxy(lower)alkyl, cyclo(lower)alkyl, lower alkenyl, lower alkoxy, halo(lower)alkoxy, lower alkylthio, carboxyl, lower alkanoyl, lower alkoxycarbonyl, lower alkylene optionally substituted with oxo, and a group represented by formula of —Q—$Ar^2$;

$Ar^2$ represents aryl or heteroaryl which may be substituted, the substituent being selected from the group consisting of halogen, cyano, lower alkyl, halo (lower)alkyl, hydroxy(lower)alkyl, hydroxy, lower alkoxy, halo(lower)alkoxy, lower alkylamino, di-lower alkylamino, lower alkanoyl and aryl;

n represents 0 or 1;

Q represents a single bond or carbonyl;

T, U, V and W represent independently nitrogen atom or methine group which may have a substituent selected from the group consisting of halogen, lower alkyl, hydroxy and lower alkoxy, where at least two of them represent the said methine group;

X represents methine group or nitrogen;

Y represents imino which may be substituted with lower alkyl, or oxygen;

exhibit NPY antagonistic activities and is useful as a therapeutic agent for treatment of various diseases associated with NPY, thereby completing the present invention.

Compounds of the present invention (I) are useful as agents for the treatment of various diseases related to NPY, that is, for example cardiovascular disorders (for example hypertension, nephropathy, heart disease, vasospasm, arteriosclerosis), central nervous system disorders (for example bulimia, depression, anxiety, seizure, epilepsy, dementia, pain, alcoholism, drug withdrawal), metabolic diseases (for example obesity, diabetes, hormone abnormality, hypercholesterolemia, hyperlipidemia), sexual and reproductive dysfunction, gastro-intestinal disorder, respiratory disorder, inflammation, or glaucoma, and the like.

More particularly, compounds of this invention (I) is useful as agents for the treatment of bulimia, obesity, diabetes, and the like.

The present invention refers to compounds of the general formula (I), the salts or esters thereof, and the process for production and use.

In another embodiment, the present invention is related to the intermediate for producing the compound represented by the general formula (I). Specifically, it is related to the compound represented by the general formula (VI-1):

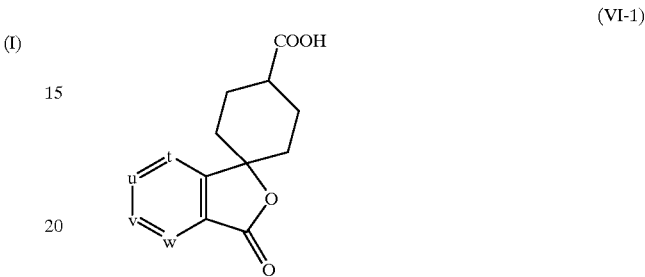

(VI-1)

wherein t, u, v and w represent independently nitrogen atom or methine group which may have a substituent selected from the group consisting of halogen, lower alkyl, lower alkoxy and optionally protected hydroxy, where at least two of them represent the said methine group.

DETAILED DESCRIPTION OF THE INVENTION

The means of terms used in the present specification are defined and more detailed description of this invention is shown in the following.

"Halogen atom" refers to fluorine atom, chlorine atom, bromine atom and iodine atom.

"Lower alkyl" refers to a straight- or branched-chain alkyl group of C1 to C6, for example, methyl, ethyl, propyl, isopropyl, butyl, isobutyl, sec-butyl, tert-butyl, pentyl, isopentyl, hexyl, isohexyl, and the like.

"Halo(lower)alkyl" refers to the aforesaid lower alkyl substituted with 1 or more than 2, preferably 1 to 3 aforesaid halogen atoms identically or differently at the substitutable, arbitrary positions, for example, fluoromethyl, difluoromethyl, trifluoromethyl, 2-fluoroethyl, 1,2-difluoroethyl, chloromethyl, 2-chloroethyl, 1,2-dichloroethyl, bromomethyl, iodomethyl, and the like.

"Hydroxy(lower)alkyl" refers to the aforesaid lower alkyl substituted with 1 or more than 2, preferably 1 or 2 hydroxy groups at the substitutable, arbitrary positions, for example, hydroxymethyl, 2-hydroxyethyl, 1-hydroxy-1-methylethyl, 1,2-dihydroxyethyl, 3-hydroxypropyl, and the like.

"Cyclo(lower)alkyl" refers to a cycloalkyl group of C3 to C6, for example, cyclopropyl, cyclobutyl, cyclopentyl, cyclohexyl, and the like.

"Lower alkenyl" refers to a straight- or branched-chain alkenyl group of C2 to C6, for example, vinyl, 1-propenyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl, 4-pentenyl, and the like.

"Lower alkoxy" refers to a straight- or branched-chain alkoxy group of C1 to C6, for example, methoxy, ethoxy, propoxy, isopropoxy, butoxy, sec-butoxy, isobutoxy, tert-butoxy, pentyloxy, isopentyloxy, hexyloxy, isohexyloxy, and the like.

"Halo(lower)alkoxy" refers to the aforesaid lower alkoxy substituted with 1 or more than 2, preferably 1 to 3 aforesaid halogen atoms identically or differently at the substitutable, arbitrary positions, for example, fluoromethoxy, difluoromethoxy, trifluoromethoxy, 2-fluoroethoxy, 1,2-difluoroethoxy, chloromethoxy, 2-chloroethoxy, 1,2-dichloroethoxy, bromomethoxy, iodomethoxy, and the like.

"Lower alkylthio" refers to a straight- or branched-chain alkylthio group of C1 to C6, for example, methylthio, ethylthio, propylthio, isopropylthio, butylthio, sec-butylthio, isobutylthio, tert-butylthio, pentylthio, isopentylthio, hexylthio, isohexylthio, and the like.

"Lower alkanoyl" refers to an alkanoyl group containing the aforesaid lower alkyl, that is, an alkanoyl group of C2 to C7, for example acetyl, propionyl, butyryl, isobutyryl, valeryl, isovaleryl, pivaloyl, and the like.

"Lower alkoxycarbonyl" refers to an alkoxycarbonyl group containing the aforesaid lower alkoxy, that is, an alkoxycarbonyl group of C2 to C7, for example, methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, and the like.

"Lower alkylene optionally substituted with oxo" refers to a straight- or branched-chain alkylene group of C2 to C6 which may be substituted with 1 or more than 2, preferably 1 oxo group at a substitutable, arbitrary position, for example, ethylene, trimethylene, tetramethylene, pentamethylene, hexamethylene, 1-oxoethylene, 1-oxotrimethylene, 2-oxotrimethylene, 1-oxotetramethylene, 2-oxotetramethylene, and the like.

"Aryl" includes phenyl, naphthyl, and the like.

"Heteroaryl" refers to 5- or 6-membered monocylic heteroaromatic group which contains 1 or more than 2, preferably 1 to 3 hetero atoms identically or differently selected from the group of oxygen atom, nitrogen atom and sulfur atom; or condensed heteroaromatic group, where the aforesaid monocylic heteroaromatic group is condensed with the aforesaid aryl group, or with the identified or different aforesaid monocylic heteroaromatic group each other, for example, pyrrolyl, furyl, thienyl, imidazolyl, pyrazolyl, thiazolyl, isothiazolyl, oxazolyl, isoxazolyl, 1,2,3-triazolyl, 1,2,4-triazolyl, tetrazolyl, oxadiazolyl, 1,2,3-thiadiazolyl, 1,2,4-thiadiazolyl, 1,3,4-thiadiazolyl, pyridyl, pyrazinyl, pyrimidinyl, pyridazinyl, 1,2,4-triazinyl, 1,3,5-triazinyl, indolyl, benzofuranyl, benzothienyl, benzimidazolyl, benzoxazolyl, benzisoxazolyl, benzothiazolyl, benzisothiazolyl, indazolyl, purinyl, quinolyl, isoquinolyl, phthalazyl, naphthylidinyl, quinoxalinyl, quinazolinyl, cinnolinyl, pteridinyl, pyrido[3,2-b]pyridyl, and the like.

"Lower alkylamino" refers to an amino group mono-substituted with the aforesaid lower alkyl, for example, methylamino, ethylamino, propylamino, isopropylamino, butylamino, sec-butylamino, tert-butylamino, and the like.

"Di-lower alkylamino" refers to an amino group di-substituted with identical or different aforesaid lower alkyl, for example, dimethylamino, diethylamino, ethylmethylamino, dipropylamino, methylpropylamino, diisopropylamino, and the like.

The salts of compounds of formula (I) refer to the pharmaceutically acceptable and common salts, for example, base addition salt to carboxyl group when the compound has a carboxyl group, or acid addition salt to amino or basic heterocyclyl when the compound has an amino or basic heterocyclyl group, and the like.

Aforesaid base addition salts include salts with alkali metals (for example sodium, potassium); alkaline earth metals (for example calcium, magnesium); ammonium or organic amines (for example trimethylamine, triethylamine, dicyclohexylamine, ethanolamine, diethanolamine, triethanolamine, procaine, N,N'-dibenzylethylenediamine), and the like.

Aforesaid acid addition salts include salts with inorganic acids (for example hydrochloric acid, sulfuric acid, nitric acid, phosphoric acid, perchloric acid), organic acids (for example maleic acid, fumaric acid, tartaric acid, citric acid, ascorbic acid, trifluoroacetic acid), sulfonic acids (for example methanesulfonic acid, isethionic acid, benzenesulfonic acid, p-toluenesulfonic acid), and the like.

The esters of compounds of formula (I) refer to, for example, the pharmaceutically acceptable, common esters on carboxyl group when the compound has a carboxyl group, for example, esters with lower alkyls (for example methyl, ethyl, propyl, isopropyl, butyl, sec-butyl, tert-butyl, pentyl, isopentyl, neopentyl, cyclopropyl, cyclobutyl, cyclopentyl), aralkyls (for example benzyl, phenethyl), lower alkenyls (for example allyl, 2-butenyl), lower alkoxy (lower) alkyls (for example methoxymethyl, 2-methoxyethyl, 2-ethoxyethyl), lower alkanoyloxy (lower) alkyls (for example acetoxymethyl, pivaloyloxy-methyl, 1-pivaloyloxyethyl), lower alkoxycarbonyl(lower)alkyls (for example methoxycarbonylmethyl, isopropoxycarbonylmethyl), carboxy-(lower)alkyls (for example carboxymethyl), lower alkoxycarbonyloxy-(lower) alkyls (for example 1-(ethoxycarbonyloxy)ethyl, 1-(cyclohexyloxycarbonyloxy)ethyl), carbamoyloxy(lower) alkyls (for example carbamoyloxymethyl), phthalidyl group, (5-substituted-2-oxo-1,3-dioxol-4-yl)methyl (for example (5-methyl-2-oxo-1,3-dioxol-4-yl)methyl), and the like.

"An agent for treatment" refers to a medicament which is employed for the treatment and/or prophylaxis of various diseases.

In order to disclose the aforesaid compounds of the general formula (I) more detailed, the various symbols used in the formula (I) are explained in more detail by the use of preferred embodiments.

$Ar^1$ represents aryl or heteroaryl which may be substituted, the substituent being selected from the group consisting of halogen, nitro, lower alkyl, halo(lower)alkyl, hydroxy(lower)alkyl, cyclo(lower)alkyl, lower alkenyl, lower alkoxy, halo(lower)alkoxy, lower alkylthio, carboxyl, lower alkanoyl, lower alkoxycarbonyl, lower alkylene optionally substituted with oxo, and a group represented by formula of —Q—$Ar^2$.

"Aryl or heteroaryl which may be substituted, the substituent being selected from the group consisting of halogen, nitro, lower alkyl, halo(lower)alkyl, hydroxy(lower)alkyl, cyclo(lower)alkyl, lower alkenyl, lower alkoxy, halo(lower) alkoxy, lower alkylthio, carboxyl, lower alkanoyl, lower alkoxycarbonyl, lower alkylene optionally substituted with oxo, and a group represented by formula of —Q—$Ar^2$"' refers to unsubstituted aforesaid aryl or aforesaid heteroaryl, or the aforesaid aryl or aforesaid heteroaryl which has substituent(s) at the substitutable, arbitrary position(s). The aforesaid substituent can be, identically or differently, one or more than 2, preferably 1 or 2 selected from the group consisting of halogen, nitro, lower alkyl, halo(lower)alkyl, hydroxy(lower)alkyl, cyclo(lower)alkyl, lower alkenyl, lower alkoxy, halo(lower)alkoxy, lower alkylthio, carboxyl, lower alkanoyl, lower alkoxycarbonyl, lower alkylene optionally substituted with oxo, and a group of formula: —Q—$Ar^2$.

Halogen atom as the aforesaid substituent includes fluorine atom, chlorine atom, and the like preferably.

Lower alkyl as the aforesaid substituent includes methyl, ethyl, propyl, isopropyl, and the like preferably.

Halo(lower)alkyl as the aforesaid substituent includes difluoromethyl, trifluoromethyl, and the like preferably.

Hydroxy(lower)alkyl as the aforesaid substituent includes hydroxymethyl, 2-hydroxyethyl, 1-hydroxy-1-methylethyl, and the like preferably.

Cyclo(lower)alkyl as the aforesaid substituent includes cyclopropyl, cyclobutyl, and the like preferably.

Lower alkenyl as the aforesaid substituent includes vinyl, 1-propenyl, 2-methyl-1-propenyl, and the like preferably.

Lower alkoxy as the aforesaid substituent includes methoxy, ethoxy, and the like preferably.

Halo(lower)alkoxy as the aforesaid substituents includes fluoromethoxy, difluoromethoxy, trifluoromethoxy, and the like preferably.

Lower alkylthio as the aforesaid substituent includes methylthio, ethylthio, and the like preferably.

Lower alkanoyl as the aforesaid substituent includes acetyl, propionyl, and the like preferably.

Lower alkoxycarbonyl as the aforesaid substituent includes methoxycarbonyl, ethoxycarbonyl, and the like preferably.

Lower alkylene optionally substituted with oxo as the aforesaid substituent includes 1-oxotetramethylene, and the like preferably.

In a group of formula: —Q—$Ar^2$ as the aforesaid substituent, $Ar^2$ represents aryl or heteroaryl which may be substituted, the substituent being selected from the group consisting of halogen, cyano, lower alkyl, halo(lower)alkyl, hydroxy(lower)alkyl, hydroxy, lower alkoxy, halo(lower) alkoxy, lower alkylamino, di-lower alkylamino, lower alkanoyl and aryl; Q represents a single bond or carbonyl.

"Aryl or heteroaryl which may be substituted, the substituent being selected from the group consisting of halogen, cyano, lower alkyl, halo(lower)alkyl, hydroxy(lower)alkyl, hydroxy, lower alkoxy, halo(lower)alkoxy, lower alkylamino, di-lower alkylamino, lower alkanoyl and aryl" refers to unsubstituted aforesaid aryl or aforesaid heteroaryl, or the aforesaid aryl or aforesaid heteroaryl which has substituent(s) at the substitutable, arbitrary position(s). The aforesaid substituent can be, identically or differently, one or not less than 2, preferably 1 or 2 selected from the group consisting of halogen, cyano, lower alkyl, halo(lower)alkyl, hydroxy(lower)alkyl, hydroxy, lower alkoxy, halo(lower) alkoxy, lower alkylamino, di-lower alkylamino, lower alkanoyl and aryl.

Halogen atom as the aforesaid substituent includes, preferably, fluorine atom, chlorine atom, and the like.

Lower alkyl as the aforesaid substituent includes, preferably, methyl, ethyl, propyl, isopropyl, and the like.

Halo(lower)alkyl as the aforesaid substituent includes, preferably, difluoromethyl, trifluoromethyl, and the like.

Hydroxy(lower)alkyl as the aforesaid substituent includes, preferably, hydroxymethyl, 2-hydroxyethyl, 1-hydroxy-1-methylethyl, and the like.

Lower alkoxy as the aforesaid substituent includes, preferably, methoxy, ethoxy, and the like.

Halo(lower)alkoxy as the aforesaid substituent includes, preferably, fluoromethoxy, difluoromethoxy, trifluoromethoxy, and the like.

Lower alkylamino as the aforesaid substituent includes, preferably, methylamino, ethylamino, and the like.

Di-lower alkylamino as the aforesaid substituent includes, preferably, dimethylamino, diethylamino, and the like.

Lower alkanoyl as the aforesaid substituent includes, preferably, acetyl, propionyl, and the like.

Aryl as the aforesaid substituent includes, preferably, phenyl, and the like.

The substituent(s) of $Ar^2$ include, preferably, halogen, cyano, lower alkyl, halo(lower)alkyl, hydroxy(lower)alkyl, hydroxy, halo(lower)alkoxy, and the like.

Aryl in $Ar^2$ includes, preferably, phenyl, and the like and heteroaryl includes imidazolyl, pyridyl, benzofuranyl, quinolyl, and the like.

Consequently, a group of formula: —Q—$Ar^2$ includes, for example, phenyl, 2-fluorophenyl, 3-fluorophenyl, 4-fluorophenyl, 2,3-difluorophenyl, 2,4-difluorophenyl, 3,5-difluorophenyl, 2-chlorophenyl, 3-chlorophenyl, 4-chlorophenyl, 2-cyanophenyl, 3-cyanophenyl, 4-cyanophenyl, 2-methylphenyl, 3-methylphenyl, 4-methylphenyl, 2-fluoro-5-methylphenyl, 3-fluoromethylphenyl, 2-trifluoromethylphenyl, 3-trifluoromethylphenyl, 4-trifluoromethylphenyl, 2-methoxyphenyl, 3-methoxyphenyl, 4-methoxyphenyl, 3-fluoro-5-methoxyphenyl, 3-fluoromethoxyphenyl, 3-difluoromethoxyphenyl, 3-(2-hydroxyethyl)phenyl, 3-hydroxymethylphenyl, 3-(1-hydroxy-1-methylethyl) phenyl, 3-hydroxyphenyl, 4-hydroxyphenyl, 2-imidazolyl, 1-ethyl-2-imidazolyl, 1,2,4-thiadiazol-5-yl, 1,3,4-thiadiaol-2-yl, 2-pyridyl, 3-pyridyl, 4-pyridyl, 2-ethyl-4-pyridyl, 4-pyrimidinyl, 5-pyrimidinyl, 4-benzo[b]furanyl, 5-benzo[b]furanyl, 7-benzo[b]furanyl, 2-quinolyl, 3-quinolyl, 4-quinolyl, 5-quinolyl, 6-quinolyl, 8-quinolyl, benzoyl, 2-pyridylcarbonyl, and the like, and preferably, phenyl, 2-fluorophenyl, 3-fluorophenyl, 3,5-difluorophenyl, 3-chlorophenyl, 4-chlorophenyl, 3-cyanophenyl, 3-trifluoromethylphenyl, 3-difluoromethoxyphenyl, 3-(2-hydroxyethyl)phenyl, 3-hydroxyphenyl, 4-hydroxyphenyl, 1-ethyl-2-imidazolyl, 2-pyridyl, 7-benzo[b]furanyl, 2-quinolyl, 3-quinolyl, benzoyl, 2-pyridylcarbonyl, and the like.

The substituent of $Ar^1$ includes, preferably, halogen, lower alkyl, halo(lower)alkyl, lower alkenyl, lower alkanoyl, lower alkylene optionally substituted with oxo, and a group of formula: —Q—$Ar^2$, and the like.

Aryl in $Ar^1$ includes, preferably, phenyl, and the like and heteroaryl of $Ar^1$ includes pyrrolyl, imidazolyl, pyrazolyl, thiazolyl, oxazolyl, isoxazolyl, 1,2,3-triazolyl, 1,2,4-thiadiazolyl, pyridyl, pyrazinyl, pyrimidinyl, 1,2,4-triazinyl, benzoxazolyl, benzothiazolyl, quinolyl, pyrido[3,2-b]pyridyl, and the like.

Consequently, $Ar^1$ includes, for example, 3-fluorophenyl, 4-fluorophenyl, 3,4-difluorophenyl, 3-chlorophenyl, 4-chlorophenyl, 3,4-dichlorophenyl, 4-acetylphenyl, 5-oxo-5,6,7,8-tetrahydro-2-naphthyl, 4-acetyl-3-trifluoromethylphenyl, 4-(1-ethyl- 2-imidazolyl)phenyl, 3-(2-pyridyl)phenyl, 3-(4-pyridyl)phenyl, 4-(2-pyridyl) phenyl, 4-(3-pyridyl)phenyl, 4-(2-ethyl-4-pyridyl)phenyl, 4-(4-pyrimidinyl)phenyl, 4-benzoylphenyl, 4-(2-pyridylcarbonyl)phenyl, 1-phenyl-3-pyrrolyl, 1-phenyl-4-imidazolyl, 1-(2-fluorophenyl)-4-imidazolyl, 1-(3-fluorophenyl)-4-imidazolyl, 1-(4-fluorophenyl)-4-imidazolyl, 1-(2,3-difluorophenyl)-4-imidazolyl, 1-(2,4-difluorophenyl)-4-imidazolyl, 1-(3,5-difluorophenyl)-4-imidazolyl, 1-(3-chlorophenyl)-4-imidazolyl, 1-(2-cyanophenyl)-4-imidazolyl, 1-(3-cyanophenyl)-4-imidazolyl, 1-(4-cyanophenyl)-4-imidazolyl, 1-(3-trifluoromethylphenyl)-4-imidazolyl, 1-[3-(2-hydroxyethyl)phenyl]-4-imidazolyl, 1-[3-(1-hydroxy-1-methylethyl)phenyl]-4-imidazolyl, 1-(3-methoxyphenyl)-4-imidazolyl, 1-(2-difluoromethoxyphenyl)-4-imidazolyl, 1-(3-difluoromethoxyphenyl)-4-imidazolyl, 1-(4-difluoromethoxy-phenyl)-4-imidazolyl, 1-(2-pyridyl)-4-imidazolyl, 1-(4-benzo[b]furanyl)-4-imidazolyl, 1-(5-benzo[b]furanyl)-4-imidazolyl, 1-(7-benzo[b]furanyl)-4-imidazolyl, 1-(2-quinolyl)-4-imidazolyl, 1-(3-quinolyl)-4-imidazolyl, 1-(4-quinolyl)-4-imidazolyl, 1-(5-quinolyl)-4-imidazolyl, 1-(6-quinolyl)-4-imidazolyl, 1-(8-quinolyl)-4-imidazolyl, 1-phenyl-3-pyrazolyl, 5-phenyl-3-pyrazolyl, 1-phenyl-4-pyrazolyl, 1-(2-fluorophenyl)-3-pyrazolyl, 5-(2-fluorophenyl)-3-pyrazolyl, 5-(3-fluorophenyl)-3-pyrazolyl, 1-(3-fluorophenyl)-4-pyrazolyl, 1-(4-fluorophenyl)-3-pyrazolyl, 5-(4-fluorophenyl)-3-pyrazolyl, 5-(2-chlorophenyl)-3-pyrazolyl, 5-(3-chlorophenyl)-3-pyrazolyl, 5-(4-chlorophenyl)-3-pyrazolyl, 5-(2-difluoromethoxyphenyl)-3-pyrazolyl, 5-(3-difluoromethoxyphenyl)-3-pyrazolyl, 2-methyl-5-phenyl-3-pyrazolyl, 5-(2-pyridyl)-3-pyrazolyl, 5-(2-quinolyl)-3-pyrazolyl, 5-(3-quinolyl)-3-pyrazolyl, 4-phenyl-2-thiazolyl, 5-phenyl-2-thiazolyl, 5-(3-chlorophenyl)-2-thiazolyl, 5-(4-chlorophenyl)-2-thiazolyl, 5-(4-methoxyphenyl)-2-thiazolyl, 5-(2-pyridyl)-2-thiazolyl, 2-phenyl-4-thiazolyl, 4-phenyl-2-oxazolyl, 5-phenyl-2-oxazolyl, 4-(2-fluoromethoxyphenyl)-2-oxazolyl, 4-(3-fluoromethoxyphenyl)-2-oxazolyl, 5-phenyl-3-isoxazolyl, 3-phenyl-5-isoxazolyl, 3-(2-chlorophenyl)-5-isoxazolyl, 3-(3-chlorophenyl)-5-isoxazolyl, 3-(4-chlorophenyl)-5-isoxazolyl, 3-(2-pyridyl)-5-isoxazolyl, 2-phenyl-1,2,3-triazol-4-yl, 5-phenyl-1,2,4-thiadiazol-3-yl, 5-phenyl-1,3,4-thiadiazol-2-yl, 5-(3-chlorophenyl)-1,3,4-thiadiazol-2-yl, 5-(2-pyridyl)-1,3,4-thiadiazol-2-yl, 5-(2-ethyl-4-pyridyl)-1,3,4-thiadiazol-2-yl, 5-phenyl-2-pyridyl, 6-phenyl-3-pyridyl, 2-phenyl-4-pyridyl, 5-(2-pyridyl)-2-pyridyl, 5-benzoyl-2-pyridyl, 6-benzoyl-3-pyridyl, 5-chloro-2-pyrazinyl, 5-(2-methyl-1-propenyl)-2-pyrazinyl, 5-acetyl-2-pyrazinyl, 5-propionyl-2-pyrazinyl, 5-phenyl-2-pyrazinyl, 5-(3-hydroxyphenyl)-2-pyrazinyl, 5-(4-hydroxyphenyl)-2-pyrazinyl, 5-(1,2,4-thiadiazol-5-yl)-2-pyrazinyl, 5-(1,3,4-thiadiazol-2-yl)-2-pyrazinyl, 5-(2-pyridyl)-2-pyrazinyl, 5-(3-pyridyl)-2-pyrazinyl, 5-(5-pyrimidinyl)-2-pyrazinyl, 5-(3-quinolyl)-2-pyrazinyl, 5-benzoyl-2-pyrazinyl, 5-(2-pyridylcarbonyl)-2-pyrazinyl, 5-acetyl-2-pyrimidinyl, 5-acetyl-3-methyl-2-pyrimidinyl, 4-phenyl-2-pyrimidinyl, 5-phenyl-2-pyrimidinyl, 6-phenyl-4-pyrimidinyl, 2-phenyl-5-pyrimidinyl, 5-(2-fluorophenyl)-2-pyrimidinyl, 5-(3-fluorophenyl)-2-pyrimidinyl, 5-(4-fluorophenyl)-2-pyrimidinyl, 5-(2-chlorophenyl)-2-pyrimidinyl, 5-(3-chlorophenyl)-2-pyrimidinyl, 5-(4-chlorophenyl)-2-pyrimidinyl, 5-(2-methylphenyl)-2-pyrimidinyl, 5-(3-methylphenyl)-2-pyrimidinyl, 5-(2-fluoromethylphenyl)-2-pyrimidinyl, 5-(3-fluoromethylphenyl)-2-pyrimidinyl, 5-(2-trifluoromethylphenyl)-2-pyrimidinyl, 5-(3-trifluoromethylphenyl)-2-pyrimidinyl, 5-(4-trifluoromethylphenyl)-2-pyrimidinyl, 5-(2-hydroxymethylphenyl)-2-pyrimidinyl, 5-(3-hydroxymethylphenyl)-2-pyrimidinyl, 5-(2-hydroxyphenyl)-2-pyrimidinyl, 5-(3-hydroxyphenyl)-2-pyrimidinyl, 5-(2-methoxyphenyl)-2-pyrimidinyl, 5-(3-methoxyphenyl)-2-pyrimidinyl, 5-(4-methoxyphenyl)-2-pyrimidinyl, 5-(2-fluoromethoxyphenyl)-2-pyrimidinyl, 5-(3-fluoromethoxyphenyl)-2-pyrimidinyl, 5-(2-fluoro-5-methylphenyl)-2-pyrimidinyl, 5-(3-fluoro-5-methoxyphenyl)-2-pyrimidinyl, 6-phenyl-3-pyridazinyl, 6-phenyl-1,2,4-triazin-3-yl, 5-chloro-2-benzoxazolyl, 5-fluoro-2-benzothiazolyl, 4-methyl-2-benzothiazolyl, 2-methyl-5-benzothiazolyl, 4-methoxy-2-benzothiazolyl, 3-quinolyl, 6-quinolyl, 7-methyl-2-quinolyl, 2-methyl-6-quinolyl, 6-chloro-2-quinoxalinyl, pyrido[3,2-b]pyridin-2-yl, 7-chloropyrido[3,2-b]pyridin-2-yl, 7-methylpyrido[3,2-b]pyridin-2-yl, 7-trifluoromethylpyrido[3,2-b]pyridin-2-yl, 7-difluoromethoxypyrido[3,2-b]pyridin-2-yl, 7-acetylpyrido[3,2-b]pyridin-2-yl, and the like, preferably 3,4-dichlorophenyl, 4-acetylphenyl, 5-oxo-5,6,7,8-tetrahydro-2-naphthyl, 4-acetyl-3-trifluoromethylphenyl, 4-(1-ethyl-2-imidazolyl)phenyl, 4-benzoylphenyl, 4-(2-pyridylcarbonyl)phenyl, 1-phenyl-3-pyrrolyl, 1-phenyl-4-imidazolyl, 1-(2-fluorophenyl)-4-imidazolyl, 1-(3,5-difluorophenyl)-4-imidazolyl, 1-(3-chlorophenyl)-4-imidazolyl, 1-(3-cyanophenyl)-4-imidazolyl, 1-[3-(2-hydroxyethyl)phenyl]-4-imidazolyl, 1-(3-difluoromethoxyphenyl)-4-imidazolyl, 1-(7-benzo[b]furanyl)-4-imidazolyl, 1-(2-quinolyl)-4-imidazolyl, 1-(3-quinolyl)-4-imidazolyl, 1-phenyl-3-pyrazolyl, 5-phenyl-3-pyrazolyl, 1-phenyl-4-pyrazolyl, 1-(3-fluorophenyl)-4-pyrazolyl, 1-(4-fluorophenyl)-3-pyrazolyl, 5-(4-chlorophenyl)-3-pyrazolyl, 5-(3-quinolyl)-3-pyrazolyl, 5-phenyl-2-thiazolyl, 3-phenyl-5-isoxazolyl, 5-(2-methyl-1-propenyl)-2-pyrazinyl, 5-phenyl-2-pyrazinyl, 5-(3-hydroxyphenyl)-2-pyrazinyl, 5-(4-hydroxyphenyl)-2-pyrazinyl, 5-(2-pyridyl)-2-pyrazinyl, 5-benzoyl-2-pyrazinyl, 5-phenyl-2-pyrimidinyl, 5-(2-fluorophenyl)-2-pyrimidinyl, 5-(3-fluorophenyl)-2-pyrimidinyl, 5-(3-chlorophenyl)-2-pyrimidinyl, 5-(3-trifluoromethyl-phenyl)-2-pyrimidinyl, 5-chloro-2-benzoxazolyl, 4-methyl-2-benzothia-zolyl, 7-methyl-2-quinolyl, 7-trifluoromethylpyrido[3,2-b]pyridin-2-yl, and the like, especially 1-phenyl-3-pyrazolyl, 5-phenyl-3-pyrazolyl, 5-phenyl-2-pyrazinyl, 5-(3-hydroxyphenyl)- 2-pyrazinyl, 5-(4-hydroxyphenyl)-2-pyrazinyl, 5-phenyl-2-pyrimidinyl, 5-(2-fluorophenyl)-2-pyrimidinyl, 5-(3-fluorophenyl)-2-pyrimidinyl, 7-trifluoro-methylpyrido[3,2-b]pyridin-2-yl, and the like.

n represents 0 or 1, 0 is preferable.

T, U, V and W represent independently nitrogen atom or methine which may have a substituent selected from the group consisting of halogen, lower alkyl, hydroxy and lower alkoxy, where at least two of them represent the said methine group.

"Methine which may have a substituent selected from the group consisting of halogen, lower alkyl, hydroxy and lower alkoxy" refers to unsubstituted methine or methine having a substituent which can be selected from the group consisting of halogen, lower alkyl, hydroxy and lower alkoxy.

Halogen atom as the aforesaid substituent includes preferably fluorine atom, chlorine atom, and the like.

Lower alkyl as the aforesaid substituent includes preferably methyl, ethyl, and the like.

Lower alkoxy as the aforesaid substituent includes preferably methoxy, ethoxy, and the like.

The aforesaid substituent include preferably halogen, and the like.

The preferred mode of T, U, V and W includes, for example, T, U, V and W are independently methine optionally having the aforesaid substituent, preferably halogen; or one of T, U, V and W is nitrogen atom.

X represents methine or nitrogen.

Y represents imino which may be substituted with lower alkyl, or oxygen.

"Imino which may be substituted with lower alkyl" refers to unsubstituted imino or imino substituted with lower alkyl.

The aforesaid lower alkyl includes, preferably, methyl, ethyl, and the like.

Y is preferably unsubstituted imino or oxygen, especially oxygen.

In more detail, a group of formula (15):

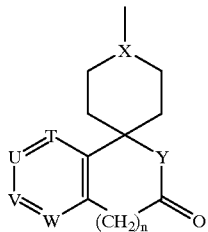

(15)

includes a group of formula (16):

(16)

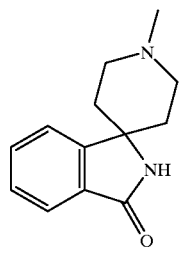

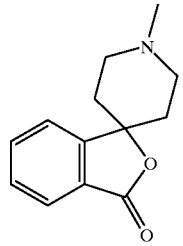

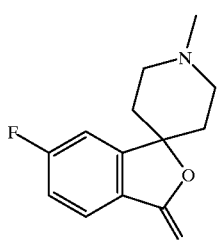

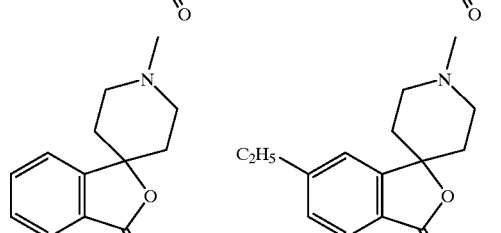

-continued

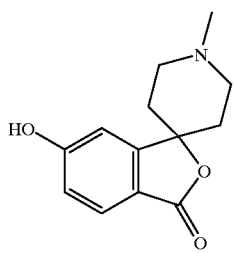

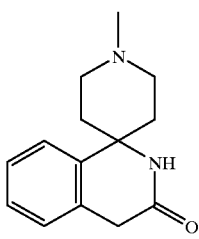

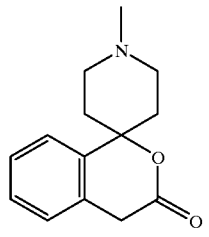

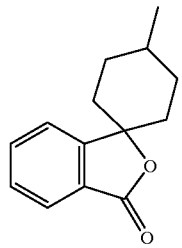

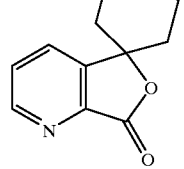

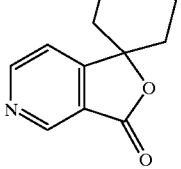

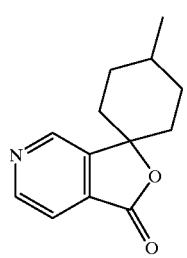 or 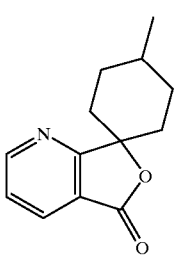

and the like.

Preferred compounds of the general formula (I) are, for example, compounds of the general formula (I-a):

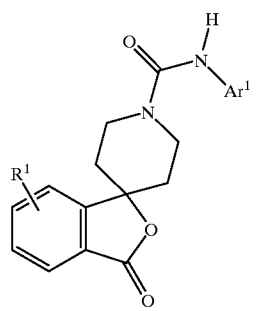

(I-a)

wherein $R^1$ represents hydrogen atom or halogen, $Ar^1$ has the aforesaid meaning;

or compounds of the general formula (I-b):

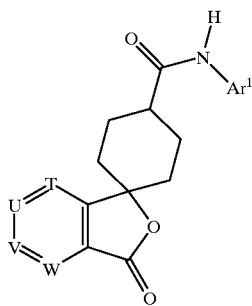

(I-b)

wherein Ar$^1$, T, U, V and W have the aforesaid meanings.

With regard to the compound represented by the general formula (I-a), the preferred compounds are, for example, the compounds, wherein the aryl group in Ar$^1$ is phenyl, or the heteroaryl group in Ar$^1$ is imidazolyl, pyrazolyl, isoxazolyl, 1,2,4-thiadiazolyl, pyrazinyl, pyrimidinyl, quinolyl or pyrido[3,2-b]pyridyl.

With regard to the compound represented by the general formula (I-b), the preferred compounds are, for example, the compounds, wherein the aryl group in Ar$^1$ is phenyl, or the heteroaryl group in Ar$^1$ is pyrrolyl, imidazolyl, pyrazolyl, thiazolyl, oxazolyl, isoxazolyl, 1,2,3-triazolyl, 1,2,4-thiadiazolyl, pyridyl, pyrazinyl, pyrimidinyl or 1,2,4-triazinyl.

Further, with regard to the compound represented by the general formula (I-b), the preferred compounds are, for example, the compounds, wherein one of T, U, V and W is a nitrogen atom and the more preferred compounds are, for example, the compounds wherein V is a nitrogen atom and T, U as well as W are an unsubstituted methine group.

Compounds of this invention may include stereoisomers such as optical isomers, diastereoisomers and geometrical isomers, or tautomers depending upon the mode of substituents. Compounds of this invention include all the stereoisomers, tautomers and their mixtures.

For example, compounds of the general formula (I-b) include stereoisomers such as trans-form compound of the general formula (I-1b):

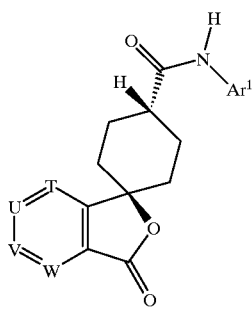

(I-1b)

and cis-form compound of the general formula (I-2b):

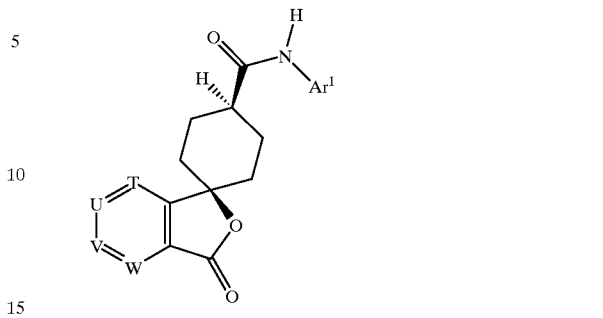

(I-2b)

trans form is preferable.

Also included within the scope of the invention are polymorphs, hydrates and solvates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The specific compound represented by the general formula (I) is, for example,

N-(4-benzoylphenyl)-3-oxospiro[isoindoline-1,4'-piperidine]-1'-carboxamide, 3-oxo-N-(5-phenyl-2-pyrazinyl)spiro[isoindoline-1,4'-piperidine]-1'-carboxamide, N-(7-methyl-2-quinolyl)-3-oxospiro[isoindoline-1,4'-piperidine]-1'-carboxamide, N-(4-benzoylphenyl)-2-methyl-3-oxospiro[isoindoline-1,4'-piperidine]-1'-carboxamide, N-(4-benzoylphenyl)-3,4-dihydro-3-oxospiro[isoquinoline-1(2H),4'-piperidine]-1'-carboxamide, 3,4-dihydro-3-oxo-N-(5-phenyl-2-pyrazinyl)spiro[isoquinoline-1(2H),4'-piperidine]-1'-carboxamide, 3,4-dihydro-N-(7-methyl-2-quinolyl)-3-oxospiro[isoquinoline-1(2H),4'-piperidine]-1'-carboxamide, N-(4-acetylphenyl)-3,4-dihydro-3-oxospiro[isoquinoline-1(2H),4'-piperidine]-1'-carboxamide, 3,4-dihydro-3-oxo-N-[1-(2-quinolyl)-4-imidazolyl]spiro[isoquinoline-1(2H),4'-piperidine]-1'-carboxamide, 3,4-dihydro-3-oxo-N-(5-oxo-5,6,7,8-tetrahydro-2-naphthyl)spiro[isoquinoline-1(2H),4'-piperidine]-1'-carboxamide, 3,4-dihydro-N-[5-(2-methyl-1-propenyl)-2-pyrazinyl]-3-oxospiro[isoquinoline-1(2H),4'-piperidine]-1'-carboxamide, 3,4-dihydro-3-oxo-N-(3-phenyl-5-isoxazolyl)spiro[isoquinoline-1(2H),4'-piperidine]-1'-carboxamide, N-[1-(7-benzo[b]furanyl)-4-imidazolyl]-3,4-dihydro-3-oxospiro[isoquinoline-1(2H),4'-piperidine]-1'-carboxamide, N-[1-(3-difluoromethoxyphenyl)-4-imidazolyl]-3,4-dihydro-3-oxospiro[isoquinoline-1(2H),4'-piperidine]-1'-carboxamide, 3,4-dihydro-3-oxo-N-[4-(2-pyridylcarbonyl)phenyl]spiro[isoquinoline-1(2H),4'-piperidine]-1'-carboxamide, N-(3,4-dichlorophenyl)-3,4-dihydro-3-oxospiro[isoquinoline-1(2H),4'-piperidine]-1'-carboxamide, N-[1-(3-chlorophenyl)-4-imidazolyl]-3,4-dihydro-3-oxospiro[isoquinoline-1(2H),4'-piperidine]-1'-carboxamide, 3,4-dihydro-3-oxo-N-(5-phenyl-2-thiazolyl)spiro[isoquinoline-1(2H),4'-piperidine]-1'-carboxamide, 3,4-dihydro-3-oxo-N-[5-(2-pyridyl)-2-pyrazinyl]spiro[isoquinoline-1(2H),4'-piperidine]-1'-carboxamide, 3,4-dihydro-N-(4-methyl-2-benzothiazolyl)- 3-oxospiro[isoquinoline-1(2H),4'-piperidine]-1'-carboxamide, N-(5-chloro-2-benzoxazolyl)-3,4-dihydro-3-oxospiro[isoquinoline-1(2H),4'-piperidine]-1'-carboxamide, N-(4-benzoylphenyl)-3-oxospiro[isobenzofuran-1(3H),4'-piperidine]-1'-carboxamide, 3-oxo-N-(5-phenyl-2-pyrazinyl)-spiro[isobenzofuran-1(3H),4'-piperidine]-1'-carboxamide, N-(7-methyl-2-quinolyl)-3-oxospiro[isobenzofuran-1(3H),4'-piperidine]-1'-carboxamide, 3-oxo-N-(3-phenyl-5-isoxazolyl)spiro[isobenzofuran-1(3H),4'-piperidine]-1'-carboxamide, 3-oxo-N-(7-trifluoromethylpyrido[3,2-b]pyridin-2-yl)spiro[isobenzofuran-1(3H),4'-piperidine]-1'-carboxamide, 3-oxo-N-(5-phenyl-2-pyrimidinyl)spiro[isobenzofuran-1(3H),4'-piperidine]-1'-carboxamide, 3-oxo-N-[1-(3-quinolyl)-4-imidazolyl]spiro[isobenzofuran-1(3H),4'-piperidine]-1'-carboxamide, 3-oxo-N-(5-phenyl-3-pyrazolyl)spiro[isobenzofuran-1(3H),4'-piperidine]-1'-carboxamide, N-[5-(4-chlorophenyl)-3-pyrazolyl]-3-oxospiro[isobenzofuran-1(3H),4'-piperidine]-1'-carboxamide, 3-oxo-N-[5-(3-quinolyl)-3-pyrazolyl]spiro[isobenzofuran-1(3H),4'-piperidine]-1'-carboxamide, N-[5-(3-fluorophenyl)-2-pyrimidinyl]- 3-oxospiro[isobenzofuran-1(3H),4'-piperidine]-1'-carboxamide, 3-oxo-N-[5-(3-trifluoromethylphenyl)-2-pyrimidinyl]spiro[isobenzofuran-1(3H),4'-piperidine]-1'-carboxamide, N-[5-(3-chlorophenyl)-2-pyrimidinyl]-3-oxospiro[isobenzofuran-1(3H),4'-piperidine]-1'-carboxamide, N-(7-difluoromethoxypyrido[3,2-b]pyridin-2-yl)-3-oxospiro[isobenzofuran-1(3H),4'-piperidine]-1'-carboxamide, 3-oxo-N-(5-phenyl-1,2,4-thiadiazol-3-yl)spiro[isobenzofuran-1(3H),4'-piperidine]-1'-carboxamide, N-{1-[3-(2-hydroxyethyl)phenyl]-4-imidazoly}-3-oxospiro[isobenzofuran-1(3H),4'-piperidine]-1'-carboxamide, N-[4-(1-ethyl-2-imidazolyl)phenyl]-3-oxospiro[isobenzofuran-1(3H),4'-piperidine]-1'-carboxamide, N-[1-(3-methoxyphenyl)-4-imidazolyl]-3-oxospiro[isobenzofuran-1(3H),4'-piperidine]-1'-carboxamide, 6-fluoro-3-oxo-N-(5-phenyl-2-pyrazinyl)spiro[isobenzofuran-1(3H),4'-piperidine]-1'-carboxamide, 6-fluoro-3-oxo-N-(5-phenyl-2-pyrimidinyl)spiro[isobenzofuran-1(3H),4'-piperidine]-1'-carboxamide, 5-fluoro-3-oxo-N-(5-phenyl-2-pyrazinyl)spiro[isobenzofuran-1(3H),4'-piperidine]-1'-carboxamide, 5-fluoro-3-oxo-N-(5-phenyl-2-pyrimidinyl)spiro[isobenzofuran-1(3H),4'-piperidine]-1'-carboxamide, N-(4-benzoylphenyl)-3,4-dihydro-3-oxospiro[1H-2-benzopyran-1,4'-piperidine]-1'-carboxamide, 3,4-dihydro-3-oxo-N-(5-phenyl-2-pyrazinyl)spiro[1H-2-benzopyran-1,4'-piperidine]-1'-carboxamide, N-(5-benzoyl-2-pyrazinyl)-3,4-dihydro-3-oxospiro[1H-2-benzopyran-1,4'-piperidine]-1'-carboxamide, trans-N-(4-benzoylphenyl)-3'-oxospiro[cyclohexane-1,1'(3'H)-isobenzofuran]-4-carboxamide, trans-3'-oxo-N-(5-phenyl-2-pyrazinyl)spiro[cyclohexane-1,1'(3'H)-isobenzofuran]-4-carboxamide, trans-3'-oxo-N-(1-phenyl-4-imidazolyl)spiro[cyclohexane-1,1'(3'H)-isobenzofuran]-4-carboxamide, trans-3'-oxo-N-(5-phenyl-2-pyrimidinyl)spiro[cyclohexane-1,1'(3'H)-isobenzofuran]-4-carboxamide, trans-N-[1-(3,5-difluorophenyl)-4-imidazolyl]-3'-oxospiro[cyclohexane-1,1'(3'H)-isobenzofuran]-4-carboxamide, trans-3'-oxo-N-(5-phenyl-3-pyrazolyl)spiro[cyclohexane-1,1'(3'H)-isobenzofuran]-4-carboxamide, trans-N-[1-(2-fluorophenyl)-4-imidazolyl]-3'-oxospiro[cyclohexane-1,1'(3'H)-isobenzofuran]-4-carboxamide, trans-N-(4-acetyl-3-trifluoromethylphenyl)-3'-oxospiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-N-[1-(3-cyanophenyl)-4-imidazolyl]-3'-oxospiro[cyclohexane-1,1'(3'H)-isobenzofuran]-4-carboxamide, trans-N-(4-benzoylphenyl)-3-oxospiro[4-azaisobenzofuran-1(3H),1'- cyclohexane]-4'-carboxamide, trans-3-oxo-N-(5-phenyl-2-pyrazinyl)spiro[4-azaisobenzofuran-1(3H),1'-cyclohexane]-4'-carboxamide, trans-3-oxo-N-(3-phenyl-5-isoxazolyl)spiro[4-azaisobenzofuran-1(3H),1'-cyclohexane]-4'-carboxamide, trans-3-oxo-N-(5-phenyl-2-pyrimidinyl)spiro[4-azaisobenzofuran-1(3H),1'-cyclohexane]-4'-carboxamide, trans-N-(4-benzoylphenyl)-3-oxospiro[5-azaisobenzofuran-1(3H),1'- cyclohexane]-4'-carboxamide, trans-N-(4-benzoylphenyl)-3-oxospiro[6-azaisobenzofuran-1(3H),1'- cyclohexane]-4'-carboxamide, N-[5-(4-hydroxyphenyl)-2-pyrazinyl]-3-oxospiro[isobenzofuran-1(3H),4'-piperidine]-1'-carboxamide, N-[5-(3-hydroxyphenyl)-2-pyrazinyl]-3-oxospiro[isobenzofuran-1(3H),4'-piperidine]-1'-carboxamide, 4-fluoro-3-oxo-N-(5-phenyl-2-pyrimidinyl)spiro[isobenzofuran-1(3H),4'-piperidine]- 1'-carboxamide, 7-fluoro-3-oxo-N-(5-phenyl-2-pyrimidinyl)spiro[isobenzofuran-1(3H),4'-piperidine]-1'-carboxamide, 6-ethyl-3-oxo-N-(5-phenyl-2-pyrazinyl)spiro[isobenzofuran-1(3H),4'-piperidine]-1'-carboxamide, 6-hydroxy-3-oxo-N-(5-phenyl-2-pyrazinyl)spiro[isobenzofuran-1(3H),4'-piperidine]-1'-carboxamide, trans-3-oxo-N-(5-phenyl-2-pyrimidinyl)spiro[5-azaisobenzofuran-1(3H),1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide, trans-3-oxo-N-(4-phenyl-2-oxazolyl)spiro[5-azaisobenzofuran-1(3H),1'-cyclohexane]-4'-carboxamide, trans-N-[5-(2-methylphenyl)-2-pyrimidinyl]-3-oxospiro[5-azaisobenzofuran-1(3H),1'-cyclohexane]-4'-carboxamide, trans-N-[5-(3-methylphenyl)-2-pyrimidinyl]-3-oxospiro[5-azaisobenzofuran-1(3H),1'-cyclohexane]-4'-carboxamide, trans-N-[5-(3-fluoromethoxyphenyl)-2-pyrimidinyl]-3-oxospiro[5-azaisobenzofuran-1(3H),1'-cyclohexane]-4'-carboxamide, trans-N-[5-(3-fluoromethylphenyl)-2-pyrimidinyl]-3-oxospiro[5-azaisobenzofuran-1(3H),1'-cyclohexane]-4'-carboxamide, trans-N-[5-(3-fluoro-5-methoxyphenyl)-2-pyrimidinyl]-3-oxospiro[5-azaisobenzofuran-1(3H),1'-cyclohexane]-4'-carboxamide, trans-N-[5-(2-fluoro-5-methylphenyl)-2-pyrimidinyl]-3-oxospiro[5-azaisobenzofuran-1(3H),1'-cyclohexane]-4'-carboxamide, trans-N-[4-(3-fluoromethoxyphenyl)-2-oxazolyl]-3-oxospiro[5-azaisobenzofuran-1(3H),1'-cyclohexane]-4'-carboxamide, trans-N-[5-(3-hydroxymethylphenyl)-2-pyrimidinyl]-3-oxospiro[5-azaisobenzofuran-1(3H),1'-cyclohexane]-4'-carboxamide, trans-N-[5-(3-hydroxyphenyl)-2-pyrimidinyl]-3-oxospiro[5-azaisobenzofuran-1(3H),1'-cyclohexane]-4'-carboxamide, trans-3-oxo-N-(5-phenyl-2-pyrimidinyl)spiro[6-azaisobenzofuran-1(3H),1'-cyclohexane]-4'-carboxamide, trans-N-[5-(3-fluoromethylphenyl)-2-pyrimidinyl]-3-oxospiro[6-azaisobenzofuran-1(3H),1'-cyclohexane]-4'-carboxamide, trans-N-[5-(3-fluoromethoxyphenyl)-2-pyrimidinyl]-3-oxospiro[6-azaisobenzofuran-1(3H),1'-cyclohexane]-4'-carboxamide, trans-3-oxo-N-(6-phenyl-1,2,4-triazin-3-yl)spiro[6-azaisobenzofuran-1(3H),1'-cyclohexane]-4'-carboxamide, trans-N-[5-(2-difluoromethoxyphenyl)-3-pyrazolyl]-3-oxospiro[6-azaisobenzofuran-1(3H),1'-cyclohexane]-4'-carboxamide, trans-N-[5-(3-difluoromethoxyphenyl)-3-pyrazolyl]-3-oxospiro[6-azaisobenzofuran-1(3H),1'-cyclohexane]-4'-carboxamide, trans-N-[5-(3-fluorophenyl)-3-pyrazolyl]-3-oxospiro[6-azaisobenzofuran-1(3H),1'-cyclohexane]-4'-carboxamide, trans-N-[5-(4-fluorophenyl)-3-pyrazolyl]-3-oxospiro[6-azaisobenzofuran-1(3H),1'-cyclohexane]-4'-carboxamide, trans-N-(4-benzoylphenyl)-3-oxospiro[7-azaisobenzofuran-1(3H),1'-cyclohexane]-4'-carboxamide, trans-N-[1-(3,5-difluorophenyl)-4-imidazolyl]-3-oxospiro[7-azaisobenzofuran-1(3H),1'-cyclohexane]-4'-carboxamide, trans-3-oxo-N-[2-phenyl-4-pyridyl]spiro[7-azaisobenzofuran-1(3H),1'-cyclohexane]-4'-carboxamide, trans-3-oxo-N-(1-phenyl-4-pyrazolyl)spiro[7-azaisobenzofuran-1(3H),1'-cyclohexane]-4'-carboxamide, trans-3-oxo-N-(1-phenyl-3-pyrrolyl)spiro[7-azaisobenzofuran-1(3H),1'-cyclohexane]-4'-carboxamide, trans-N-[1-(4-fluorophenyl)-3-pyrazolyl]-3-oxospiro[7-azaisobenzofuran-1(3H),1'-cyclohexane]-4'-carboxamide, trans-3-oxo-N-(1-phenyl-3-pyrazolyl)spiro[4-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide, trans-N-[1-(3-fluorophenyl)-4-pyrazolyl]-3-oxospiro[4-azaisobenzofuran-1(3H),1'-cyclohexane]-4'-carboxamide, trans-3-oxo-N-(1-phenyl-3-pyrazolyl)spiro[6-azaisobenzofuran-1(3H),1'-cyclohexane]-4'-carboxamide, trans-N-[1-(4-fluorophenyl)-3-pyrazolyl]-3-oxospiro[6-azaisobenzofuran-1(3H),1'-cyclohexane]-4'-carboxamide, trans-N-[1-(2-fluorophenyl)-3-pyrazolyl]-3-oxospiro[6-azaisobenzofuran-1(3H),1'-cyclohexane]-4'-carboxamide, trans-3-oxo-N-(5-phenyl-1,2,4-thiadiazol-3-yl)spiro[6-azaisobenzofuran-1(3H),1'-cyclohexane]-4'-carboxamide, trans-3-oxo-N-(5-phenyl-3-isoxazolyl)spiro[6-azaisobenzofuran-1(3H),1'-cyclohexane]-4'-carboxamide, trans-3-oxo-N-(6-phenyl-3-pyridyl)spiro[6-azaisobenzofuran-1(3H),1'-cyclohexane]-4'-carboxamide, trans-3-oxo-N-(2-phenyl-3-thiazolyl)spiro[6-azaisobenzofuran-1(3H),1'-cyclohexane]-4'-carboxamide or trans-3-oxo-N-(2-phenyl-1,2,3-triazol-4-yl)spiro[6-azaisobenzofuran-1(3H),1'-cyclohexane]-4'-carboxamide.

Among these compounds, the preferable compound is, for example, 3-oxo-N-(5-phenyl-2-pyrazinyl)-spiro[isobenzofuran-1(3H),4'-piperidine]-1'-carboxamide, 3-oxo-N-(7-trifluoromethylpyrido[3,2-b]pyridin-2-yl)spiro[isobenzofuran-1(3H),4'-piperidine]-1'-carboxamide, N-[5-(3-fluorophenyl)-2-pyrimidinyl]-3-oxospiro[isobenzofuran-1(3H),4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaisobenzofuran-1(3H),1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide, trans-N-[1-(3,5-difluorophenyl)-4-imidazolyl]-3-oxospiro[7-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide, trans-3-oxo-N-(1-phenyl-3-pyrazolyl)spiro[6-azaisobenzofuran-1(3H),1'-cyclohexane]-4'-carboxamide or trans-3-oxo-N-(2-phenyl-1,2,3-triazol-4-yl)spiro[6-azaisobenzofuran-1(3H),1'-cyclohexane]-4'-carboxamide.

The process for producing compounds of this invention is illustrated as follows.

Compounds of this invention (I) can be synthesized, for example, by the following processes for production or the processes shown in examples, but these embodiments are not intended to restrict the process for producing compounds of this invention (I).

Production Process 1

A compound of the general formula (II):

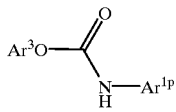

(II)

wherein Ar$^{1p}$ represents aryl or heteroaryl which may be substituted, the substituent being selected from the group consisting of halogen, nitro, lower alkyl, halo(lower)alkyl, cyclo(lower)alkyl, lower alkenyl, lower alkoxy, halo(lower)alkoxy, lower alkylthio, lower alkanoyl, lower alkoxycarbonyl, a group of formula: —Q$^p$—Ar$^{2p}$, and an optionally protected, lower alkylene optionally substituted with oxo, hydroxy(lower)alkyl or carboxyl group;

Ar$^{2p}$ represents aryl or heteroaryl which may be substituted, the substituent being selected from the group consisting of halogen, cyano, lower alkyl, halo(lower)alkyl, lower alkoxy, halo(lower)alkoxy, di-lower alkylamino, lower alkanoyl, aryl, and an optionally protected hydroxy(lower)alkyl, hydroxy or lower alkyl amino group;

Ar$^3$ represents phenyl which may be substituted by halogen or nitro;

Q$^p$ represents a single bond or optionally protected carbonyl; is reacted with a compound of the general formula (III):

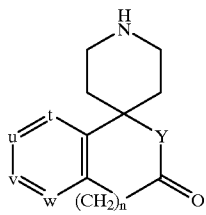

(III)

wherein n, t, u, v, w and Y have the same meanings as mentioned above;

to provide a compound of the general formula (IV-1):

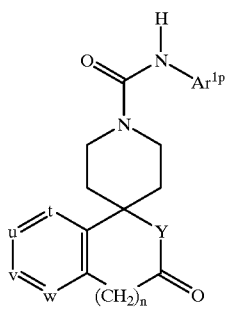

(IV-1)

wherein Ar$^{1p}$, n, t, u, v, w and Y have the same meanings as mentioned above;

optionally followed by elimination of a protective group to give a compound of the general formula (I-1):

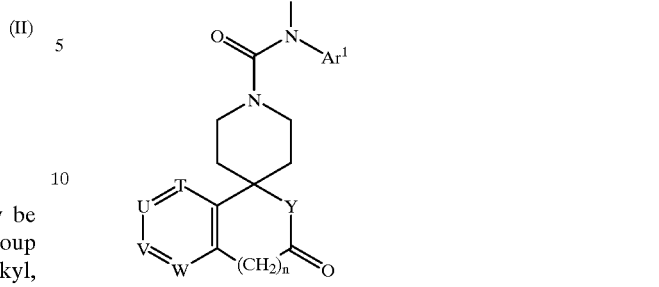

(I-1)

wherein Ar$^1$, n, T, U, V, W and Y have the same meanings as mentioned above.

This production process refers to the process for producing a compound of the general formula (I), wherein X is nitrogen, that is, a compound of the general formula (I-1).

When a reactant has an amino, hydroxy, carboxyl, oxo, carbonyl, or the like group which does not participate in the reaction, the reaction may be carried out after protecting the amino, hydroxy, carboxyl, oxo, carbonyl, or the like group with an amino protecting group, hydroxy protecting group, carboxyl protecting group, or oxo- or carbonyl-protecting group, followed by deprotection after completion of the reaction.

"Amino protecting group" includes aralkyl (for example benzyl, p-methoxybenzyl, 3,4-dimethoxybenzyl, o-nitrobenzyl, p-nitrobenzyl, benzhydryl, trityl); lower alkanoyl (for example formyl, acetyl, propionyl, butyryl, pivaloyl); benzoyl; arylalkanoyl (for example phenylacetyl, phenoxyacetyl); lower alkoxycarbonyl (for example methoxycarbonyl, ethoxycarbonyl, propyloxycarbonyl, tert-butoxycarbonyl); aralkyloxycarbonyl (for example benzyloxycarbonyl, p-nitrobenzyloxycarbonyl, phenethyloxycarbonyl); lower alkylsilyl (for example trimethylsilyl, tert-butyldimethylsilyl); and the like, especially acetyl, pivaloyl, benzoyl, ethoxycarbonyl, tert-butoxycarbonyl, and the like.

"Hydroxy protecting group" includes lower alkyl (for example methyl, ethyl, propyl, isopropyl, tert-butyl); lower alkylsilyl (for example trimethylsilyl, tert-butyldimethylsilyl); lower alkoxymethyl (for example methoxymethyl, 2-methoxyethoxymethyl); tetrahydropyranyl; trimethylsilylethoxymethyl; aralkyl (for example benzyl, p-methoxybenzyl, 2,3-dimethoxybenzyl, o-nitrobenzyl, p-nitrobenzyl, trityl); acyl (for example formyl, acetyl), and the like, especially methyl, methoxymethyl, tetrahydropyranyl, trityl, trimethylsilylethoxymethyl, tert-butyldimethylsilyl, acetyl, and the like.

"Carboxyl protecting group" includes lower alkyl (for example methyl, ethyl, propyl, isopropyl, tert-butyl); lower haloalkyl (for example 2,2,2-trichloroethyl); lower alkenyl (for example 2-propenyl); aralkyl (for example benzyl, p-methoxybenzyl, p-nitrobenzyl, benzhydryl, trityl); and the like, especially methyl, ethyl, tert-butyl, 2-propenyl, benzyl, p-methoxybenzyl, benzhydryl, and the like.

"Oxo- or carbonyl-protecting group" includes acetal or ketal (for example ethylene ketal, trimethylene ketal, dimethyl ketal), and the like.

The reaction between a compound of the general formula (II) and a compound of the general formula (III) is usually carried out by employing an equivalent to excessive mole, preferably an equivalent to 1.5 moles of compound (III) based on 1 mole of compound (II).

The reaction is usually carried out in an inert solvent, and as the inert solvent, made is use of, for example, methylene chloride, chloroform, tetrahydrofuran, dimethylformamide, dimethyl sulfoxide or the mixture, and the like, preferably.

The aforesaid reaction may be preferably carried out in the presence of base, including organic bases (for example triethylamine, diisopropylethylamine, pyridine, 4-dimethylaminopyridine) or inorganic bases (for example sodium hydroxide, potassium hydroxide), and the like.

The amount of the aforesaid base employed is usually an equivalent to excessive mole, preferably 1 to 5 moles based on 1 mole of a compound of the general formula (II).

Reaction temperature is usually −30° C. to 200° C. preferably 20° C. to 100° C.

Reaction time is usually 5 minutes to 7 days, preferably 30 minutes to 24 hours.

At the conclusion of the reaction, the crude product of a compound of the general formula (IV-1) can be obtained by usual treatment. Thus obtained compound (IV-1) is purified by the conventional method, or not purified, if necessary followed by optional combination of elimination reaction of amino-, hydroxy-, carboxyl-, oxo- and carbonyl-protecting group to give a compound of the general formula (I-1).

The elimination of protecting groups may be carried out depending upon the kinds of the aforesaid protecting groups, the stability of a desired compound (I-1) and so on, for example, by the manner described in the literature [Protective Groups in Organic Synthesis, T. W. Greene, John Wiley & Sons, (1981)] or its similar manner, for example, solvolysis using acid or base, that is, for example 0.01 mole to a large excess of acid, preferably trifluoroacetic acid, formic acid, hydrochloric acid, or the like, or an equivalent mole to a large excess of base, preferably potassium hydroxide, calcium hydroxide, or the like; chemical reduction using metallic complex hydride, or the like; or catalytic reduction using palladium-carbon catalyst, Raney nickel catalyst, or the like.

Production Process 2

A compound of the general formula (V):

(V)

wherein $Ar^{1p}$ has the same meaning as mentioned above; is reacted with a carboxylic acid of the general formula (VI):

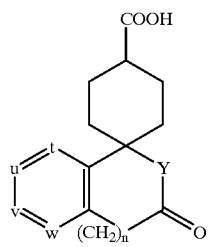

(VI)

wherein n, t, u, v, w and Y have the same meanings as mentioned above;

or its reactive derivative to provide a compound of the general formula (IV-2):

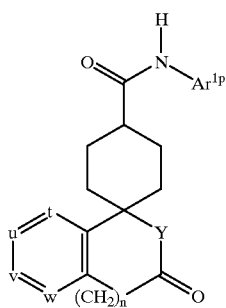

(IV-2)

wherein $Ar^{1p}$, n, t, u, v, w and Y have the same meanings as mentioned above; optionally followed by elimination of a protecting group to give a compound of the general formula (I-2):

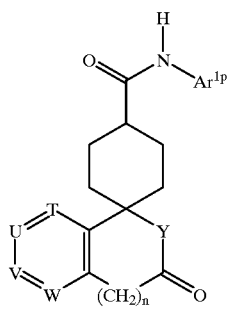

(I-2)

wherein $Ar^1$, n, T, U, V, W and Y have the same meanings as mentioned above.

This production process refers to the process for producing compounds of the general formula (I), wherein X is methine, that is, a compound of the general formula (I-2).

Reaction between a compound of the general formula (V) and a carboxylic acid of the general formula (VI) is usually carried out by employing 0.5 mole to excessive moles, preferably 1 mole to 1.5 mole of carboxylic acid (VI) based on 1 mole of compound (V).

The reaction is usually carried out in an inert solvent, and preferable examples of the inert solvent include methylene chloride, chloroform, tetrahydrofuran, dimethylformamide, pyridine or a mixture thereof, and the like.

The aforesaid reaction is preferably carried out in the presence of condensing agents, for example N,N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yl-oxy-tris-(dimethylamino)phosphonium hexafluorophosphate, benzotriazol-1-yloxy-tris-pyrrolidinophosphonium hexafluorophosphate, bromotris-(dimethylamino)phosphonium hexafluorophosphate, diphenylphosphoryl azide, 1,1'-carbonyldiimidazole, or the like.

The aforesaid condensing agent is usually employed at 1 mole to excessive mole, preferably. 1 mole to 1.5 moles based on 1 mole of compound (VI).

Reaction temperature is usually −50° C. to 100° C. preferably −20° C. to 50° C.

Reaction time is usually 30 minutes to 7 days, preferably 1 hour to 24 hours.

A compound of formula (I-2) is also produced by reacting a compound of the general formula (V) with a reactive derivative of the carboxylic acid (VI) instead of the carboxylic acid (VI).

The reactive derivatives of carboxylic acid of the general formula (VI) include acid halides, mixed acid anhydrides, activated esters, activated amides, and the like.

The acid halides of carboxylic acid of the general formula (VI) may be obtained by reacting a carboxylic acid of the general formula (VI) with a halogenating agent according to the conventional method. Halogenating agent includes thionyl chloride, phosphorus trichloride, phosphorus pentachloride, phosphorus oxychloride, phosphorus tribromide, oxalyl chloride, phosgene, and the like.

The mixed acid anhydrides of carboxylic acid of the general formula (VI) may be obtained by reacting a carboxylic acid of the general formula (VI) with alkyl chlorocarbonate (for example ethyl chlorocarbonate); aliphatic carboxylic acid chloride (for example pivaloyl chloride), and the like according to the conventional method.

The activated esters of carboxylic acid of the general formula (VI) may be obtained by reacting a carboxylic acid of the general formula (VI) with N-hydroxy compound (for example N-hydroxysuccinimide, N-hydroxyphthalimide, 1-hydroxybenzotriazole); phenol compound (for example 4-nitrophenol, 2,4-dinitrophenol, 2,4,5-trichlorophenol, pentachlorophenol), or the like in the presence of a condensing agent (for example N,N'-dicyclohexylcarbodiimide, 1-(3-dimethylaminopropyl)-3-ethylcarbodi-imide) according to the conventional method.

The activated amides of carboxylic acid of the general formula (VI) may be obtained by reacting a carboxylic acid of the general formula (VI) with for example 1,1'-carbonyldiimidazole, 1,1'-carbonylbis(2-methylimidazole), or the like according to the conventional method.

Reaction between a compound of the general formula (V) and a reactive derivative of the carboxylic acid of the general formula (VI) is usually carried out by employing 0.5 mole to excessive mole, preferably 1 mole to 1.5 moles of the reactive derivative of carboxylic acid (VI) based on 1 mole of compound (V).

The reaction is usually carried out in an inert solvent, and preferable examples of the inert solvent include methylene chloride, chloroform, tetrahydrofuran, dimethylformamide, pyridine or a mixture thereof, and the like.

The aforesaid reaction proceeds in the absence of bases, but it is preferable to carry out the reaction in the presence of bases to promote the reaction smoothly.

The aforesaid bases include organic bases (for example triethylamine, diisopropylethylamine, pyridine, 4-dimethylaminopyridine) or inorganic bases (for example sodium hydroxide, potassium hydroxide, sodium carbonate, potassium carbonate, sodium hydrogen carbonate), and the like.

It is preferable to employ 1 mole to excessive mole of the aforesaid base to 1 mole of a compound of the general formula (V). When the aforesaid base is liquid, the aforesaid base can also be used as a solvent.

Reaction temperature is usually −50° C. to 100° C. preferably −20° C. to 50° C.

Reaction time is usually 5 minutes to 7 days, preferably 30 minutes to 24 hours.

A compound of the general formula (I-2) can be produced by treating a reaction mixture in the usual way after deprotection if the product has a protecting group at the conclusion of the reaction, or by treating the mixture directly in the usual way if the protective group is absent.

Elimination of the protecting groups and post-treatment, and the like can be carried out according to the method described in the aforesaid production process 1.

Compounds of the general formula (I-1) or (I-2) may readily be isolated and purified by the conventional separation technique, for example, solvent extraction, recrystallization, column chromatography, preparative thin layer chromatography, or/and the like.

These compounds may be converted into the pharmaceutically acceptable salts or esters by the conventional method, on the contrary, the conversion of the salts or esters into free compounds may also be carried out according to the conventional method.

Compounds of the general formula (II), (III), (V) or (VI) are commercially available, or are prepared according to the methods described in the literature [Japanese Patent Unexamined Publication No.94/263737-A, U.S. Pat. No. 3,301, 857, J. Org. Chem, 40: 1427 (1975), International Patent Publication WO95/28389 or the like], or analogous methods thereto or the methods shown below or in Examples, optionally in combination.

Production Process A

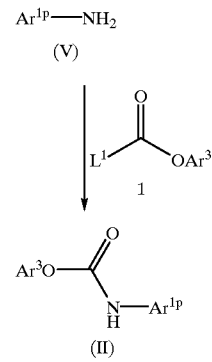

wherein $L^1$ represents halogen; $Ar^{1p}$ and $Ar^3$ have the same meanings as given above;

This process refers to a process for producing a compound of the general formula (II). Compound (II) is prepared by reacting a compound of the general formula (V) with a compound of the general formula 1 according to this process.

The reaction between a compound (V) and a compound 1 is usually carried out by employing 0.5 mole to excessive mole, preferably an equivalent to 1.5 moles of compound 1 based on 1 mole of compound (V).

The reaction is usually carried out in an inert solvent, and the preferable examples of the inert solvent include methylene chloride, chloroform, tetrahydrofuran, ethyl ether, benzene, toluene, dimethylformamide or a mixture thereof, and the like.

It is preferable to carry out the reaction in the presence of bases. The aforesaid bases include organic bases (for example triethylamine, diisopropylethylamine, pyridine, 4-dimethylaminopyridine) or inorganic bases (for example sodium hydroxide, potassium hydroxide, sodium carbonate, potassium carbonate, sodium hydrogen carbonate), and the like.

It is preferable to employ an equivalent to excessive mole of the aforesaid base to 1 mole of a compound (V). When the aforesaid base is liquid, the aforesaid base can be used also as a solvent.

Reaction temperature is usually −78° C. to 100° C. preferably −20° C. to 50° C.

Reaction time is usually 5 minutes to 7 days, preferably 30 minutes to 24 hours.

Compounds of formula I are commercially available, or are prepared according to the conventional method, the methods described in Examples, or the like methods, optionally in combination.

Production Process B

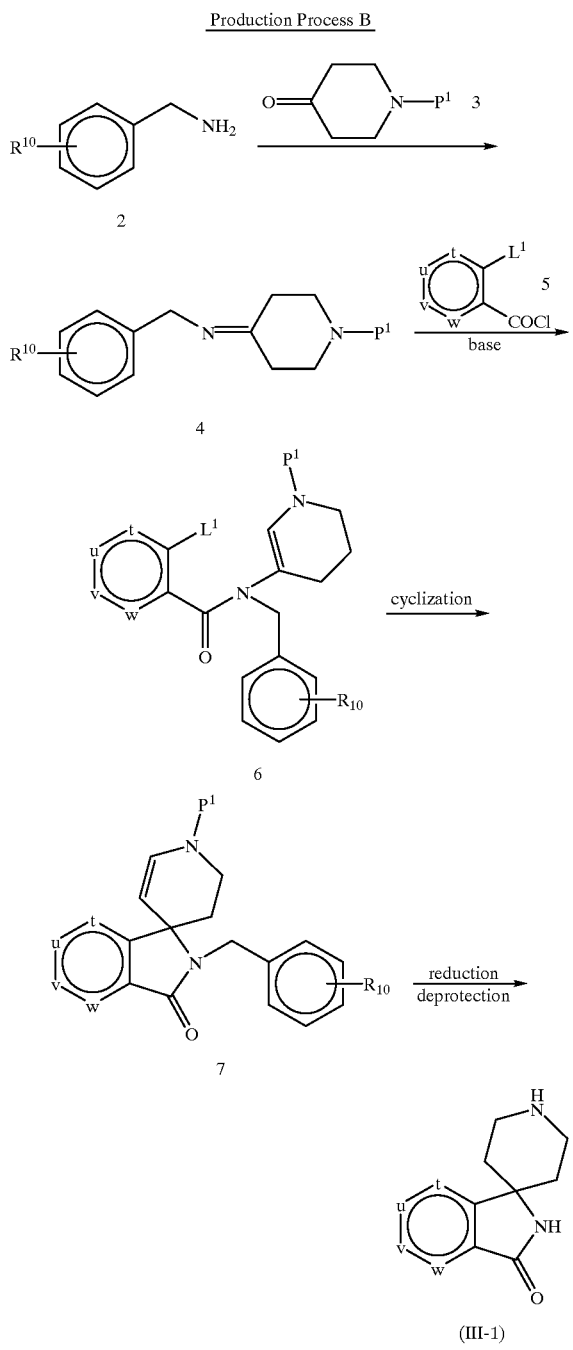

wherein $P^1$ represents an amino protecting group;

$R^{10}$ represents hydrogen, nitro, lower alkyl or lower alkoxy;

$L^1$, t, u, v and w have the same meanings as given above.

This process refers to a process for producing compounds of the general formula (III-1). Compound (III-1) may so be prepared by the present process that a compound of the general formula 2 is subjected to dehydrogenated condensation with a compound of the general formula 3 to give a compound of the general formula 4, which is subjected to reaction with a compound of the general formula 5 in the presence of a base to yield a compound of the general formula 6 and then the compound 6 is cyclized by an intra-molecular Heck reaction to give a compound of the general formula a, and then the compound 7 is subjected to reduction, optionally followed by elimination of amino protecting group $P^1$.

Amino protecting group $P^1$ includes the amino protecting groups described in the aforesaid production process 1.

A step for preparing compound A by dehydrogenated condensation of compound 2 with compound 3 is usually carried out in an inert solvent, for example benzene, toluene, or the like.

Reaction temperature is preferably from room temperature to the boiling point of a solvent used and reaction time is preferably from 30 minutes to 24 hours.

A step for preparing compound 6 from compound 4 is usually carried out in an inert solvent (for example benzene, toluene, methylene chloride, chloroform, acetonitrile, dimethylformamide) in the presence of base (for example triethylamine, diisopropylethylamine, pyridine, 4-dimethylaminopyridine).

Reaction temperature is preferably from 0° C. to the boiling point of a solvent used and reaction time is preferably from 30 minutes to 24 hours.

So-called intramolecular Heck reaction well known in the field of organic chemistry can be applied to the step for preparing compound 7 from compound 6.

The aforesaid step is usually carried out in an inert solvent (for example benzene, toluene, tetrahydrofuran, acetonitrile, dimethylformamide, N-methylpyrrolidone) in the presence of palladium catalyst (for example palladium acetate, palladium chloride), phosphine ligand (for example triphenylphosphine, tri-2-furylphosphine) and base (for example potassium carbonate, triethylamine), optionally additives (for example tetraethylammonium chloride).

Reaction temperature is preferably from room temperature to the boiling point of a solvent used in reaction and reaction time is preferably from 30 minutes to 24 hours.

As a method for reduction in the step for preparing compound (III-1) from compound 7, for example catalytic reduction is preferable.

The catalytic reduction is usually carried out in an inert solvent (for example methanol, ethanol, methylene chloride, chloroform, tetrahydrofuran, dimethylformamide, acetic acid) in the presence of a catalyst such as palladium-carbon at 1 to 50 atmospheric pressure of hydrogen.

Reaction temperature is preferably from room temperature to the boiling point of a solvent used and reaction time is preferably from 30 minutes to 24 hours.

At the conclusion of the reaction, if a reaction product has a protecting group, compound (III-1) can be prepared by elimination of the protecting group.

Elimination of a protecting group can be carried out according to the method described in the aforesaid production process 1.

This step may also be carried out by elimination of the protecting group of compound 7, followed by reduction of the resulting compound.

Compounds of the general formula 2, 3 or 5 are commercially available, or may be prepared according to the conventional method, the methods shown in Examples, or the like methods, optionally in combination.

Production Process C

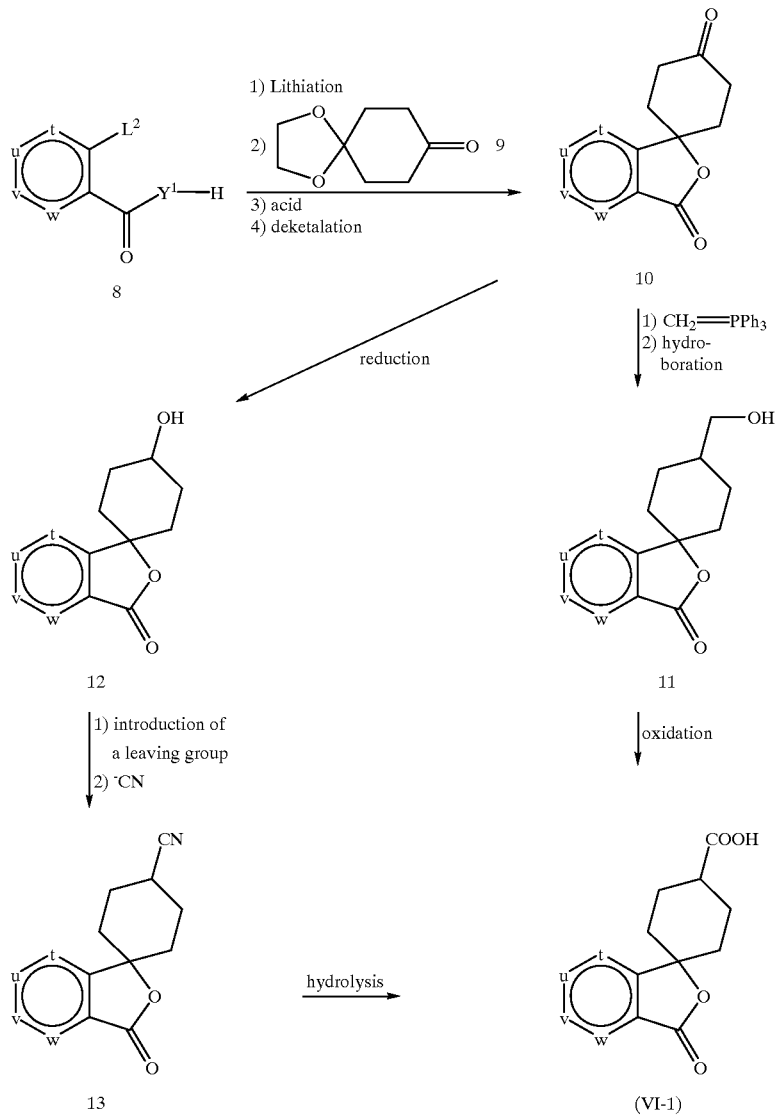

wherein $L^2$ represents hydrogen or halogen;

Ph represents phenyl;

$Y^1$ represents oxygen or imino substituted with lower alkyl or aryl;

t, u, v and w have the same meanings as given above.

This production process refers to the process for preparing compound of the general formula (VI-1). The compound represented by the general formula of (VI-1) is novel compound, which is not disclosed in the literature. The compound can be produced according to the present production process, that is, a compound of the general formula B is subjected to lithiation, reaction with compound 9 and lactonization with an acid, followed by deketalation to yield a compound of the general formula 10; and 1) methylene group is introduced to the compound 10, which is followed by hydroboration to give a compound of the general formula 11, and the compound is subjected to oxidation reaction, or 2) the compound 10 is reduced to give a compound of the general formula 12, which is subjected to introduction of a leaving group and then cyanization to give a compound of the general formula 13, followed by hydrolysis of the compound 13 at the cyano group.

Lithiation in the step preparing compound 10 from compound 8 is usually carried out by allowing compound 8 to be acted on by an organic lithium reagent (for example n-butyllithium, lithium 2,2,6,6-tetramethyl-piperidide) in an inert solvent (for example tetrahydrofuran, diethyl ether).

Reaction temperature is usually from −120° C. to 0°C., preferably from −100° C. to −50° C. and reaction time is preferably from 1 hour to 4 hours.

Reaction between the resulting lithio type and a ketone of the general formula 9 is usually carried out in an inert solvent (for example tetrahydrofuran, diethyl ether).

Reaction temperature is preferably from −100° C. to room temperature and reaction time is preferably from 10 minutes to 2 hours.

The resulting compound can be lactonized by treating with an acid (for example hydrochloric acid, sulfuric acid).

Reaction temperature is preferably from 0° C. to the boiling point of a solvent used and reaction time is preferably from 30 minutes to 8 hours.

Compound 10 can be prepared by subjecting the resulting lactone type to deketalation according to the conventional method.

Reaction temperature is preferably from 50° C. to the boiling point of a solvent used and reaction time is preferably from 1 hour to 24 hours.

The method used for converting oxo group to hydroxymethyl group, which is well known in the field of organic chemistry, can be applied to the step for preparing compound 11 from compound 10 and the step is usually carried out by reacting compound 10 with for example methylenetriphenylphosphorane to introduce a methylene group, followed by hydroboration in an inert solvent (for example benzene, toluene, methylene chloride, chloroform, acetonitrile, tetrahydrofuran, dimethylformamide).

In both steps for introducing methylene group and for hydroboration, reaction temperature is preferably from 0° C. to the boiling point of a solvent used and reaction time is preferably from 30 minutes to 8 hours.

The method used for oxidizing hydroxymethyl group to carboxyl group, which is well known in the field of organic chemistry, can be applied to the step for preparing compound (VI-1) from compound 11 and the step is usually carried out by using an oxidizing agent such as sodium periodate and a catalytic amount of ruthenium chloride, in an inert solvent (for example benzene, toluene, methylene chloride, chloroform, acetonitrile, dimethylformamide).

Reaction temperature is preferably from 0° C. to the boiling point of a solvent used and reaction time is preferably from 30 minutes to 8 hours.

The method used for reducing oxo group to hydroxyl group, which is well known in the field of organic chemistry, can be applied to the step for preparing compound 12 from compound 10 and the step is usually carried out by using a reducing agent (for example sodium borohydride, lithium borohydride), in an inert solvent (for example water, methanol, ethanol, tetrahydrofuran or a mixture thereof).

Reaction temperature is preferably from −20° C. to 50° C. and reaction time is preferably from 10 minutes to 4 hours.

The method used for converting hydroxy group to cyano group, which is well known in the field of organic chemistry, can be applied to the step for preparing compound 13 from compound 12 and the step is usually carried out by reacting compound 12 with for example methanesulfonyl chloride, p-toluenesulfonyl chloride, or the like to convert hydroxy group to a leaving group in the presence of base (for example triethylamine, pyridine), followed by reacting the resulting compound with a cyanide (for example sodium cyanide, potassium cyanide, tetraethylammonium cyanide, tetrabutylammonium cyanide).

The step for converting hydroxy group to a leaving group is usually carried out in an inert solvent (for example methylenechloride, chloroform, ethylacetate, acetonitrile, tetrahydrofuran, dimethylformamide). Reaction temperature is preferably from −20° C. to room temperature and reaction time is preferably from 10 minutes to 8 hours.

The step for reacting with a cyanide is usually carried out in an inert solvent (for example tetrahydrofuran, dioxane, dimethylformamide, N-methylpyrrolidone, dimethyl sulfoxide). Reaction temperature is preferably from 50° C. to 120° C. and reaction time is preferably from 2 to 24 hours.

Hydrolysis of cyano group, which is well known in the field of organic chemistry, can be applied to the step for preparing compound (VI-1) by hydrolysis of the cyano group of compound 13 and the step is usually carried out by using an acid (for example hydrochloric acid, sulfuric acid) or a base (for example sodium hydroxide, potassium hydroxide, calcium hydroxide), in a solvent (for example methanol, ethanol, tetrahydrofuran, dioxane, water or a mixture thereof).

Reaction temperature is preferably from 50° C. to the boiling point of a solvent used and reaction time is preferably from 1 to 48 hours.

Compounds of the general formula (VI-1) have two kinds of stereoisomers represented by the general formula (VI-1-a) or (VI-1-b):

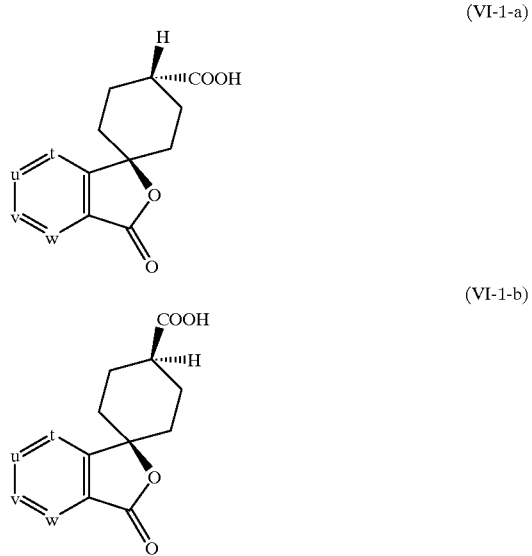

wherein t, u, v and w have the same meanings as given above.

These stereoisomers can be separated from the mixture by the conventional method such as chromatography, fractional recrystallization, and the like.

Compounds of the general formula (VI-1-a) or (VI-1-b) can be prepared by using an intermediate product which is obtained by separation of the stereoisomers of the general compound 11, 12 or 13.

Compounds of the general formula 8 or 9 are commercially available, or are prepared according to the conventional method, the methods described in Examples, or the like methods, optionally in combination.

The utility of compounds of the present invention as a medicament is proved by describing NPY antagonistic activity, for example, in the following pharmacological tests.

Pharmacological Test 1 (NPY Binding Inhibition Test)

cDNA sequence encoding human NPY Y5 receptor [International patent publication number WO96/16542] was cloned into expression vectors pcDNA3, pRc/RSV (made by Invitrogen Inc.) and pCI-neo (made by Promega Inc.). This obtained expression vectors were transfected to host cells COS-7, CHO and LM(tk−) (American Type Culture Collection) by cationic lipid method [Proceedings of the National Academy of Sciences of the United States of America, 84: 7413(1987)] to give NPY Y5 receptor expression cells.

A membrane sample prepared from the cells which expressed NPY Y5 receptor was incubated together with a test compound and [$^{125}$I]peptideYY (NEN) (20,000 cpm) in an assay buffer (25 mM Tris buffer, pH7.4, containing 10 mM magnesium chloride, 1 mM phenylmethylsulfonyl fluoride, 0.1% bacitracin and 0.5% bovine serum albumin) at 25° C. for 2 hours, then filtered through a glass filter GF/C and washed with 5 mM Tris buffer (pH7.4) containing 0.3%

BSA. The radioactivity of the cake on the glass filter was measured. Nonspecific binding was measured in the presence of 1 μM peptideYY and a 50% Inhibitory Concentration (IC50) of the test compound against specific peptideYY binding was determined [Endocrinology, 131: 2090(1992)]. The results are summarized in Table 1.
[Table 1]
Inhibitory Activities on NPY Receptor Binding

| Compounds | IC50 (nM) |
|---|---|
| Example 1 | 1.2 |
| Example 9 | 0.72 |
| Example 23 | 1.9 |
| Example 26 | 2.5 |
| Example 32 | 0.91 |
| Example 44 | 1.5 |
| Example 50 | 0.48 |
| Example 55 | 0.59 |

As shown above, compounds of this invention potently inhibited peptideYY (NPY homologue) binding to NPY Y5 receptors.
Pharmacological Test 2 (Antagonistic Effect on bPP-induced Feeding Behavior)

A guide cannula (external diameter 0.8 mm, internal diameter 0.5 mm, length 10 mm) was inserted stereotaxicly into the right lateral ventricle of male SD rats (7–8 weeks old, 200–300 g) anesthetized with pentobarbital (single intraperitoneal administration of 50 mg/kg) and fixed by dental resin. The top of the cannula was located 0.9 mm behind bregma, 1.2 mm to the right of median line and 1.5 mm depth from the brain surface so that, when injection needle is inserted into the guide cannula, the needle extends 2 mm beyond the tip of the guide cannula and reaches the lateral ventricle. After about 1-week recovery period, bovine pancreatic polypeptide (bPP, 5 μg/10 μL/head, 0.01M, pH7.4 phosphate buffered saline solution containing 0.05% bovine serum albumin) was injected into the lateral ventricle. A test compound suspended in aqueous 0.5% methylcellulose was administered orally 2 hours before the administration of bPP and the food consumption was measured 2 hours after administration of bPP.

Compounds of this invention significantly inhibited the increase in food consumption induced by bPP (NPY homologue) which was administered to the lateral ventricle.

Compounds of the general formula (I) can be administered orally or parenterally and may be formulated in the form suitable for administration to provide an agent for treatment of various diseases related to NPY, which include, for example, cardiovascular disorders (for example hypertension, nephropathy, heart disease, vasospasm, arteriosclerosis), central nervous system disorders (for example bulimia, depression, anxiety, seizure, epilepsy, dementia, pain, alcoholism, drug withdrawal), metabolic diseases (for example obesity, diabetes, hormone abnormality, hypercholesterolemia, hyperlipidemia), sexual and reproductive dysfunction, gastro-intestinal motility disorder, respiratory disorder, inflammation or glaucoma and the like, preferably, bulimia, obesity, diabetes and the like. In clinical use, compounds of this invention can be administered after being formulated, together with pharmaceutically acceptable additives, into an appropriate preparation according to the mode of administration. For said additives, those which are usually used in the field of pharmaceutical formulation may be used, for example, gelatin, lactose, sucrose, titanium oxide, starch, crystalline cellulose, hydroxypropyl methylcellulose, carboxymethylcellulose, corn starch, microcrystalline wax, white petrolatum, magnesium methasilicate aluminate, anhydrous calcium phosphate, citric acid, sodium citrate, hydroxypropyl cellulose, sorbitol, sorbitan fatty acid ester, polysorbate, sucrose fatty acid ester, polyoxyethylene, hydrogenated castor oil, polyvinylpyrrolidone, magnesium stearate, light silicic anhydride, talc, vegetable oil, benzyl alcohol, gum arabic, propylene glycol, polyalkylene glycol, cyclodextrin or hydroxypropyl cyclodextrin.

A mixture with said additives may be formulated in the form of solid preparations (for example tablets, capsules, granules, powder, suppositories); or liquid preparations (for example syrups, elixirs, injections). Such preparations may be formulated according to techniques well-known in the art of pharmaceutical formulation. Liquid preparations may be in the form of preparations which are dissolved or suspended in water or other appropriate media when used and especially injectable preparations may be dissolved or suspended in physiological saline or glucose solution if necessary, optionally together with a buffer and preservative.

Such preparations may contain 0.1 to 100 wt. %, preferably 1.0 to 60 wt. % of compounds of this invention and may also contain therapeutically effective other compounds.

The compounds of the present invention can be used in combination with other agents useful for treating metabolic and/or feeding disorders. The individual components of such combinations can be administered separately at different times during the course of therapy or concurrently individed or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating metabolic and/or feeding disorders includes in principle any combination with any pharmaceutical composition useful for treating metabolic and/or feeding disorders.

When compounds of this invention are used clinically, the dose and frequency of dosage may be varied depending upon the sex, age, body weight, the degree of symptoms and the kind and range of the desired treatment effects. A daily dose for an adult is 0.01–100 mg/kg, preferably 0.03–3 mg/kg orally, or 0.001–10 mg/kg, preferably 0.001–0.1 mg/kg parenterally, preferably in a single dose or in divided doses.

An ordinarily skilled physician, veterinarian or clinician can readily determine and prescribe the effective amount of the drug required to prevent, counter or arrest the progress of the condition.

EXAMPLES

The following examples are provided so that the present invention may be more concretely illustrated but they should not be construed as limiting the invention in any way.

Unless otherwise noted, melting point was measured by MP-S3 Model (manufactured by Yanagimoto Seisakusho) and disclosed in this specification without correction.

Example 1

Preparation of N-(4-benzoylphenyl)-3-oxospiro [isoindoline-1.4'-piperidine]-1'-carboxamide
(1) Preparation of N-benzyl-N-(1-tert-butoxycarbonyl-1,2, 3,6-tetrahydropyridin-4-yl)-2-iodobenzamide A mixture of N-tert-butoxycarbonyl-4-piperidone (1.11 g) and benzylamine (597 mg) dissolved in toluene (20 mL) was stirred at 100° C. for 3 hours and then concentrated. Toluene (30 mL), o-iodobenzoyl chloride (1.13 g) and triethylamine (0.70 g) were added to the residue and the mixture was stirred at 80° C. for 2 hours. The reaction mixture was poured into water and extracted with ethyl acetate. The ethyl acetate layer was dried over anhydrous $Na_2SO_4$ and concentrated. The residue was purified by column chromatography on silica gel (hexane/ethyl acetate=4/1 to 1/2) to give the subject compound (2.44 g).

(2) Preparation of 2-benzyl-1'-tert-butoxycarbonyl-1',6'-dihydro-spiro[1H-isoindole-1,4'(5'H)-pyridine]-3(2H)-one To N-benzyl-N-(1-tert-butoxycarbonyl-1,2,3,6-tetrahydropyridin-4-yl)-2-iodobenzamide (2.4 g) dissolved in acetonitrile, palladium acetate (80 mg), triphenylphosphine (187 mg), anhydrous $K_2CO_3$ (987 mg) and tetraethylammonium chloride (591 mg) were added and stirred at 80° C. for 6 hours. The reaction mixture was poured into water and extracted with ethyl acetate. The ethyl acetate layer was dried over anhydrous $Na_2SO_4$ and concentrated. The residue was purified by column chromatography on silica gel (hexane/ethyl acetate=4/1 to 1/2) to give the subject compound (1.64 g).

(3) Preparation of 2-benzyl-1'-tert-butoxycarbonylspiro[1H-isoindole-1,4'-piperidine]-3(2H)-one To a solution of 2-benzyl-1'-tert-butoxycarbonyl-1',6'-dihydrospiro[1H-isoindole-1,4'(5'H)-pyridine]-3(2H)-one (1.0 g) in chloroform (20 mL), trifluoroacetic acid (20 mL) was added and the mixture was stirred for 1 hour. The reaction mixture was concentrated. The residue was dissolved in methanol and hydrogenated with 4M hydrogen chloride/ethyl acetate in the presence of 20% palladium carbon at 1 atm of hydrogen for 14 hours. The catalyst was removed by filtration and the filtrate was concentrated. To the residue, aqueous 1N sodium hydroxide (5 mL), di-tert-butyl dicarbonate (655 mg) and dioxane (10 mL) were added and the mixture was stirred at room temperature for 4 hours. The reaction mixture was poured into water and extracted with ethyl acetate. The organic layer was dried over anhydrous $Na_2SO_4$ and concentrated. The residue was purified by column chromatography on silica gel (hexane/ethyl acetate= 4/1 to 1/2) to give the subject compound (200 mg).

(4) Preparation of spiro[1H-isoindole-1,4'-piperidine]-3(2H)-one hydrochloride

2-Benzyl-1'-tert-butoxycarbonylspiro[1H-isoindole-1,4'-piperidine]-3(2H)-one (200 mg) was added to metallic sodium (235 mg) in liquid ammonia (10 mL) and the mixture was stirred for 30 minutes. To the reaction mixture was added methanol, neutralized with a saturated ammonium chloride aqueous solution and extracted with ethyl acetate. The organic layer was dried over anhydrous $Na_2SO_4$ and concentrated. The residue dissolved in methanol was stirred together with 4M hydrogen chloride/ethyl acetate at 50° C. for 1 hour. The reaction solution was concentrated to give the subject compound (591 mg).

$^1$H-NMR (300 MHz, DMSO-$d_6$, δ ppm): 1.70–1.90 (2H, m), 2.00–2.20 (2H,m), 3.00–3.20 (2H,m), 4.20–4.40 (2H, m), 7.40 (1H, d, J=7.5 Hz), 7.51 (1H, t, J=7.5 Hz), 7.59 (1H, t, J=7.5 Hz), 7.84 (1H, d, J=7.5 Hz).

(5) Preparation of phenyl N-(4-benzoylphenyl)carbamate

To 4-aminobenzophenone (1.97 g) dissolved in pyridine (50 mL), phenyl chlorocarbonate (1.38 g) was added at 0° C. and the mixture was stirred at room temperature for 1 hour. The reaction mixture was poured into water and extracted with ethyl acetate. The organic layer was dried over anhydrous $Na_2SO_4$ and evaporated. The residue was purified by column chromatography on silica gel (hexane/ethyl acetate= 4/1 to 1/2) to give the subject compound (3.1 g).

(6) Preparation of N-(4-benzoylphenyl)-3-oxospiro [isoindoline-1,4'-piperidine]-1'-carboxamide A mixture of spiro[1H-isoindole-1,4'-piperidine]-3(2H)-one hydrochloride (48 mg), triethylamine (0.14 mL) and phenyl N-(4-benzoylphenyl)carbamate (58 mg) was stirred in chloroform at 80° C. for 2 hours. The reaction mixture was poured into water and extracted with chloroform. The organic layer was dried over anhydrous $Na_2SO_4$ and concentrated. The residue was purified by column chromatography on silica gel (hexane/ethyl acetate=4/1 to 1/2) and crystallized from ethyl ether-hexane to give the subject compound (49 mg) as colorless crystals (melting point 253° C.).

Compounds of Example 2 and 3 were obtained in the similar manner as Example 1-(6) by replacing phenyl N-(4-benzoylphenyl)carbamate used in Example 1-(6) by the corresponding materials, respectively.

Example 2

3-oxo-N-(5-phenyl-2-pyrazinyl)spiro[isoindoline-1, 4'-piperidine]-1'-carboxamide melting point 286–287° C.

Example 3

N-(7-methyl-2-quinolyl)-3-oxospiro[isoindoline-1, 4'-piperidine]-1'-carboxamide melting point 194–196° C.

Example 4

Preparation of N-(4-benzoylphenyl)-2-methyl-3-oxospiro[isoindoline-1,4'-piperidine]-1'-carboxamide The subject compound was obtained in the similar manner as Example 1-(6) by replacing spiro[1H-isoindole- 1,4'-piperidine]-3(2H)-one hydrochloride by 2-methylspiro[1H-isoindole-1,4'-piperidine]-3(2H)-one hydrochloride.

melting point 154–156° C.

Example 5

Preparation of N-(4-benzoylphenyl)-3,4-dihydro-3-oxospiro[iso-quinoline-1(2H),4'-piperidine]-1'-carboxamide Spiro[isoquinoline-1(2H),4'-piperidine]-3(4H)-one hydrochloride (30 mg) and phenyl N-(4-benzoylphenyl) carbamate (37 mg) were dissolved in dimethyl sulfoxide (2 mL) and stirred together with aqueous 10N sodium hydroxide (12 μL) at room temperature for 30 minutes. The reaction mixture was poured into water and extracted with ethyl acetate (20 mL). The organic layer was washed with water (20 mL) and saturated saline solution (20 mL), then dried over anhydrous $Na_2SO_4$ and concentrated. The residue was purified by column chromatography on silica gel (hexane/ ethyl acetate=4/1 to 1/2) and recrystallized from chloroform-acetone (1:3) to give the subject compound (81 mg) as colorless crystals (melting point 241–243° C.).

Compounds of Example 6 to 21 were obtained in the similar manner as Example 1-(6) or Example 5 by using spiro[isoquinoline-1(2H),4'-piperidine]-3(4H)-one hydrochloride and phenyl carbamate derivatives corresponding to the desired compounds.

Example 6

3,4-Dihydro-3-oxo-N-(5-phenyl-2-pyrazinyl)spiro [isoquinoline-1(2H),4'-piperidine]-1'-carboxamide melting point 237–239° C.

Example 7

3,4-Dihydro-N-(7-methyl-2-quinolyl)-3-oxospiro
[isoquinoline-1(2H),4'-piperidine]-1'-carboxamide melting point 216–218° C.

Example 8

N-(4-acetylphenyl)-3,4-dihydro-3-oxospiro
[isoquinoline-1(2H),4'-piperidine]-1'-carboxamide melting point>300° C.

Example 9

3,4-Dihydro-3-oxo-N-[1-(2-quinolyl)-4-imidazolyl]
spiro[isoquinoline-1(2H),4'-piperidine]-1'-
carboxamide melting point 264–266° C.

Example 10

3,4-Dihydro-3-oxo-N-(5-oxo-5,6,7,8-tetrahydro-2-
naphthyl)spiro[isoquinoline-1(2H),4'-piperidine]-1'-
carboxamide melting point 220.5–222.2° C.

Example 11

3,4-Dihydro-N-[5-(2-methyl-1-propenyl)-2-
pyrazinyl]-3-oxospiro[isoquinoline-1(2H),4'-
piperidine]-1'-carboxamide melting point 232.9–236.5° C.

Example 12

3,4-Dihydro-3-oxo-N-(3-phenyl-5-isoxazolyl)spiro
[isoquinoline-1(2H),4'-piperidine]1'-carboxamide melting point 239–241° C.

Example 13

N-[1-(7-benzo[b]furanyl)-4-imidazolyl]-3,4-dihydro-
3-oxospiro[isoquinoline-1(2H),4'-piperidine]-1'-
carboxamide melting point 192–194° C.

Example 14

N-[1-(3-difluoromethoxyphenyl)-4-imidazolyl]- 3,4-
dihydro-3-oxospiro[isoquinoline-1(2H),4'-
piperidine]-1'-carboxamide melting point 161–163° C.

Example 15

3,4-Dihydro-3-oxo-N-[4-(2-pyridylcarbonyl)phenyl]
spiro[isoquinoline-1(2H),4'-piperidine]-1'-
carboxamide melting point 162–164° C.

Example 16

N-(3,4-dichlorophenyl)-3,4-dihydro-3-oxospiro
[isoquinoline-1(2H),4'-piperidine]-1'-carboxamide melting point>300° C.

Example 17

N-[1-(3-chlorophenyl)-4-imidazolyl]-3,4-dihydro-3-
oxospiro[isoquinoline-1(2H),4'-piperidine]-1'-
carboxamide melting point 255–258° C.

Example 18

3,4-Dihydro-3-oxo-N-(5-phenyl-2-thiazolyl)spiro
[isoquinoline-1(2H) 4'-piperidine]- 1'-carboxamide melting point>300° C.

Example 19

3,4-Dihydro-3-oxo-N-[5-(2-pyridyl)-2-pyrazinyl]
spiro[isoquinoline-1(2H),4'-piperidine]-1'-
carboxamide melting point 223–225° C.

Example 20

3,4-Dihydro-N-(4-methyl-2-benzothiazolyl)-3-
oxospiro[isoquinoline-1(2H),4'-piperidine]-1'-
carboxamide melting point 144–146° C.

Example 21

N-(5-chloro-2-benzoxazolyl)-3,4-dihydro-3-oxospiro
[isoquinoline-1(2H),4'-piperidine]-1'-carboxamide melting point 256–258° C.

Example 22

Preparation of N-(4-benzoylphenyl)-3-oxospiro
[isobenzofuran-1(3H),4'-piperidine]-1'-carboxamide A mixture of spiro[isobenzofuran-1(3H),4'-piperidine]-3-one hydrochloride (48 mg), phenyl N-(4-benzoylphenyl) carbamate (58 mg) and triethylamine (0.14 mL) in chloroform (5 mL) was stirred at 80° C. for 2 hours. The reaction mixture was poured into water and extracted with chloroform (20 mL). The organic layer was washed with saturated saline solution (20 mL), then dried over anhydrous $Na_2SO_4$ and concentrated. The residue was purified by column chromatography on silica gel (hexane/ethyl acetate=4/1 to 1/2) and recrystallized from ethyl ether-hexane to give the subject compound (81 mg) as colorless crystals ( melting point 161–163° C.).

Example 23

Preparation of 3-oxo-N-(5-phenyl-2-pyrazinyl)-spiro
[isobenzofuran-1(3H),4'-piperidine]-1'-carboxamide (1)Preparation of phenyl N-(5-phenyl-2-pyrazinyl) carbamate Phenyl chlorocarbonate (15.05 mL) was added at 0° C. to a solution of 2-amino-5-phenylpyrazine (17.12 g) in pyridine (200 mL). The mixture was stirred at room temperature for 2 hours. To the reaction mixture was added water (200 mL) and ethyl ether (200 mL). The whole was stirred to provide a suspension containing the subject compound as a crystal. The crystal was collected by filtration and further washed with ethyl ether (50 mL) and then dried under reduced pressure to provide the subject compound (24.57 g) as colorless crystals (melting point 192–198° C., decomposed).

(2)Preparation of 3-oxo-N-(5-phenyl-2-pyrazinyl)-spiro[isobenzofuran-1(3H),4'-piperidine]-1'-carboxamide (Crystal Form A)

A mixture of spiro[isobenzofuran-1(3H),4'-piperidine]-3-one hydrochloride (6.24 g, 26.6 mmol), phenyl N-(5-phenyl-2-pyrazinyl)carbamate(7.59 g, 26.0 mmol) and triethylamine (18 mL, 180 mmol) in chloroform (200 mL) was stirred at 80° C. for 3 hours. The reaction mixture was washed with saturated aqueous sodium bicarbonate (100 mL). After the organic layer was washed with 10% citric acid aqueous solution (100 mL), 1N aqueous sodium hydroxide (100 mL) and then saturated saline solution (100 mL), the organic layer was dried over anhydrous $Na_2SO_4$ and then concentrated. The residue was purified by column chromatography on silica gel (hexane/ethyl acetate=1/2) to provide the subject compound as a colorless solid. The solid was washed with diethyl ether (30 mL) to provide the subject compound (8.23 g) as a crude crystal. The crystal was dissolved in hot ethyl acetate (300 mL). After removal of about 100 mL of ethyl acetate by distillation, the white suspension began to occur. At this point the distillation was stopped and the whole was cooled and then kept at room temperature for 14 hours. The colorless prisms formed was collected by filtration, which was washed with heptane (20 mL). The obtained crystal was dried at 50° C. in vacuo for 6 hours to provide the subject compound (Crystal Form A) (5.17 g) as colorless prisms (melting point 210–211° C.).

Powder X-ray diffraction

| 2 θ (degrees) | Intensity (cps) |
| --- | --- |
| 8.160 | 4135 |
| 9.600 | 2607 |
| 11.680 | 1372 |
| 14.620 | 194 |
| 15.320 | 1505 |
| 15.620 | 1321 |
| 15.880 | 2687 |
| 16.080 | 1711 |
| 16.420 | 3174 |
| 17.940 | 1036 |
| 19.100 | 6232 |
| 19.600 | 878 |
| 20.280 | 206 |
| 20.860 | 813 |
| 21.300 | 3360 |
| 22.020 | 328 |
| 22.740 | 1498 |
| 23.460 | 3782 |
| 23.820 | 549 |
| 24.420 | 1915 |
| 24.880 | 474 |
| 25.840 | 1329 |
| 26.360 | 515 |
| 28.480 | 433 |
| 29.260 | 248 |
| 30.860 | 692 |
| 32.140 | 246 |
| 34.300 | 112 |
| 39.160 | 163 |

Above powder X-ray diffraction analysis data were measured by RINT1100 (manufactured by Rigaku International Corporation) and analysis methods were as follows:

X-ray radiation source: Cu, tube voltage: 40 kV, tube current: 30 mA, monochromater: automatic monochromater, mono receiving slit: 0.60 mm, goniometer: Wide angle goniometer, scan step: 0.02 deg., scan speed: 2.00 deg./min., divergence slit(DS): 1 deg., scattering slit: 1 deg., receiving slit (RS): 0.15 mm, measured temperature: ambient temperature.

(3) Preparation of 3-oxo-N-(5-phenyl-2-pyrazinyl)spiro[isobenzofuran-1(3H),4'-piperidine]-1'-carboxamide (Crystal Form A)—an alternative method for preparation Crude crystals (2 g) prepared by the above procedure (2) was dissolved under heating into tetrahydrofuran (20 mL). After confirming complete dissolution, the mixture was cooled to the room temperature by standing it at room temperature. Heptane (27 mL) was dropwise added to the tetrahydrofuran solution, followed by stirring at room temperature for 15 hours. The yielded colorless crystals were collected by filtration, washed with heptane (5 mL) and dried in vacuum at 30° C. for 15 hours to obtain the above-identified compound in crystal form A (1.82 g).

(4) Preparation of 3-oxo-N-(5-phenyl-2-pyrazinyl)spiro[isobenzofuran-1(3H),4'-piperidine]-1'-carboxamide (Crystal Form B)

Crude crystals (2 g) prepared by the above procedure (2) was dissolved under heating into dimethylformamide (6 mL). After confirming complete dissolution, water (13 mL) was dropwise added at 80° C. and the resultant mixture was cooled to room temperature, followed by stirring for 15 hours. The yielded colorless crystals were collected by filtration at room temperature, washed with heptane (5 mL) and dried in vacuum for 15 hours at room temperature to obtain 1.78 g of the above-identified compound in the crystal form B as colorless prisms (melting point; 208° C. measured without correction by the use of Melting Point B-545 distributed by Buchi Company).

Powder X-ray diffraction

| 2 θ (degrees) | Intensity (cps) |
| --- | --- |
| 7.300 | 211 |
| 9.540 | 555 |
| 13.340 | 619 |
| 14.320 | 848 |
| 14.680 | 2435 |
| 15.620 | 7792 |
| 15.980 | 2307 |
| 16.400 | 6800 |
| 19.280 | 781 |
| 19.620 | 3137 |
| 19.920 | 1954 |
| 20.280 | 2234 |
| 20.900 | 4008 |
| 23.000 | 2311 |
| 24.060 | 3362 |
| 24.760 | 3598 |
| 25.300 | 953 |
| 25.880 | 3117 |
| 26.160 | 632 |
| 26.620 | 461 |
| 26.900 | 426 |
| 27.540 | 584 |
| 28.920 | 312 |
| 31.400 | 546 |
| 31.780 | 247 |
| 33.320 | 270 |
| 38.440 | 357 |
| 39.140 | 307 |
| 39.660 | 103 |

Above powder X-ray diffraction analysis data were measured by the same conditions as Example 23(2).

(5) Preparation of 3-oxo-N-(5-phenyl-2-pyrazinyl)spiro[isobenzofuran-1(3H),4'-piperidine]-1'-carboxamide (Crystal Form C)

Crude crystals (2 g) prepared by the above procedure (2) was dissolved under heating into tetrahydrofuran (20 mL). After confirming complete dissolution, the solution was cooled to −30° C. Heptane (30 mL) was dropwise added to the tetrahydrofuran solution, followed by stirring at −30° C. for one hour. The yielded colorless crystals were collected by filtration, washed with heptane (5 mL) and dried in vacuum at room temperature for 15 hours to obtain 1.90 g of the above-identified product (monotetrahydrofuran solvate, the crystal form C) as colorless fine granules.

Powder X-ray diffraction

| 2 θ (degrees) | Intensity (cps) |
| --- | --- |
| 5.940 | 1209 |
| 7.680 | 7150 |
| 11.420 | 1480 |
| 13.180 | 2032 |
| 14.240 | 1859 |
| 14.840 | 623 |
| 15.460 | 2629 |
| 16.580 | 2244 |
| 16.800 | 4076 |
| 17.960 | 706 |
| 18.640 | 2479 |
| 20.340 | 296 |
| 21.260 | 699 |
| 21.680 | 839 |
| 22.220 | 642 |
| 23.040 | 2515 |
| 24.000 | 1355 |
| 25.220 | 467 |
| 26.500 | 850 |
| 27.160 | 840 |
| 27.640 | 1078 |
| 28.780 | 389 |
| 30.940 | 283 |
| 34.200 | 267 |

Above powder X-ray diffraction analysis data were measured by the same conditions as Example 23(2).

(6) Preparation of 3-oxo-N-(5-phenyl-2-pyrazinyl)spiro[isobenzofuran-1(3H),4'-piperidine]-1'-carboxamide (Crystal Form D)

Spiro[isobenzofuran-1(3H),4'-piperidine]-3-one hydrochloride (515 mg) and phenyl N-(5-phenyl-2-pyrazinyl)carbamate (583 mg) were dissolved into dimethyl sulfoxide (2.6 mL), followed by dropwise addition of dimethylbenzylamine (0.33 mL). The temperature of the resultant mixture was raised up to 50° C., and the mixture was stirred for one hour. The reaction mixture was cooled to room temperature, and acetonitrile/water (1:2) mixture solution (7.8 mL) was dropwise added. At the time when 0.2 mL of the mixture solution was added, seed crystal was added. The resultant mixture was stirred at room temperature for 6 hours. The yielded colorless crystals were collected by filtration, washed with acetonitrile/water (1:1) and dried in vacuum at room temperature for 15 hours to obtain the above-identified compound (793 mg) as crude colorless crystals. Crude crystals (26 g) prepared by the repetition of the above procedure were suspended in water-saturated isopropyl acetate (143 mL). The mixture was seeded with seed crystal and stirred at room temperature for 18 hours. The yielded crystals were collected by filtration, washed with isopropyl acetate (20 mL) and dried in vacuum at 30° C. for 15 hours to obtain the above-identified compound in the crystal form D (25.2 g) as colorless crystals (melting point; 206° C. measured without correction by the use of Melting Point B-545 distributed by Buchi Company).

Powder X-ray diffraction

| 2 θ (degrees) | Intensity (cps) |
| --- | --- |
| 9.680 | 337 |
| 10.260 | 1796 |
| 11.480 | 1921 |
| 11.800 | 2608 |
| 12.580 | 2119 |
| 13.160 | 5843 |
| 13.900 | 1413 |
| 15.440 | 4091 |
| 15.660 | 4780 |
| 16.520 | 1853 |
| 17.520 | 298 |
| 19.320 | 1748 |
| 20.220 | 4858 |
| 20.660 | 2115 |
| 21.020 | 1063 |
| 21.480 | 493 |
| 21.820 | 856 |
| 22.280 | 947 |
| 22.700 | 2126 |
| 23.140 | 13619 |
| 23.640 | 502 |
| 24.460 | 3174 |
| 25.400 | 1919 |
| 26.060 | 1306 |
| 26.580 | 860 |
| 26.960 | 337 |
| 28.040 | 1036 |
| 28.620 | 188 |
| 29.080 | 852 |
| 30.160 | 328 |
| 30.880 | 617 |
| 31.820 | 728 |
| 37.460 | 315 |

Above powder X-ray diffraction analysis data were measured by the same conditions as Example 23(2).

(7) Preparation of 3-oxo-N-(5-phenyl-2-pyrazinyl)spiro[isobenzofuran-1(3H),4'-piperidine]-1'-carboxamide (Crystal Form B)—an alternative method for preparation Crude crystals (26 g) prepared by the above procedure (6) was suspended in acetonitrile (260 mL). The mixture was seeded with the seed crystal prepared by the above procedure (4) and stirred at room temperature for 24 hours. The yielded crystals were collected by filtration, washed with acetonitrile (50 mL) and dried in vacuum at 30° C. for 15 hours to obtain the above-identified product in the crystal form B (25.5 g).

Compounds of Example 24 to 39 were obtained in the similar manner as Example 22 by replacing phenyl N-(4-benzoylphenyl)carbamate used in Example 22 by the corresponding materials, respectively.

Example 24

N-(7-methyl-2-quinolyl)-3-oxospiro[isobenzofuran-1(3H), 4'-piperidine]-1'-carboxamide melting point 178–180° C.

Example 25

3-Oxo-N-(3-phenyl-5-isoxazolyl)-spiro[isobenzofuran-1(3H),4'-piperidine]-1'-carboxamide melting point 239–242° C.

Example 26

3-Oxo-N-(7-trifluoromethylpyrido[3,2-b]pyridin-2-yl)-spiro[isobenzofuran-1(3H),4'-piperidine]-1'-carboxamide melting point 246–248° C.

Example 27

3-Oxo-N-(5-phenyl-2-pyrimidinyl)-spiro[isobenzofuran-1(3H),4'-piperidine]-1'-carboxamide melting point 211–214° C.

Example 28

3-Oxo-N-[1-(3-quinolyl)-4-imidazolyl]spiro[isobenzofuran-1(3H),4'-piperidine]-1'-carboxamide melting point 251–254° C.

Example 29

3-Oxo-N-(5-phenyl-3-pyrazolyl)spiro[isobenzofuran-1(3H), 4'-piperidine]-1'-carboxamide melting point 160–165° C.

Example 30

N-[5-(4-chlorophenyl)-3-pyrazolyl]-3-oxospiro[isobenzofuran-1(3H),4'-piperidine]-1'-carboxamide melting point 255–258° C.

Example 31

3-oxo-N-[5-(3-quinolyl)-3-pyrazolyl]spiro[isobenzofuran-1(3H),4'-piperidine]-1'-carboxamide melting point 253–257° C.

Example 32

N-[5-(3-fluorophenyl)-2-pyrimidinyl]-3-oxospiro[isobenzofuran-1(3H),4'-piperidine]-1'-carboxamide melting point 122–125° C.
Powder X-ray diffraction

| 2 θ (degrees) | Intensity (cps) |
| --- | --- |
| 4.96 | 5335 |
| 9.94 | 2512 |
| 13.82 | 1020 |
| 14.56 | 555 |
| 14.64 | 565 |
| 14.94 | 1705 |
| 16.14 | 1067 |
| 16.66 | 2260 |
| 17.12 | 1668 |
| 17.60 | 1420 |
| 17.92 | 590 |
| 19.40 | 447 |
| 19.80 | 788 |
| 19.94 | 627 |
| 20.42 | 1057 |
| 21.00 | 963 |
| 21.80 | 1698 |
| 22.06 | 2397 |
| 22.36 | 1235 |
| 23.96 | 555 |
| 24.16 | 632 |
| 24.32 | 402 |
| 25.08 | 1603 |
| 25.38 | 538 |
| 26.82 | 647 |
| 27.06 | 1345 |
| 27.84 | 1073 |
| 28.80 | 465 |

-continued

| 2 θ (degrees) | Intensity (cps) |
| --- | --- |
| 28.86 | 493 |
| 29.42 | 752 |
| 30.30 | 1015 |
| 30.74 | 850 |
| 34.16 | 422 |
| 38.12 | 918 |
| 42.36 | 625 |
| 43.88 | 528 |

Above powder X-ray diffraction analysis data were measured by RINT2100 Ultima+ System(2 KW) (manufactured by Rigaku International Corporation) and analysis methods were as follows:

X-ray radiation source: Cu,
tube voltage: 40 kV,
tube current: 30 mA,
monochromater: automatic monochromater,
monoreceiving slit: 0.15 mm,
goniometer: Horizontal goniometer I,
scan step: 0.02 deg.,
scan speed: 2.00 deg./min.,
divergence slit(DS): 1 deg.,
scattering slit: 1 deg.,
receiving slit (RS): 0.15 mm,
measured temperature: ambient temperature.

Example 33

3-Oxo-N-[5-(3-trifluoromethylphenyl)-2-pyrimidinyl)spiro[isobenzofuran-1(3H),4'-piperidine]-1'-carboxamide melting point 190–192° C.

Example 34

N-[5-(3-chlorophenyl)-2-pyrimidinyl]-3-oxospiro[isobenzofuran-1(3H),4'-piperidine]-1'-carboxamide melting point 126–128° C.

Example 35

N-(7-difluoromethoxypyrido[3,2-b]pyridin-2-yl)-3-oxospiro[isobenzofuran-1(3H),4'-piperidine]-1'-carboxamide melting point 193° C.

Example 36

3-Oxo-N-(5-phenyl-1,2,4-thiadiazol-3-yl)spiro[isobenzofuran-1(3H),4'-piperidine]-1'-carboxamide melting point 239–241° C.

Example 37

N-{1-[3-(2-hydroxyethyl)phenyl]-4-imidazolyl}-3-oxospiro[isobenzofuran-1(3H),4'-piperidine]-1'-carboxamide melting point 99–100° C.

Example 38

N-[4-(1-ethyl-2-imidazolyl)phenyl]-3-oxospiro[isobenzofuran-1(3H),4'-piperidine]-1'-carboxamide melting point 221–223° C.

Example 39

N-[1-(3-methoxyphenyl)-4-imidazolyl]-3-oxospiro [isobenzofuran-1(3H),4'-piperidine]-1'-carboxamide melting point 208–210° C.

Example 40

Preparation of 6-fluoro-3-oxo-N-(5-phenyl-2-pyrazinyl)spiro-[isobenzofuran-1(3H),4'-piperidine]-1'-carboxamide A mixture of 6-fluorospiro[isobenzofuran-1(3H),4'-piperidine]-3-one hydrochloride (64 mg), phenyl N-(5-phenyl-2-pyrazinyl)carbamate (73 mg) and triethylamine (174 µL) in chloroform (5 mL) was stirred at 80° C. for 2 hours. The reaction mixture was poured into water and extracted with chloroform (20 mL). The organic layer was washed with saturated saline solution (20 mL), then dried over anhydrous $Na_2SO_4$ and concentrated. The residue was purified by column chromatography on silica gel (hexane/ethyl acetate=4/1 to 1/2) and recrystallized from ethyl ether-hexane to give the subject compound (101 mg) as colorless crystals (melting point 222–224° C.).

Example 41

Preparation of 6-fluoro-3-oxo-N-(5-phenyl-2-pyrimidinyl)spiro[iso-benzofuran-1(3H),4'-piperidine]-1'-carboxamide The subject compound was obtained in the similar manner as Example 40 by replacing phenyl N-(5-phenyl-2-pyrazinyl)carbamate used in Example 40 by phenyl N-(5-phenyl-2-pyrimidinyl)carbamate.

melting point 176–178° C.

Example 42

Preparation of 5-fluoro-3-oxo-N-(5-phenyl-2-pyrazinyl)spiro[isobenzo-furan-1(3H),4'-piperidine]-1'-carboxamide A mixture of 5-fluorospiro[isobenzofuran-1(3H),4'-piperidine]-3-one hydrochloride (64 mg), phenyl N-(5-phenyl-2-pyrazinyl)carbamate (73 mg) and triethylamine (174 µL) in chloroform (5 mL) was stirred at 80° C. for 2 hours. The reaction mixture was poured into water and extracted with chloroform (20 mL). The organic layer was washed with saturated saline solution (20 mL), then dried over anhydrous $Na_2SO_4$ and concentrated. The residue was purified by column chromatography on silica gel (hexane/ethyl acetate=4/1 to 1/2) and recrystallized from ethyl ether-hexane to give the subject compound (100 mg) as colorless crystals (melting point 236–238° C.).

Example 43

Preparation of 5-fluoro-3-oxo-N-(5-phenyl-2-pyrimidinyl)spiro[iso-benzofuran-1(3H),4'-piperidine]-1'-carboxamide The subject compound was obtained in the similar manner as Example 42 by replacing phenyl N-(5-phenyl-2-pyrazinyl)carbamate used in Example 42 by phenyl N-(5-phenyl-2-pyrimidinyl)carbamate.

melting point 255–257° C.

Example 44

Preparation of N-(4-benzoylphenyl)-3,4-dihydro-3-oxospiro[1H-2-benzopyran-1,4'-piperidine]-1'-carboxamide Spiro[1H-2-benzopyran-1,4'-piperidine]-3(4H)-one hydrochloride (50.6 mg) and phenyl N-(4-benzoylphenyl) carbamate (63.4 mg) were suspended in dimethyl sulfoxide (1.0 mL) and the suspension was vigorously stirred together with aqueous 10M sodium hydroxide (30 µL) for 5 minutes. The reaction mixture was diluted with water and extracted with ethyl acetate. The organic layer was washed with saturated saline solution, then dried over anhydrous $Na_2SO_4$ and concentrated. The residue was crystallized from methanol-diisopropyl ether to give the subject compound (68.0 mg) as colorless crystals (melting point 138–146° C.).

Compounds of Example 45 and 46 were obtained in the similar manner as Example 44 by replacing phenyl N-(4-benzoylphenyl)carbamate used in Example 44 by the corresponding materials, respectively.

Example 45

3,4-Dihydro-3-oxo-N-(5-phenyl-2-pyrazinyl)spiro [1H-2-benzopyran-1,4'-piperidine]-1'-carboxamide melting point 221° C.

Example 46

N-(5-benzoyl-2-pyrazinyl)-3,4-dihydro-3-oxospiro [1H-2-benzopyran-1,4'-piperidine]-1'-carboxamide melting point 128–131° C.

Example 47

Preparation of trans-N-(4-benzoylphenyl)-3'-oxospiro[cyclohexane-1,1'(3'H)-isobenzofuran]-4-carboxamide (1) Preparation of spiro[cyclohexane-1,1'(3'H)-isobenzofuran]-3',4-dione A solution of 2-bromobenzoic acid (4.77 g) in anhydrous tetrahydrofuran (100 mL) was cooled to −78° C. under an atmosphere of nitrogen, to which n-butyllithium (1.53M solution in hexane, 31 mL) was dropwise added while being kept the internal temperature below −55° C. After being stirred for 1 hour, a solution of 1,4-cyclohexanedione mono-ethylene ketal (5.18 g) in anhydrous tetrahydrofuran (10 mL) was added dropwise to the mixture while being kept the internal temperature below −67° C. After the temperature was raised to room temperature, the reaction solution was partitioned between water (150 mL) and hexane (100 mL). The aqueous layer was acidified with concentrated hydrochloric acid and refluxed together with acetone (10 mL) for 2 hours. After cooling, thus obtained mixture was neutralized with potassium carbonate and extracted with ethyl acetate. The organic layer was washed with saturated saline solution, then dried over anhydrous $Na_2SO_4$ and evaporated. The residue was crystallized from ethyl acetate-hexane to give the subject compound (2.42 g).

(2) Preparation of 4-methylenespiro[cyclohexane-1,1'(3'H)-isobenzofuran]-3-one

A suspension of methyltriphenylphosphonium bromide (715 mg) in anhydrous tetrahydrofuran (7.0 mL) was cooled to 0° C. under an atmosphere of nitrogen, to which n-butyllithium (1.53M solution in hexane, 1.3 mL) was added, stirred at that temperature for 20 minutes and then cooled to −78° C. A solution of spiro[cyclohexane-1,1'(3'H)-isobenzofuran]-3',4-dione (216 mg) in anhydrous tetrahydrofuran (3 mL) was added to the reaction mixture and the temperature was raised to 0° C. After stirring for 20 minutes, aqueous ammonium chloride was added to thus obtained mixture and the resulting crude product was extracted with ethyl acetate. The organic layer was washed with saturated saline solution, then dried over anhydrous $Na_2SO_4$ and concentrated. The residue was purified by column chromatography on silica gel (hexane/ethyl acetate=4/1) to give the subject compound (196 mg).

(3) Preparation of 4-hydroxymethylspiro[cyclohexane-1,1'(3'H)-isobenzofuran]-3'-one A solution of 4-methylenespiro[cyclohexane-1,1'(3'H)-isobenzofuran]-3-one (196 mg) in anhydrous tetrahydrofuran (5.0 mL) was cooled to 0° C., to which borane-dimethyl sulfide complex (2M tetrahydrofuran solution, 690 µL) was added and the mixture was stirred at that temperature for 1.5 hours, then additional 20 minutes together with aqueous 2M sodium hydroxide (5.0 mL) and aqueous 30% hydroperoxide (5.0 mL). The reaction mixture was diluted with water, extracted with ethyl acetate, washed with saturated saline solution, then dried over anhydrous $Na_2SO_4$ and evaporated. The residue was purified by column chromatography on silica gel (hexane/ethyl acetate=2/1) to give the subject compound (190 mg) as diastereomers.

(4) Preparation of trans-3'-oxospiro[cyclohexane-1,1'(3'H)-isobenzofuran]-4-carboxylic acid A mixture of 4-hydroxymethylspiro[cyclohexane-1,1'(3'H)-isobenzofuran]-3'-one (190 mg), chloroform (2.0 mL), acetonitrile (2.0 mL) and sodium phosphate buffer (pH6.5, 2.0 mL) was cooled to 0° C., to which sodium periodate (612 mg) and ruthenium(III) chloride n-hydrate (10 mg) were added and the mixture was stirred for 30 minutes. The reaction mixture was stirred together with 1N hydrochloric acid (2.0 mL) for 30 minutes and partitioned between water (50 mL) and ethyl acetate (50 mL). The organic layer was washed with saturated saline solution, dried over anhydrous $Na_2SO_4$ and then concentrated. The residue was purified by column chromatography on silica gel (chloroform/methanol=100/1) to give the subject compound (98.6 mg).

(5) Preparation of trans-N-(4-benzoylphenyl)-3'-oxospiro[cyclohexane-1,1'(3'H)-isobenzofuran]-4-carboxamide To a solution of trans-3'-oxospiro[cyclohexane-1,1'(3'H)-isobenzofuran]-4-carboxylic acid (24.6 mg) in pyridine (500 µL), 4-aminobenzophenone (19.8 mg) and 1-(3-dimethylaminopropyl)-3-ethylcarbodiimide hydrochloride (57.5 mg) were added and the mixture was stirred at 50° C. for 2 hours. The reaction mixture was partitioned between water and ethyl acetate. The organic layer was washed with aqueous potassium hydrogen sulfate, aqueous sodium hydrogen carbonate, and saturated saline solution and then dried over anhydrous $Na_2SO_4$ and evaporated. The residue was crystallized from ethyl acetate-hexane to give the subject compound (31.2 mg) as colorless crystals (melting point 194° C.).

Compounds of Example 48 to 56 were obtained in the similar manner as Example 47-(5) by replacing 4-aminobenzophenone used in Example 47-(5) by the corresponding materials, respectively.

Example 48

Trans-3'-oxo-N-(5-phenyl-2-pyrazinyl)spiro[cyclohexane-1,1'(3'H)-isobenzofuran]-4-carboxamide melting point 223° C.

Example 49

Trans-3'-oxo-N-(1-phenyl-4-imidazolyl)spiro[cyclohexane-1,1'(3'H)-isobenzofuran]-4-carboxamide melting point 264° C.

Example 50

Trans-3'-oxo-N-(5-phenyl-2-pyrimidinyl)spiro[cyclohexane-1,1'(3'H)-isobenzofuran]-4-carboxamide melting point 184° C.

Example 51

Trans-N-[1-(3,5-difluorophenyl)-4-imidazolyl]-3'-oxospiro[cyclohexane-1,1'(3'H)-isobenzofuran]-4-carboxamide melting point 294° C.

Example 52

Trans-3'-oxo-N-(5-phenyl-3-pyrazolyl)spiro[cyclohexane-1,1'(3'H)-isobenzofuran]-4-carboxamide melting point 238° C.

Example 53

Trans-N-[1-(2-fluorophenyl)-4-imidazolyl]-3'-oxospiro[cyclohexane-1,1'(3'H)-isobenzofuran]-4-carboxamide melting point 258° C.

Example 54

Trans-N-1(4-acetyl-3-trifluoromethylphenyl)- 3'-oxospiro[cyclohexane-1,1'(3'H)-isobenzofuran]-4-carboxamide melting point 274–275° C.

Example 55

Trans-3'-oxo-N-[1-(3-quinolyl)-4-imidazolyl]spiro[cyclohexane-1,1'(3'H)-isobenzofuran]-4-carboxamide melting point>300° C.

Example 56

Trans-N-[1-(3-cyanophenyl)-4-imidazolyl]-3'-oxospiro[cyclohexane-1,1'(3'H)-isobenzofuran]-4-carboxamide melting point 268–270° C.

Example 57

Preparation of trans-N-(4-benzoylphenyl)-3-oxospiro[4-azaisobenzofuran-1(3H),1'-cyclohexane]-4'-carboxamide (1) Preparation of dispiro[4-azaisobenzofuran-1(3H),1'-cyclohexane-4',2"-1",3"-dioxolane]-3-one A solution of N-methyl-2-pyridinecarboxamide (9.53 g) in anhydrous tetrahydrofuran (400 mL) was cooled to −78° C. under an atmosphere of nitrogen, to which n-butyllithium (1.54M solution in hexane, 100 mL) was dropwise added. After being stirred for 1.5 hours at the some temperature, a solution of 1,4-cyclohexanedione monoethylene ketal (10.93 g) in anhydrous tetrahydrofuran (100 mL) was added dropwise to the mixture. After the temperature was raised to room temperature, the reaction mixture was partitioned between water (300 mL) and ethyl ether (100 mL). The aqueous layer was acidified with 2N hydrochloric acid, stirred for 30 minutes, neutralized with potassium carbonate and then left overnight. The resulting precipitate was collected by filtration and dried to give the subject compound (6.84 g).

(2) Preparation of spiro[4-azaisobenzofuran-1(3H),1'-cyclohexane]-3,4'-dione

A mixture of dispiro[4-azaisobenzofuran-1(3H),1'-cyclohexane-4',2"-1",3"-dioxolane]-3-one (6.8 g), 2N hydrochloric acid (20 mL) and acetone (5 mL) was heated under reflux for 13 hours. After cooling, the mixture was neutralized with potassium carbonate and stirred together with isopropyl ether (5 mL) for 3 hours. The resulting precipitate was collected by filtration, washed with water and isopropyl ether and then dried to give the subject compound (3.39 g).

(3) Preparation of cis-4'-hydroxyspiro[4-azaisobenzofuran-1(3H),1'-cyclohexane]-3-one Spiro[4-azaisobenzofuran-1(3H),1'-cyclohexane]-3,4'-dione (5.7 g) was dissolved in tetrahydrofuran (50 mL) and water (10 mL) and cooled to 0° C. The solution was stirred together with sodium borohydride (993 mg) for 20 minutes, acidified with 10% sulfuric acid, adjusted to pH7.4 with saturated sodium hydrogen carbonate aqueous solution and extracted with chloroform-ethanol and chloroform-tetrahydrofuran. The organic layer was dried over anhydrous $Na_2SO_4$ and concentrated. The residue was crystallized from ethyl acetate-isopropyl ether to give the subject compound (2.02 g).

(4) Preparation of trans-3-oxospiro[4-azaisobenzofuran-1(3H),1'-cyclohexane]-4'-carbonitrile To a solution of cis-4'-hydroxyspiro[4-azaisobenzofuran-1(3H),1'-cyclohexane]-3-one (2.02 g) in anhydrous tetrahydrofuran (60 mL), triethylamine (3.08 mL) was added and cooled to 0° C. Methanesulfonyl chloride (1.3 mL) was added dropwise to the mixture and stirred at that temperature for 1 hour. The reaction mixture was diluted with water and extracted with chloroform. The organic layer was dried over anhydrous $Na_2SO_4$ and evaporated. The residue was crystallized from ethyl acetate-isopropyl ether to give mesylate (2.47 g). Thus obtained mesylate was dissolved in dimethylformamide (25 mL) and stirred together with tetraethylammonium cyanide (3.25 g) at 100° C. for 3 hours. After cooling, the reaction mixture was diluted with water and extracted with ethyl acetate. The organic layer was washed with water and saturated saline solution, dried over anhydrous $Na_2SO_4$ and then concentrated. The residue was purified by column chromatography on silica gel (hexane/ethyl acetate=2/3) to give the subject compound (1.0 g).

(5) Preparation of trans-3-oxospiro[4-azaisobenzofuran-1(3H),1'-cyclohexane]-4'-carboxylic acid A solution of trans-3-oxospiro[4-azaisobenzofuran-1(3H),1'-cyclohexane]-4'-carbonitrile (1.0 g) in 30% sulfuric acid was heated under reflux for 11 hours. After cooling, the reaction mixture was diluted with water and adjusted to pH6 with potassium carbonate. The resulting precipitate was collected by filtration, washed with water and air-dried to give the subject compound (974 mg).

(6) Preparation of trans-N-(4-benzoylphenyl)-3-oxospiro[4-azaisobenzofuran-1(3H),1'-cyclohexane]-4'-carboxamide To a solution of trans-3-oxospiro[4-azaisobenzofuran-1(3H),1'-cyclohexane]-4'-carboxylic acid (66 mg) in pyridine (1 mL), 4-aminobenzophenone (52.6 mg) and 1-(3-dimethylaminopropyl)-3-ethylcarbodiimide hydrochloride (153 mg) were added and the mixture was stirred at 40° C. for 2 hours. The reaction mixture was concentrated and the residue was partitioned between water and ethyl acetate. The organic layer was washed with saturated saline solution, dried over anhydrous $Na_2SO_4$ and then concentrated. The residue was crystallized from ethyl acetate-hexane to give the subject compound (94.4 mg) as colorless crystals (melting point 237° C.).

Compounds of Example 58 to 60 were obtained in the similar manner as Example 57-(6) by replacing 4-aminobenzophenone used in Example 57-(6) by the corresponding materials, respectively.

Example 58

Trans-3-oxo-N-(5-phenyl-2-pyrazinyl)spiro[4-azaisobenzofuran-1(3H),1'-cyclohexane]-4'-carboxamide melting point 203° C.

Example 59

Trans-3-oxo-N-(3-phenyl-5-isoxazolyl)spiro[4-azaisobenzofuran-1(3H),1'-cyclohexane]-4'-carboxamide melting point 217° C.

Example 60

Trans-3-oxo-N-(5-phenyl-2-pyrimidinyl)spiro[4-azaisobenzofuran-1(3H),1'-cyclohexane]-4'-carboxamide melting point 237° C.

Example 61

Preparation of trans-N-(4-benzoylphenyl)-3-oxospiro[5-azaisobenzofuran-1(3H),1'-cyclohexane]-4'-carboxamide (1) Preparation of dispiro[5-azaisobenzofuran-1(3H),1'-cyclohexane-4',2"-1",3"-dioxolane]-3-one 2,2,6,6-Tetramethylpiperidine (41.1 mL) was dissolved in anhydrous tetrahydrofuran (400 mL) and cooled to −50° C., to which n-butyllithium (1.50M solution in hexane, 217 mL) and nicotinic acid (10.0 g) were added successively. After being stirred at −50° C. for 1 hour, a solution of 1,4-cyclohexanedione monoethylene ketal (13.9 g) in anhydrous tetrahydrofuran (25 mL) was added and then the mixture was stirred at −50° C. for 1 hour. After the temperature was raised to room temperature, the reaction mixture was poured into water (800 mL) and extracted with hexane-ether (1:1, 500 mL). The aqueous layer was adjusted to pH3 with 6N hydrochloric acid and stirred at room temperature for 2 hours. The resulting precipitate was collected by filtration and washed with water. Thus obtained solid was dissolved in chloroform (300 mL), washed with saturated sodium bicarbonate aqueous solution (150 mL), dried and then concentrated. The residue was recrystallized from ethyl acetate-hexane to give the subject compound (4.29 g).

(2) Preparation of spiro[5-azaisobenzofuran-1(3H),1'-cyclohexane]-3,4'-dione

Dispiro[5-azaisobenzofuran-1(3H),1'-cyclohexane-4',2"-1",3"-dioxolane]-3-one (4.29 g) and p-toluenesulfonic acid monohydrate (3.74 g) were dissolved in acetone (80 mL) and water (8 mL) and the solution was heated under ref lux for 3 hours. After cooling, acetone was evaporated off and chloroform (100 mL) was added to the residue. The mixture was washed with saturated sodium bicarbonate aqueous solution (50 mL×2), dried over anhydrous $Na_2SO_4$ and then evaporated. The resulting crystals were recrystallized from ethyl acetate-hexane to give the subject compound (2.68 g).

(3) Preparation of cis-4'-hydroxyspiro[5-azaisobenzofuran-1(3H),1'-cyclohexane]-3-one A suspension of spiro[5-azaisobenzofuran-1(3H),1'-cyclohexane]-3,4'-dione (167 mg) in tetrahydrofuran-water (10:1, 4 mL) was cooled to 0° C. and stirred together with sodium borohydride (32 mg) at 0° C. for 30 minutes. The reaction mixture was poured into water (5 mL), stirred at room temperature for 30 minutes and then extracted with chloroform (20 mL×3). The extract was dried over anhydrous $Na_2SO_4$ and concentrated. The residue was recrystallized from ethyl acetate-hexane to give the subject compound (77.7 mg).

(4) Preparation of trans-3-oxospiro[5-azaisobenzofuran-1(3H),1'- cyclohexane]-4'-carbonitrile A solution of cis-4'-hydroxyspiro[5-azaisobenzofuran-1(3H),1'-cyclohexane]-3-one (1.31 g) and triethylamine (1.17 mL) in anhydrous tetrahydrofuran (20 mL) was cooled to 0° C. and stirred together with methanesulfonyl chloride (0.555 mL) at 0° C. for 1 hour. The reaction mixture was poured into water (50 mL), extracted with ethyl acetate (100 mL×2), dried over anhydrous $Na_2SO_4$ and concentrated to give crude mesylate (1.87 g). The mesylate was dissolved in anhydrous dimethylformamide (30 mL) and stirred together with triethylammonium cyanide (2.98 g) at 100° C. for 5 hours. The reaction mixture was poured into water (100 mL) and extracted with ether (150 mL×3), and ether-ethyl acetate (2:1, 200 mL). The combined extracts were dried over anhydrous $Na_2SO_4$ and concentrated. The resulting oily residue was purified by column chromatography on silica gel (hexane/ethyl acetate/methanol=2/1/0 to 1/1/0 to 30/30/1) and the obtained solid was recrystallized from ethyl acetate-hexane to give the subject compound (631 mg).

(5) Preparation of trans-3-oxospiro[5-azaisobenzofuran-1(3H),1'- cyclohexane]-4'-carboxylic acid A mixture of trans-3-oxospiro[5-azaisobenzofuran-1(3H),1'-cyclohexane]-4'-carbonitrile (100 mg), water (0.7 mL) and concentrated sulfuric acid (0.3 mL) was refluxed for 11 hours. The reaction mixture was cooled to room temperature and adjusted to pH4 with aqueous 4N sodium hydroxide. The resulting precipitate was collected by filtration, washed successively with water, ethanol and diisopropyl ether and then dried to give the subject compound (78 mg).

$^1$H-NMR (200 MHz, DMSO-$d_6$, δ ppm): 1.63–1.87 (2H, m), 1.88–2.20 (6H, m), 2.70 (1H, m), 7.76 (1H, dd, J=5.2, 1.1 Hz), 8.86 (1H, d, J=5.2 Hz), 9.06 (1H, d, J=1.1 Hz).

(6) Preparation of trans-N-(4-benzoylphenyl)-3-oxospiro[5-azaisobenzofuran-1(3H),1'-cyclohexane]-4'-carboxamide A solution of trans-3-oxospiro[5-azaisobenzofuran-1(3H),1'-cyclohexane]-4'-carboxylic acid (20 mg) and 4-aminobenzophenone (16 mg) in anhydrous pyridine (0.5 mL) was stirred together with 1-(3-dimethylaminopropyl)-3-ethylcarbodiimide hydrochloride (20 mg) at 60° C. for 2 hours. The reaction mixture was poured into water (10 mL) and extracted with ethyl acetate (30 mL ×2). The combined organic layers were dried over anhydrous $Na_2SO_4$ and concentrated. The resulting oily residue was purified by column chromatography on silica gel (hexane/ethyl acetate= 1/1 to 1/2) and the obtained solid was recrystallized from ethyl acetate-hexane to give the subject compound (10 mg) as colorless crystals (melting point 256–257° C.).

Example 62

Preparation of trans-N-(4-benzoylphenyl)-3-oxospiro[6-azaisobenzofuran-1(3H),1'-cyclohexane]-4'-carboxamide (1) Preparation of dispiro[6-azaisobenzofuran-1(3H),1'-cyclohexane-4',2"-1",3"-dioxolane]-3-one 2,2,6,6-Tetramethylpiperidine (50 mL) was dissolved in anhydrous tetrahydrofuran (500 mL) and the solution was cooled to –50° C., to which n-butyllithium (1.50M solution in hexane, 270.7 mL) and isonicotinic acid (12.5 g) were added successively. The reaction mixture was stirred at –50° C. for 10 minutes and the temperature was raised to 25° C. over 30 minutes. The reaction mixture was further stirred at 25° C. for 10 minutes and then cooled to –65° C. 1,4-Cyclohexanedione monoethylene ketal (19 g) was added and the reaction mixture was stirred at –65° C. for 10 minutes. The temperature of the reaction mixture was raised to –15° C. over 1 hour, then to 0° C. over 30 minutes. Then the mixture was poured into water (300 mL), from which the aqueous layer was separated. The organic layer was extracted with aqueous 2N sodium hydroxide. The combined aqueous layers were adjusted to pH3 with concentrated hydrochloric acid and extracted with ethyl acetate (500 mL). The organic layer was washed with saturated aqueous sodium bicarbonate (200 mL), and saturated saline solution, then dried over anhydrous $MgSO_4$ and concentrated. The residue was purified by column chromatography on silica gel (hexane/ethyl acetate=1/0 to 4/1 to 3/2) and recrystallized from ethyl acetate-hexane to give the subject compound (7.20 g).

(2) Preparation of spiro[6-azaisobenzofuran-1(3H),1'-cyclohexane]-3,4'-dione

Dispiro[6-azaisobenzofuran-1(3H),1'-cyclohexane-4',2"-1",3"-dioxolane]-3-one (7.20 g) and p-toluenesulfonic acid monohydrate (5.80 g) were dissolved in acetone (150 mL) and water (15 mL) and the solution was heated under reflux for 5.5 hours. After cooling, acetone was evaporated off and the residue was extracted with ethyl acetate (100 mL×3). The combined organic layers were washed with saturated saline solution (50 mL), dried over anhydrous $MgSO_4$ and then evaporated. The resulting crystals were recrystallized from ethyl acetate-diisopropyl ether to give the subject compound (1.96 g).

(3) Preparation of cis-4'-hydroxyspiro[6-azaisobenzofuran-1(3H),1'-cyclohexane]-3-one A solution of spiro[6-azaisobenzofuran-1(3H),1'-cyclohexane]-3,4'-dione (1.0 g) in ethanol (100 mL) was cooled to 0° C. and stirred together with sodium borohydride (174 mg) at 0° C. for 1 hour. The reaction mixture was adjusted to pH4 with 10% sulfuric acid, rendered basic with aqueous saturated sodium bicarbonate and then extracted with chloroform (200 mL×2). The extract was dried over anhydrous $MgSO_4$ and concentrated. The residue was recrystallized from ethyl acetate-hexane to give the subject compound (954.5 mg).

(4) Preparation of trans-3-oxospiro[6-azaisobenzofuran-1(3H),1'-cyclohexane]-4'-carbonitrile A solution of cis-4'-hydroxyspiro[6-azaisobenzofuran-1(3H),1'-cyclohexane]-3-one (954 mg) and triethylamine (0.91 mL) in dimethylformamide (10 mL) was cooled to 0° C. and stirred together with methanesulfonyl chloride (0.40 mL) at 0° C. for 1 hour. The reaction mixture was diluted with ethyl acetate (100 mL), washed with aqueous saturated sodium bicarbonate (50 mL×2), and saturated saline solution (50 mL), then dried over anhydrous $MgSO_4$ and concentrated. The residue was recrystallized from ethyl acetate-diisopropyl ether to give mesylate (995 mg). This mesylate was dissolved in anhydrous dimethylformamide (30 mL) and stirred together with triethylammonium cyanide (1.57 g) at 100° C. for 1.5 hours. The reaction mixture was diluted with ethyl acetate (200 mL) and washed successively with water (200 mL), aqueous saturated sodium bicarbonate (200 mL), and saturated saline solution (100 mL). The organic layer was dried over anhydrous $MgSO_4$ and concentrated. The residue was recrystallized from ethyl acetate-diisopropyl ether to give the subject compound (447 mg).

(5) Preparation of trans-3-oxospiro[6-azaisobenzofuran-1(3H),1'-cyclohexane]-4'-carboxylic acid A mixture of trans-3-oxospiro[6-azaisobenzofuran-1(3H), 1'-cyclohexane]-4'-carbonitrile (445 mg), water (3.5 mL) and concentrated sulfuric acid (1.5 mL) was refluxed for 6 hours. The reaction mixture was cooled to room temperature and adjusted to pH8 with aqueous 5N sodium hydroxide, then to pH4 with concentrated hydrochloric acid. The resulting crystals were collected by filtration, washed with water and dried to give the subject compound (416 mg) as colorless crystals (melting point 222–223° C.).

$^1$H-NMR (300 MHz, DMSO-d$_6$, δ ppm): 1.7–2.2 (6H, m), 2.65–2.75 (1H, m), 7.83 (1H, dd, J=1.2 Hz, 4.9 Hz), 8.86 (1H, d, J=4.9 Hz), 9.05 (1H, d, J=1.2 Hz), 12.3 (1H, brs).

(6) Preparation of trans-N-(4-benzoylphenyl)-3-oxospiro[6-azaisobenzofuran-1(3H),1'-cyclohexane]-4'-carboxamide A solution of trans-3-oxospiro[6-azaisobenzofuran-1(3H),1'-cyclohexane]-4'-carboxylic acid (50 mg) and 4-aminobenzophenone (51.6 mg) in anhydrous pyridine (1 mL) was stirred together with 1-(3-dimethylaminopropyl)-3-ethylcarbodiimide hydrochloride (48.7 mg) at 60° C. for 2 hours. The reaction mixture was diluted with ethyl acetate (20 mL) and washed successively with water (20 mL), 10% citric acid aqueous solution (20 mL×2), aqueous saturated sodium bicarbonate, and saturated saline solution. The organic layer was dried over anhydrous MgSO$_4$ and concentrated. The resulting oily residue was purified by column chromatography on silica gel (hexane/ethyl acetate=3/2 to 1/4) and the obtained solid was recrystallized from ethyl acetate-hexane to give the subject compound (62.7 mg) as colorless crystals (melting point 147–149° C.).

Example 63

Preparation of N-[5-(4-hydroxyphenyl)-2-pyrazinyl]-3-oxospiro[isobenzofuran-1(3H),4'-piperidine]-1'-carboxamide (1) Preparation of 2-amino-5-(4-hydroxyphenyl)pyrazine To a solution of 2-amino-5-bromopyrazine (366 mg) in dimethoxyethane (20 mL) was added 4-hydroxyphenylboronic acid (320 mL), 1.5N sodium carbonate aqueous solution (2.5 mL) and tetrakis(triphenylphosphine) palladium (0) (54 mg). The mixture was stirred at 80° C. for 3 hours. To the reaction mixture was added water (20 mL) and the whole was extracted with ethyl acetate (50 mL×3). The extract was washed with saturated saline solution, then dried over anhydrous Na$_2$SO$_4$. The removal of the solvent provided crystal residue, which was washed with diethyl ether (10 mL) to give the subject compound (305 mg).

(2) Preparation of phenyl N-[5-(4-hydroxyphenyl)-2-pyrazinyl]carbamate

To solution of 2-amino-5-(4-hydroxyphenyl)pyrazine (283 mg) in pyridine (20 mL) was added under ice-cooling phenyl chloroformate (199 μL) and the mixture was stirred for 1 hour. The reaction mixture was poured into water (30 mL) and extracted with ethyl acetate (20 mL×3). The organic layer was washed with saturated saline solution and then dried over anhydrous Na$_2$SO$_4$. The concentration of the solvent left a crystal residue, which was washed with diethyl ether (10 mL) to give the subject compound (314 mg).

(3) Preparation of N-[5-(4-hydroxyphenyl)-2-pyrazinyl]-3-oxospiro[isobenzofuran-1(3H),4'-piperidine]-1'-carboxamide A mixture of spiro[isobenzofuran-1(3H),4'-piperidine]-3-one hydrochloride (96 mg), phenyl N-5-[(4-hydroxyphenyl)-2-pyrazinyl]carbamate (128 mg) and triethylamine (279 μL) in chloroform (5 mL) was stirred at 80° C. for 2 hours.

The reaction mixture was poured into water and extracted with chloroform (20 mL). The organic layer was washed with saturated saline solution (20 mL) and then dried over anhydrous Na$_2$SO$_4$.

The concentration of the solvent left a residue, which was purified by column chromatography on silica gel (hexane/ethyl acetate=4/1 to 1/2) followed by recrystallization from ethyl ether-hexane to give the subject compound (114 mg) as colorless crystals (melting point 263–265° C.).

Example 64

Preparation of N-[5-(3-hydroxyphenyl)-2-pyrazinyl]-3-oxospiro[isobenzofuran-1(3H),4'-piperidine]-1'-carboxamide (1) Preparation of 2-amino-5-(3-methoxyphenyl)pyrazine To a solution of 2-amino-5-bromopyrazine (642 mg) in dimethoxyethane (40 mL) was added 3-methoxyphenylboronic acid (560 mg), 1.5N aqueous sodium carbonate solution (4 mL) and tetrakis(triphenylphosphine) palladium (0) (86 mg). The mixture was stirred at 80° C. for 6 hours. To the reaction mixture was added water (20 mL) and the whole was extracted with ethyl acetate (50 mL×3). The extract was washed with saturated saline solution and then dried over anhydrous Na$_2$SO$_4$. The concentration of the solvent left a crystal residue, which was washed with ethyl ether (10 mL) to give the subject compound (760 mg).

(2) Preparation of 2-amino-5-(3-hydroxyphenyl)pyrazine 2-amino-5-(3-methoxyphenyl)pyrazine (566 mg) was dissolved in methylene chloride (10 mL). To this mixture was added under ice-cooling boron tribromide (530 μL) and the whole was stirred at room temperature for 14 hours. To the reaction mixture was added 1N aqueous sodium hydroxide. The whole was extracted with ethyl acetate (30 mL×2). The organic layer was washed with saturated saline solution and then dried over anhydrous Na$_2$SO$_4$. The concentration of the solvent provides the subject compound (94 mg) as a yellow solid.

(3) Preparation of Phenyl N-[5-(3-hydroxyphenyl)-2-pyrazinyl]carbamate

To a solution of 2-amino-5-(3-hydroxyphenyl)pyrazine (89 mg) in pyridine (10 mL) was added under ice-cooling phenyl chloroformate (63 μL). The mixture was stirred for 1 hour and then poured into water (30 mL) and extracted with ethyl acetate (20 mL×3). The extract was washed with saturated saline solution and then dried over anhydrous Na$_2$SO$_4$. The concentration of the solvent left a crystal residue, which was washed with ethyl ether (10 mL) to give the subject compound (51 mg).

(4) Preparation of N-[5-(3-hydroxyphenyl)-2-pyrazinyl]-3-oxospiro[isobenzofuran-1(3H),4'-piperidine]-1'-carboxamide A mixture of spiro[isobenzofuran-1(3H),4'-piperidine]-3-one hydrochloride (40 mg), phenyl N-[5-(3-hydroxyphenyl)-2-pyrazinyl]carbamate (51 mg) and triethylamine (119 μL) in chloroform (5 mL) was stirred at 80° C. for 2 hours. The reaction mixture was poured into water and extracted with chloroform (20 mL). The organic layer was washed with saturated saline solution (20 mL) and then dried over anhydrous Na$_2$SO$_4$. The concentration of the solvent left a residue, which was purified by column chromatography on silica gel (hexane/ethyl acetate=4/1 to 1/2) followed by recrystallization from ethyl ether-hexane to give the subject compound (24 mg) as colorless crystals (melting point 257–259° C.).

Example 65

Preparation of 4-fluoro-3-oxo-N-(5-phenyl-2-pyrimidinyl)spiro[isobenzofuran-1(3H),4'-piperidine]-1-carboxamide A mixture of 4-fluorospiro[isobenzofuran-1(3H),4'-piperidine]-3-one hydrochloride (150 mg), phenyl N-(5- phenyl-2-pyrimidinyl)carbamate (170 mg) and triethylamine (0.24 mL) in chloroform (2 mL) was stirred at 60° C. for 3 hours. The concentration of the reaction mixture left a residue, which was purified by column chromatography on silica gel (hexane/ethyl acetate/methanol=1/1/0~8/8/1~6/6/1) followed by recrystallization from ethyl acetate-hexane to give the subject compound (190 mg) as colorless crystals (melting point 247–249° C.).

Example 66

Preparation of 7-fluoro-3-oxo-N-(5-phenyl-2-pyrimidinyl)spiro[isobenzofuran-1(3H),4'-piperidine]- 1'-carboxamide A mixture of 7-fluorospiro[isobenzofuran-1(3H),4'-piperidine]-3-one hydrochloride (150 mg), phenyl N-(5-phenyl-2-pyrimidinyl)carbamate (170 mg) and triethylamine (0.24 mL) in chloroform (2 mL) was stirred at 60° C. for 2 hours. The reaction mixture was diluted with ethyl acetate. The whole was washed with 10% citric acid aqueous solution, saturated aqueous sodium bicarbonate and saturated saline solution and then dried over anhydrous $Na_2SO_4$. The concentration of the reaction mixture left a residue, which was recrystallized from ethyl acetate to give the subject compound (202 mg) as colorless crystals (melting point 244–246° C.).

Example 67

Preparation of 6-ethyl-3-oxo-N-(5-phenyl-2-pyrazinyl)spiro[isobenzofuran-1(3H),4'-piperidine]-1'-carboxamide (1) Preparation of 2-(4-ethylphenyl)-4,4-dimethyl-2-oxazoline To a solution of 4-ethylbenzoic acid (3.80 g) in anhydrous acetonitrile (100 mL) was added under a nitrogen atmosphere, triphenylphosphine (20 g), 2-amino-2-methyl-1-propanol (2.74 mL) and triethylamine (28.2 mL). The mixture was cooled on an ice bath and then tetrachloromethane (5.36 mL) was added. The reaction mixture was allowed to stand at room temperature and stirred for 18 hours. To the reaction mixture was added ethyl acetate and hexane and the precipitate was removed by filtration. The concentration of the filtrate left a residue, which was purified by column chromatography on silica gel (hexane/ethyl acetate/=9/1/ to 6/1) to give the subject compound (1.15 g).

(2) Preparation of 1'-benzyl-6-ethylspiro[isobenzofuran-1(3H),4'-piperidine]-3-one hydrochloride Under a nitrogen atmosphere, a solution of 2-(4-ethylphenyl)-4,4-dimethyl-2-oxazoline (1.15 g) in anhydrous tetrahydrofuran (100 mL) was cooled to −78° C. To this solution was added 1.5 M butyl lithium hexane solution (4.53 mL). After being stirred for 1 hour, 1-benzyl-4-piperidone (1.05 mL) was added dropwise. After the reaction temperature was allowed to rise up to room temperature, 2N hydrochloric acid was added to the reaction mixture to make the mixture acidic. The whole was refluxed for 2 hours. After cooling, sodium hydroxide aqueous solution was added to make the reaction mixture basic. The mixture was extracted with ethyl ether. The organic layer was washed with saturated saline solution and then dried over anhydrous $Na_2SO_4$. The concentration of the organic solvent left a residue, which was purified by column chromatography on silica gel (hexane/ethyl acetate/=3/2) to give the subject compound (409 mg).

(3) Preparation of 6-ethylspiro[isobenzofuran-1(3H),4'-piperidine]-3-one hydrochloride 1'-benzyl-6-ethylspiro[isobenzofuran-1(3H),4'-piperidine]-3-one hydrochloride (400 mg) was dissolved in methanol (10 mL) and 10% palladium carbon was added. The mixture was stirred under a hydrogen atmosphere for 1.5 hours. After the palladium carbon was removed by filtration, the filtrate was concentrated to give a residue, which was subjected to crystallization with methanol-ethyl ether to give the subject compound (222 mg).

(4) Preparation of 6-ethyl-3-oxo-N-(5-phenyl-2-pyrazinyl)spiro[isobenzofuran-1(3H),4'-piperidine]-1'-carboxamide To a suspension of 6-ethylspiro[isobenzofuran-1(3H),4'-piperidine]-3-one hydrochloride (53 mg) and phenyl N-(5-phenyl-2-pyrazinyl)carbamate (58 mg) in dimethyl sulfoxide (1 mL) was added 10 M sodium hydroxide aqueous solution (0.02 mL). The mixture was vigorously stirred for 5 minutes followed by partition between water and ethyl acetate. The organic layer was separated and then washed with saturated saline solution and then dried over anhydrous $Na_2SO_4$. The concentration of the organic solvent left a residue, which was subjected to the crystallization from ethyl acetate to give the subject compound (46 mg) as crystals (melting point 176–178° C.).

Example 68

Preparation of 6-hydroxy-3-oxo-N-(5-phenyl-2-pyrazinyl)spiro[isobenzofuran-1(3H),4'-piperidine]-1'-carboxamide (1) Preparation of 2-(4-methoxyphenyl)-4,4-dimethyl-2-oxazoline To a solution of 2-amino-2-methyl-1-propanol (14.4 g) and triethylamine (23 mL) in dried THF (200 mL) was added dropwise under ice-cooling a solution of 4-methoxybenzoyl chloride (25 g) in dried THF (20 mL). The mixture was stirred at room temperature for 1 hour and then water (200 mL) was added. The reaction mixture was extracted with ethyl acetate (100 mL) twice. The organic layer was washed with saturated saline solution and then dried over anhydrous $Na_2SO_4$. The concentration of the organic solvent provided the subject compound (29.5 g) as a white solid. Thionyl chloride (25 mL) was added to the above white solid compound, and the reaction was carried out at room temperature for one hour. The reaction mixture was made alkaline by the addition of 5N sodium hydroxide aqueous solution and was extracted twice each with ethyl acetate (100 mL). The combined organic layer was washed with saturated sodium chloride aqueous solution and dried with anhydrous sodium sulfate. The solvent was evaporated off to give the above-identified compound (22 g) as colorless oil.

(2) Preparation of 1'-benzyl-6-methoxyspiro[isobenzofuran-1(3H),4'-piperidine]-3-one Under a nitrogen atmosphere, to a solution of 2-(4-methoxyphenyl)-4,4-dimethyl-2-oxazoline (7.9 g) in anhydrous toluene (100 mL) was added dropwise under ice-cooling 1.5M butyl lithium hexane solution (28 mL). After being stirred for 3 hours at the same temperature, 1-benzyl-4-piperidone (8 g) in anhydrous toluene (20 mL) was added dropwise. After the reaction mixture was stirred at room temperature for 14 hours, a saturated ammonium chloride aqueous solution (50 mL) was added. The mixture was extracted with ethyl acetate (100 mL) twice. The organic layer was washed with saturated saline solution and then dried over anhydrous $Na_2SO_4$. The concentration of the organic solvent provided the compound (8.3 g) as a white solid. This compound was dissolved in methanol (50 mL) and concentrated sulfuric acid (4 mL) was added. The mixture was stirred at room temperature for 1 hour. To the reaction mixture was added 1N sodium hydroxide aqueous solution to make the reaction mixture basic. The mixture was extracted with ethyl acetate (100 mL) twice. The organic layer was washed with saturated saline solution and then dried over anhydrous $Na_2SO_4$. The concentration of the organic solvent provided the subject compound (6.6 g) as a yellow solid.

(3) Preparation of 6-hydroxyspiro[isobenzofuran-1(3H),4'-piperidine]-3-one hydrochloride 1'-benzyl-6-methoxyspiro[isobenzofuran-1(3H),4'-piperidine]-3-one (1.8 g) was dissolved in methylene chloride (20 mL). To this solution was added under ice-cooling boron tribromide (1.3 mL). After the reaction mixture was stirred at room temperature for 14 hours, 1N sodium hydroxide aqueous solution was added. The mixture was extracted with ethyl acetate (30 mL) twice. The organic layer was washed with saturated saline solution and then dried over anhydrous $Na_2SO_4$. The concentration of the organic solvent provided the compound (1.2 g) as a yellow solid, which was dissolved in methanol (30 mL). To this solution was added 4N hydrogen chloride-ethyl acetate (5 mL), 20% palladium hydroxide-carbon (300 mg). The mixture was stirred under a hydrogen atmosphere for 14 hours. After the catalyst was removed by filtration, the filtrate was concentrated to give the subject compound (891 mg) as a white solid.

(4) Preparation of 6-hydroxy-3-oxo-N-(5-phenyl-2-pyrazinyl)spiro[isobenzofuran-1(3H),4'-piperidine]-1'-carboxamide A mixture of 6-hydroxyspiro[isobenzofuran-1(3H),4'-piperidine]-3-one hydrochloride (51 mg), phenyl N-(5-phenyl-2-pyrazinyl)carbamate (58 mg) and triethylamine (119 μL) in chloroform (5 mL) was stirred at 80° C. for 2 hours. The reaction mixture was poured into water, and then extracted with chloroform (20 mL). The organic layer was washed with saturated saline solution (20 mL) and then dried over anhydrous $Na_2SO_4$. The concentration of the organic solvent left a residue, which was purified by column chromatography on silica gel (hexane/ethyl acetate/=4/1 to 1/2) followed by the recrystallization from ethyl ether-hexane to give the subject compound (29 mg) as colorless crystals (melting point 206–208° C.).

The compounds from Example 69 to Example 79 were prepared, according to the same preparation procedure described in Example 61 by using the corresponding starting material in place of 4-aminobenzophenon used in the Example 61.

Example 69 trans-3-oxo-N-(5-phenyl-2-pyrimidinyl)spiro[5-azaisobenzofuran-1(3H),1'-cyclohexane]-4'-carboxamide.

melting point 215–217° C.

Example 70 trans-N-[5-(3-fluorophenyl)-2-pyrimidinyl]-3-oxospiro[5-azaisobenzofuran-1(3H),1'-cyclohexane]-4'-carboxamide melting point 205–207° C.

Example 71 trans-N-[5-(2-fluorophenyl)-2-pyrimidinyl]-3-oxispiro[5-azaisobenzofuran-1(3H),1'-cyclohexane]-4'-carboxamide melting point 226–228° C.

Powder X-ray diffraction

| 2 θ (degrees) | Intensity (cps) |
| --- | --- |
| 11.14 | 970 |
| 14.62 | 1418 |
| 15.02 | 570 |
| 15.12 | 920 |
| 15.56 | 895 |
| 16.22 | 475 |
| 17.10 | 1873 |
| 19.22 | 1698 |
| 20.06 | 3202 |
| 20.54 | 542 |
| 20.78 | 1013 |
| 21.00 | 1063 |
| 21.78 | 2405 |
| 23.24 | 5557 |
| 24.12 | 555 |
| 24.90 | 888 |
| 25.98 | 487 |
| 26.30 | 500 |
| 27.52 | 2765 |
| 28.22 | 690 |
| 28.56 | 553 |
| 28.82 | 647 |
| 29.04 | 423 |
| 29.70 | 653 |
| 30.54 | 1102 |
| 32.84 | 362 |
| 36.46 | 408 |

Above powder X-ray diffraction analysis data were measured by the same conditions as Example 32.

Example 72 trans-3-oxo-N-(4-phenyl-2-oxazolyl)spiro[5-azaisobenzofuran-1(3H),1'-cyclohexane]-4'-carboxamide melting point 273–275° C.

Example 73 trans-N-[5-(2-methylphenyl)-2-pyrimidinyl]-3-oxospiro[5-azaisobenzofuran-1(3H),1'-cyclohexane]-4'-carboxamide melting point 213–215° C.

Example 74 trans-N-[5-(3-methylphenyl)-2-pyrimidinyl]-3-oxospiro[5-azaisobenzofuran-1(3H),1'-cyclohexane]-4'-carboxamide melting point 145–147° C.

Example 75 trans-N-[5-(3-fluoromethoxyphenyl)-2-pyrimidinyl]-3-oxospiro[5-azaisobenzofuran-1(3H),1'-cyclohexane]-4'-carboxamide melting point 157–159° C.

Example 76 trans-N-[5-(3-fluoromethylphenyl)-2-pyrimidinyl]-3-oxospiro[5-azaisobenzofuran-1(3H),1'-cyclohexane]-4'-carboxamide melting point 153–155° C.

Example 77 trans-N-[5-(3-fluoro-5-methoxyphenyl)-2-pyrimidinyl]-3-oxospiro[5-azaisobenzofuran-1(3H),1'-cyclohexane]-4'-carboxamide melting point 218–220° C.

Example 78 trans-N-[5-(2-fluoro-5-methylphenyl)-2-pyrimidinyl]-3-oxospiro[5-azaisobenzofuran-1(3H),1'-cyclohexane]-4'-carboxamide melting point 151–153° C.

Example 79 trans-N-[4-(3-fluoromethoxylphenyl)-2-oxazolyl]-3-oxospiro[5-azaisobenzofuran-1(3H),1'-cyclohexane]-4'-carboxamide melting point 214–217° C.

Example 80

Preparation of trans-N-[5-(3-hydroxymethylphenyl)-2-pyrimidinyl]-3-oxospiro[5-azaisobenzofuran-1(3H),1'-cyclohexane]-4'-carboxamide To a solution of 2-chloro-1,3-dimethylimidazolium chloride (613 mg) in chloroform (10 mL) was added pyridine (0.489 mL), trans-3-oxospiro[5-azaisobenzofuran-1(3H),1'-cyclohexane]-4'-carboxylic acid (300 mg) and 2-amino-5-bromopyrimidine (211 mg). The mixture was stirred at room temperature overnight. The reaction mixture was diluted with ethyl acetate.

The whole was washed with 10% citric acid aqueous solution, saturated sodium bicarbonate aqueous solution, saturated saline solution and then dried over anhydrous $Na_2SO_4$. The concentration of the organic solvent left a residue, which was purified by column chromatography on silica gel (hexane/ethyl acetate=1/1 to 1/3 to 1/4 to 1/5) followed by the crystallization from ethyl acetate to give the desired amide (210 mg). This amide was suspended in ethyleneglycol dimethyl ether (3.5 mL), and water (0.5 mL), 3-hydroxymethylphenylboronic acid (95 mg), 2M sodium carbonate aqueous solution (0.31 mL) and tetrakistriphenylphosphinepalladium (30 mg) was added thereto.

The mixture was refluxed for 2 hours and then diluted with water. The whole was extracted with ethyl acetate and then dried over anhydrous $Na_2SO_4$. The concentration of the organic solvent left a residue, which was purified by column chromatography on silica gel (ethyl acetate/methanol=1/0 to 30/1 to 20/1 to 15/1) to give the subject compound (151 mg) as light yellow crystals (melting point 207–209° C.).

Example 81

Preparation of trans-N-[5-(3-hydroxyphenyl)-2-pyrimidinyl]-3-oxospiro[5-azaisobenzofuran-1(3H),1'-cyclohexane]-4'-carboxamide To a solution of 2-chloro-1,3-dimethylimidazolium chloride (622 mg) in chloroform (7 mL) was added pyridine (0.50 mL), trans-3-oxospiro[5-azaisobenzofuran-1(3H),1'-cyclohexane]-4'-carboxylic acid (303 mg) and 2-amino-5-(3-benzyloxyphenyl)pyrimidine (340 mg). The mixture was stirred at room temperature overnight. The reaction mixture was diluted with ethyl acetate. The whole was washed with 10% citric acid aqueous solution, saturated sodium bicarbonate aqueous solution, saturated saline solution and then dried over anhydrous $Na_2SO_4$. The concentration of the organic solvent left a residue, which was purified by column chromatography on silica gel (hexane/ethyl acetate=1/1 to 1/2 to 1/4 to 1/5 to 1/6) followed by the crystallization from ethyl acetate to give the desired amide (210 mg). This amide was dissolved in methanol (5 mL) and tetrahydrofuran (5 mL), and 10% palladium-carbon (120 mg) was added. The mixture was stirred at room temperature under a hydrogen atmosphere overnight. The catalyst was removed by filtration. The filtrate was concentrated to give a residue, which was purified by column chromatography on silica gel (chloroform/methanol=50/1 to 30/1) to give a solid compound. The solid compound was washed with ethanol and then recrystallized from ethyl acetate to give the subject compound (95 mg) as light yellow crystals (melting point 260–262° C.).

The compounds from Example 82 to Example 89 were prepared, according to the same preparation procedure described in Example 62 by using the corresponding starting material in place of 4-aminobenzophenon used in the Example 62.

Example 82 trans-3-oxo-N-(5-phenyl-2-pyrimidinyl)spiro[6-azaisobenzofuran-1(3H),1'-cyclohexane]-4'-carboxamide melting point 189–191° C.

Example 83 trans-N-[5-(3-fluoromethylphenyl)-2-pyrimidinyl]-3-oxospiro[6-azaisobenzofuran-1(3H),1'-cyclohexane]-4'-carboxamide melting point 199–200° C.

Example 84 trans-N-[5-(3-fluoromethoxyphenyl)-2-pyrimidinyl]-3-oxospiro[6-azaisobenzofuran-1(3H),1'-cyclohexane]-4'-carboxamide melting point 198–200° C.

Example 85 trans-3-oxo-N-(6-phenyl-1,2,4-triazin-3-yl)spiro[6-azaisobenzofuran-1(3H),1'-cyclohexane]-4'-carboxamide melting point 272–275° C.

Example 86 trans-N-[5-(2-difluoromethoxyphenyl)-3-pyrazolyl]-3-oxospiro[6-azaisobenzofuran-1(3H),1'-cyclohexane]-4'-carboxamide melting point 239–240° C.

Example 87 trans-N-[5-(3-difluoromethoxyphenyl)-3-pyrazolyl]-3-oxospiro[6-azaisobenzofuran-1(3H),1'-cyclohexane]-4'-carboxamide melting point 183–185° C.

Example 88 trans-N-[5-(3-fluorophenyl)-3-pyrazolyl]-3-oxospiro
[6-azaisobenzofuran-1(3H),1'-cyclohexane]-4'-
carboxamide melting point 182–184° C.

Example 89 trans-N-[5-(4-fluorophenyl)-3-pyrazolyl]-3-oxospiro
[6-azaisobenzofuran-1(3H),1'-cyclohexane]-4'-
carboxamide melting point 228–229° C.

Example 90

Preparation of trans-N-(4-benzoylphenyl)-3-
oxospiro[7-azaisobenzofuran-1(3H),1'-cyclohexane]
4'-carboxamide (1) Preparation of 3-cyano-2-hydroxypyridine To malonaldehyde bisdimethylacetal (16.4 g) was added 0.5 N hydrochloric acid (40 mL). The mixture was stirred at 50° C. for 20 minutes and then cooled to room temperature. To the reaction mixture was added triethylamine (16 mL) followed by 2-cyanoacetoamide (9 g). The whole was stirred at room temperature for 30 minutes and further heated at 60° C. for 90 minutes as well as 100° C. for 2 hours. After cooling, the reaction mixture was concentrated to give a residue, which was recrystallized from ethanol-ethyl ether to give the subject compound (7.49 g).

(2) Preparation of 2-bromo-3-cyanopyridine

Tetrabutylammonium bromide (35.4 g) and diphosphorus pentaoxide (15.58 g) was suspended in toluene 100 mL). After the mixture was stirred at 70° C. for 30 minutes, 3-cyano-2-hydroxypyridine (6.59 g) was added thereto. The mixture was refluxed for 4 hours. The reaction mixture was poured into the ice water (200 g) and extracted with ethyl acetate (200 mL×2). The organic layer was dried over anhydrous $Na_2SO_4$. The concentration of the solvent gave a oily residue, which was purified by column chromatography on silica gel (hexane/ethyl acetate=4/1 to 3/1) to give a solid compound. The solid compound was recrystallized from ethyl acetate-hexane to give the subject compound (5.16 g).

(3) Preparation of spiro[7-azaisobenzofuran-1(3H),1'-cyclohexane]-3,4'-dione 2-bromo-3-cyanopyridine (2.96 g) and 1,4-cyclohexanedione monoethyleneketal (3.47 g) were dissolved in anhydrous tetrahydrofuran (38 mL). After being cooled to −78° C., n-butyl lithium (1.5 M hexane solution, 12.64 mL) was added and the mixture was stirred at −78° C. for 30 minutes. The reaction temperature was allowed to rise up to the room temperature. The reaction mixture was poured into water (40 mL) and extracted with ethyl acetate (100 mL×3). The organic layer was dried over anhydrous $MgSO_4$. The concentration of the solvent gave a residue, which was recrystallized from ethyl ether-hexane to give iminoether compound (2.93 g). This compound was dissolved in acetone (5 mL) and 2N hydrochloric acid (30 mL). The solution was refluxed for 2 hours. After cooling, 2N sodium hydroxide aqueous solution was added to the reaction mixture to adjust pH to 4. The whole was extracted with ethyl acetate (100 mL ×3). The organic layer was dried over anhydrous $MgSO_4$. The concentration of the solvent gave a residue, which was recrystallized from ether-hexane to give the subject compound (1.07 g).

(4) Preparation of cis-4'-hydroxyspiro[7-azaisobenzofuran-1(3H),1'-cyclohexane]-3-one Spiro[7-azaisobenzofuran-1(3H),1'-cyclohexane]-3,4'-dione (1.6 g) was suspended in tetrahydrofuran (37 mL). After being cooled to 0° C., lithium tert-butoxyaluminium hydride (1.0M tetrahydrofuran solution, 9.58 mL) was added dropwise to the mixture. After the mixture was stirred at 0° C. for 90 minutes, 1N hydrochloric acid was added to adjust pH to 2. The mixture was extracted with ethyl acetate (100 mL×4). The organic layer was dried over anhydrous $MgSO_4$. The concentration of the solvent gave the subject compound (1.58 g).

(5) Preparation of trans-3-oxospiro[7-azaisobenzofuran-1(3H),1'-cyclohexane]-4'-carbonitrile Cis-4'-hydroxyspiro[7-azaisobenzofuran-1(3H),1'-cyclohexane]-3-one (1.58 g) and triethylamine (1.81 mL) were dissolved in chloroform (28 mL). After being cooled to 0° C., methanesulfonyl chloride (0.67 mL) was added thereto. The mixture was stirred at room temperature for 2 hour3 and then poured into the saturated sodium bicarbonate aqueous solution (50 mL). The whole was extracted with chloroform (100 mL×3). The organic layer was dried over anhydrous $MgSO_4$. The concentration of the solvent gave a oily residue, which was purified by column chromatography on silica gel (hexane/ethyl acetate=2/1 to 1/2) to give a solid compound. The solid compound was recrystallized from ethyl acetate-hexane to give the desired mesylate compound (2.03 g). This compound was dissolved in anhydrous dimethylformamide (30 mL), and triethylammonium cyanide (3.2 g) was added thereto. The mixture was stirred at 100° C. for 3 hours. After being cooled, the reaction mixture was poured into water (100 mL). The whole was extracted with ethyl acetate (100 mL×3). The organic layer was dried over anhydrous $MgSO_4$. The concentration of the solvent gave a oily residue, which was purified by column chromatography on silica gel (hexane/ethyl acetate=3/1 to 2/1) to give a solid compound. The solid compound was further recrystallized from ethyl ether-hexane to give the subject compound (515 mg).

(6) Preparation of trans-3-oxospiro[7-azaisobenzofuran-1(3H),1'-cyclohexane]-4'-carboxylic acid Water (6.6 mL) and concentrated sulfuric acid (2.2 mL) were added to trans-3-oxospiro[7-azaisobenzofuran-1(3H),1'-cyclohexane]-4'-carbonitrile (515 mg). The mixture was refluxed for 13 hours. After the reaction mixture was cooled to 0° C., 4N sodium hydroxide aqueous solution was added to adjust pH to 4. The crystal precipitated was collected by filtration. The crystal was washed with water, ethanol as well as diisopropyl ether and then dried. The subject compound (500 mg) was obtained.

$^1$H-NMR (300 MHz, DMSO-$d_6$, δ ppm): 1.73–1.80(2H, m), 1.81–1.94(2H, m), 1.99–2.08(2H, m), 2.14–2.22(2H, m), 2.64–2.68(1H, m), 7.63(1H, dd, J=7.8, 4.8 Hz), 8.28(1H, dd, J=7.8, 1.5 Hz), 8.89(1H, dd, J=4.8, 1.5 Hz).

(7) Preparation of trans-N-(4-benzoylphenyl)-3-oxospiro-[7-azaisobenzofuran-1(3H),1'-cyclohexane]-4'-carboxamide trans-3-oxospiro[7-azaisobenzofuran-1(3H),1'-cyclohexane]-4'-carboxylic acid (26 mg) and 4-aminobenzophenone (20 mg) were dissolved in anhydrous pyridine (1 mL). 1-(3-dimethylaminopropyl)-3-ethylcarbodiimide hydrochloride (29 mg) was added thereto. The mixture was stirred at room temperature for 18 hours.

The reaction mixture was poured into water (10 mL). The whole was extracted with ethyl acetate (30 mL×3). The combined organic layer was dried over anhydrous $MgSO_4$. The concentration of the solvent gave an oily residue, which was purified by column chromatography on silica gel (hexane/ethyl acetate=3/1 to 2/1) to give a solid compound. The solid compound was further recrystallized from ethyl acetate-hexane to give the subject compound (30 mg) as colorless crystals (melting point 214–216° C.)

Employing the procedure substantially as described in Example 90-(7), but substituting the appropriate amines for 4-aminobenzophenone used in Example 90-(7), compounds of Examples 91 to 95 were prepared.

Example 91 trans-N-[1-(3.5-difluorophenyl)-4-imidazolyl]-3-oxospiro[7-azaisobenzofuran-1(3H),1'-cyclohexane]-4'-carboxamide melting point 269–271° C.
Powder X-ray diffraction

| 2 θ (degrees) | Intensity (cps) |
| --- | --- |
| 6.68 | 338 |
| 7.62 | 288 |
| 13.42 | 1202 |
| 14.22 | 693 |
| 14.36 | 1880 |
| 15.48 | 965 |
| 16.40 | 652 |
| 16.92 | 1240 |
| 17.00 | 1232 |
| 18.82 | 1258 |
| 19.30 | 690 |
| 20.02 | 908 |
| 20.12 | 932 |
| 20.26 | 515 |
| 21.56 | 663 |
| 22.80 | 560 |
| 22.90 | 755 |
| 23.12 | 538 |
| 23.34 | 520 |
| 23.42 | 502 |
| 23.88 | 1342 |
| 25.10 | 2087 |
| 26.70 | 722 |
| 28.64 | 348 |
| 28.98 | 272 |
| 29.66 | 273 |
| 31.42 | 273 |
| 31.94 | 315 |
| 32.08 | 353 |
| 34.06 | 293 |
| 36.02 | 267 |

Above powder X-ray diffraction analysis data were measured by the same conditions as Example 32.

Example 92 trans-3-oxo-N-[2-phenyl-4-pyridyl]spiro[7-azaisobenzofuran-1(3H),1'-cyclohexane]-4'-carboxamide melting point 221–223° C.

Example 93 trans-3-oxo-N-(1-phenyl-4-pyrazolyl)spiro[7-azaisobenzofuran-1(3H),1'-cyclohexane]-4'-carboxamide melting point 240–242° C.

Example 94 trans-3-oxo-N-(1-phenyl-3-pyrrolyl)spiro[7-azaisobenzofuran-1(3H),1'-cyclohexane]-4'-carboxamide melting point 214–217° C.

Example 95 trans-N-[1-(4-fluorophenyl)-3-pyrazolyl]-3-oxospiro[7-azaisobenzofuran-1(3H),1'-cyclohexane]-4'-carboxamide melting point 210–212° C.

Employing the procedure substantially as described in Example 57-(6), but substituting the appropriate amines for 4-aminobenzophenone used in Example 57-(6), compounds of Examples 96 to 98 were prepared.

Example 96 trans-3-oxo-N-(I-phenyl-3-pyrazolyl)spiro[4-azaisobenzofuran-1(3H),1'-cyclohexane]-4'-carboxamide melting point 200–202° C.

Example 97 trans-3-oxo-N-(1-phenyl-4-pyrazolyl)spiro[4-azaisobenzofuran-1(3H),1'-cyclohexane]-4'-carboxamide melting point 223–225° C.
Powder X-ray diffraction

| 2 θ (degrees) | Intensity (cps) |
| --- | --- |
| 8.14 | 1612 |
| 11.58 | 613 |
| 11.86 | 4470 |
| 12.60 | 1472 |
| 13.20 | 1208 |
| 13.30 | 975 |
| 15.86 | 1913 |
| 16.32 | 1665 |
| 17.72 | 2347 |
| 18.66 | 1482 |
| 18.76 | 2192 |
| 19.38 | 647 |
| 19.42 | 805 |
| 19.68 | 4470 |
| 19.76 | 3805 |
| 20.60 | 2302 |
| 21.46 | 1698 |
| 22.26 | 1375 |
| 22.34 | 1550 |
| 23.10 | 1422 |
| 23.88 | 588 |
| 24.48 | 697 |
| 24.66 | 3807 |
| 24.76 | 6918 |
| 25.28 | 992 |
| 25.38 | 1390 |
| 26.14 | 447 |
| 26.74 | 1853 |
| 27.50 | 2855 |
| 28.62 | 943 |
| 28.70 | 975 |
| 30.58 | 1747 |
| 31.22 | 543 |
| 33.68 | 670 |
| 33.78 | 918 |

Above powder X-ray diffraction analysis data were measured by the same conditions as Example 32.

Example 98 trans-N-[1-(3-fluorophenyl)-4-pyrazolyl]-3-oxospiro-4-azaisobenzofuran-1(3H),1'-cyclohexane]-4'-carboxamide melting point 176–178° C.

Employing the procedure substantially as described in Example 62-(6), but substituting the appropriate amines for 4-aminobenzophenone used in Example 62-(6), compounds of Examples 99 to 106 were prepared.

Example 99 trans-3-oxo-N-(]-phenyl-3-pyrazolyl)spiro[6-azaisobenzofuran-1(3H),1'-cyclohexane]-4'-carboxamide melting point 249–250° C.

Example 100 trans-N-[1-(4-fluorophenyl)-3-pyrazolyl]-3-oxospiro[6-azaisobenzofuran-1(3H),1'-cyclohexane]-4'-carboxamide melting point 254–257° C.

Example 101 trans-N-[1-(2-fluorophenyl)-3-pyrazolyl]-3-oxospiro[6-azaisobenzofuran-1(3H),1'-cyclohexane]-4'-carboxamide melting point 239–241° C.

Example 102 trans-3-oxo-N-(5-phenyl-1,2,4-thiadiazol-3-yl)spiro[6-azaisobenzofuran-1(3H),1'-cyclohexane]-4'-carboxamide melting point 221–223° C.

Example 103 trans-3-oxo-N-(5-phenyl-3-isoxazolyl)spiro[6-azaisobenzofuran-1(3H),1'-cyclohexane]-4'-carboxamide melting point 259–261° C.

Example 104 trans-3-oxo-N-(6-phenyl-3-pyridyl)spiro[6-azaisobenzofuran-1(3H),1'-cyclohexane]-4'-carboxamide melting point 249–251° C.

Example 105 trans-3-oxo-N-(2-phenyl-3-thiazolyl)spiro[6-azaisobenzofuran-1(3H),1'-cyclohexane]-4'-carboxamide melting point 278–280° C.

Example 106 trans-3-oxo-N-(2-phenyl-1,2,3-triazol-4-yl)spiro[6-azaisobenzofuran-1(3H),1'-cyclohexane]-4'-carboxamide melting point 232–233° C.

Formulation example 1

20.0 grams of compound of Example 1, 417 grams of lactose, 80 grams of crystalline cellulose and 80 grams of partial α-starch were blended with a V-cone blender. To the mixture was added 3.0 grams of magnesium stearate and the whole was blended. The blended powder was compressed into 3000 tablets by conventional procedure so that each tablet has a weight of 150 mg and 7.0 mm in diameter.

The content of one tablet with a weight of 150 mg

| the compound of Example 1 | 5.0 mg |
| lactose | 104.25 mg |
| crystalline cellulose | 20.0 mg |
| partial α-starch | 20.0 mg |
| magnesium stearate | 0.75 mg |

10.8 grams of hydroxypropylcellulose 2910 and 2.1 grams of polyethylene glycol 6000 were dissolved in 172.5 grams of purified water. To the solution was dispersed 2.1 grams of titanium oxide to provide a coating liquid. 2500 tablets prepared in Formulation example 1, was subjected to spray-coating with the coating liquid using HICOATER-MINI to provide a film coated tablet with a weight of 155 mg.

The content of one tablet (155 mg)

| the tablet prepared in the Formulation example 1 | 150 mg |
| hydroxypropylcellulose 2910 | 3.6 mg |
| Polyethylene glycol 6000 | 0.7 mg |
| titanium dioxide | 0.7 mg |

Compounds of the present invention exhibit NPY antagonistic activities and are useful as agents for the treatment of various diseases related to NPY, for example, cardiovascular disorders such as hypertension, nephropathy, heart disease, vasospasm, arteriosclerosis and the like, central nervous system disorders such as bulimia, depression, anxiety, seizure, epilepsy, dementia, pain, alcoholism, drug withdrawal and the like, metabolic diseases such as obesity, diabetes, hormone abnormality, hypercholesterolemia, hyperlipidemia and the like, sexual and reproductive dysfunction, gastro-intestinal disorder, respiratory disorder, inflammation or glaucoma, and the like.

What is claimed is:

1. A compound represented by the general formula (I):

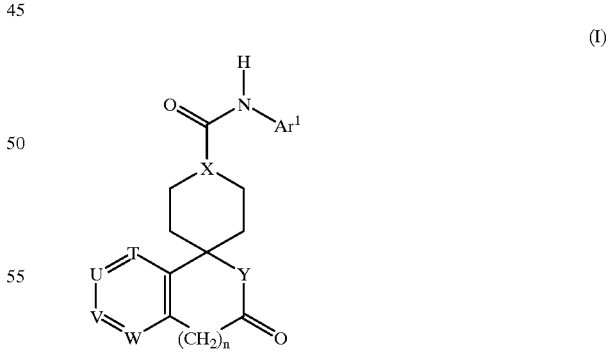

wherein $Ar^1$ represents an aryl or heteroaryl which may be substituted, the substituent being selected from the group consisting of halogen, nitro, lower alkyl, halo(lower)alkyl, hydroxy(lower)alkyl, cyclo(lower)alkyl, lower alkenyl, lower alkoxy, halo(lower)alkoxy, lower alkylthio, carboxyl, lower alkanoyl, lower alkoxycarbonyl, lower alkylene optionally substituted with oxo, and a group represented by formula of —Q—$Ar^2$;

Ar² represents an aryl or heteroaryl which may be substituted, the substituent being selected from the group consisting of halogen, cyano, lower alkyl, halo (lower)alkyl, hydroxy(lower)alkyl, hydroxy, lower alkoxy, halo(lower)alkoxy, lower alkylamino, di-lower alkylamino, lower alkanoyl and aryl;

n represents 0 or 1;

Q represents a single bond or carbonyl;

T, U, V and W each independently represent a nitrogen atom or a methine group which may have a substituent selected from the group consisting of halogen, lower alkyl, hydroxy and lower alkoxy, wherein at least two of which represent said methine group;

X represents nitrogen;

Y represents an imino which may be substituted with a lower alkyl, or oxygen; and a salt or ester thereof.

2. The compound of claim 1, wherein the aryl in Ar¹ is phenyl.

3. The compound of claim 1, wherein the heteroaryl in Ar¹ is pyrrolyl, imidazolyl, pyrazolyl, thiazolyl, oxazolyl, isoxazolyl, 1,2,3-triazolyl, 1,2,4-thiadtiazolyl, pyridyl, pyrazinyl, pyrimidinyl, 1,2,4-triazinyl, benzoxazolyl, benzothiazolyl, quinolyl or pyrido[3,2-b]pyridyl.

4. The compound of claim 1, wherein each of T, U, V and W is a methine which may have a substituent selected from the group consisting of halogen, lower alkyl, hydroxy and lower alkoxy.

5. The compound of claim 4, wherein each of T, U, V and W is a methine which may be substituted with halogen.

6. The compound of claim 1, wherein one of T, U, V and W is nitrogen.

7. The compound of claim 1, wherein Y is an unsubstituted imino or oxygen.

8. The compound of claim 1, wherein Y is oxygen.

9. The compound of claim 1 which is represented by the general formula (I-a):

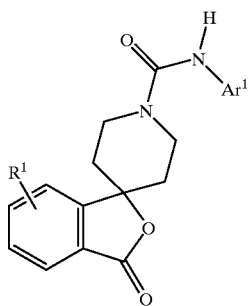

(I-a)

wherein Ar¹ represents an aryl or heteroaryl which may be substituted, the substituent being selected from the group consisting of halogen, nitro, lower alkyl, halo (lower)alkyl, hydroxy(lower)alkyl, cyclo(lower)alkyl, lower alkenyl, lower alkoxy, halo(lower)alkoxy, lower alkylthio, carboxyl, lower alkanoyl, lower alkoxycarbonyl, lower alkylene optionally substituted with oxo, and a group represented by formula of —Q—Ar²;

Ar² represents an aryl or heteroaryl which may be substituted, the substituent being selected from the group consisting of halogen, cyano, lower alkyl, halo (lower)alkyl, hydroxy(lower)alkyl, hydroxy, lower alkoxy, halo(lower)alkoxy, lower alkylamino, di-lower alkylamino, lower alkanoyl and aryl;, Q represents a single bond or carbonyl;

R¹ represents hydrogen or halogen.

10. The compound of claim 9, wherein the aryl in Ar¹ is phenyl.

11. The compound of claim 9, wherein the heteroaryl in Ar¹ is imidazolyl, pyrazolyl, isoxazolyl, 1,2,4-thiadiazolyl, pyrazinyl, pyrimidinyl, quinolyl or pyrido[3,2-b]pyridyl.

12. The compound of claim 1, which is

N-(4-benzoylphenyl)-3-oxospiro[isoindoline-1,4'-piperidine]-1'-carboxamide, 3-oxo-N-(5-phenyl-2-pyrazinyl)spiro[isoindoline-1,4'-piperidine]-1'-carboxamide, N-(7-methyl-2-quinolyl)-3-oxospiro[isoindoline-1,4'-piperidine]-1'-carboxamide, N-(4-benzoylphenyl)-2-methyl-3-oxospiro[isoindoline-1,4'-piperidine]-1'-carboxamide, N-(4-benzoylphenyl)-3,4-dihydro-3-oxospiro[isoquinoline-1(2H),4'-piperidine]-1'-carboxamide, 3,4-dihydro-3-oxo-N-(5-phenyl-2-pyrazinyl)spiro[isoquinoline-1(2H),4'-piperidine]-1'-carboxamide, 3,4-dihydro-N-(7-methyl-2-quinolyl)-3-oxospiro[isoquinoline-1(2H),4'-piperidine]-1'-carboxamide, N-(4-acetylphenyl)-3,4-dihydro-3-oxospiro[isoquinoline-1(2H),4'-piperidine]-1'-carboxamide, 3,4-dihydro-3-oxo-N-[1-(2-quinolyl)-4-imidazolyl]spiro[isoquinoline-1(2H),4'-piperidine]-1'-carboxamide, 3,4-dihydro-3-oxo-N-(5-oxo-5,6,7,8-tetrahydro-2-naphthyl)spiro[isoquinoline-1(2H),4'-piperidine]-1'-carboxamide, 3,4-dihydro-N-[5-(2-methyl-1-propenyl)-2-pyrazinyl]-3-oxospiro[isoquinoline-1(2H),4'-piperidine]-1'-carboxamide, 3,4-dihydro-3-oxo-N-(3-phenyl-5-isoxazolyl)spiro[isoquinoline-1(2H),4'-piperidine]-1'-carboxamide, N-[1-(7-benzo[b]furanyl)-4-imidazolyl]-3,4-dihydro-3-oxospiro[isoquinoline-1(2H),4'-piperidine]-1'-carboxamide, N-[1-(3-difluoromethoxyphenyl)-4-imidazolyl]-3,4-dihydro-3-oxospiro[isoquinoline-1(2H),4'-piperidine]-1'-carboxamide, 3,4-dihydro-3-oxo-N-[4-(2-pyridylcarbonyl)phenyl]spiro[isoquinoline-1(2H),4'-piperidine]-1'-carboxamide, N-(3,4-dichlorophenyl)-3,4-dihydro-3-oxospiro[isoquinoline-1(2H),4'-piperidine]-1'-carboxamide, N-[1-(3-chlorophenyl)-4-imidazolyl]-3,4-dihydro-3-oxospiro[isoquinoline-1(2H),4'-piperidine]-1'-carboxamide, 3,4-dihydro-3-oxo-N-(5-phenyl-2-thiazolyl)spiro[isoquinoline-1(2H),4'-piperidine]-1'-carboxamide, 3,4-dihydro-3-oxo-N-[5-(2-pyridyl)- 2-pyrazinyl]spiro[isoquinoline-1(2H),4'-piperidine]-1'-carboxamide, 3,4-dihydro-N-(4-methyl-2-benzothiazolyl)-3-oxospiro[isoquinoline-1(2H),4'-piperidine]-1'-carboxamide, N-(5-chloro-2-benzoxazolyl)-3,4-dihydro-3-oxospiro[isoquinoline-1(2H),4'-piperidine]-1'-carboxamide, N-(4-benzoylphenyl)-3-oxospiro[isobenzofuran-1(3H),4'-piperidine]-1'-carboxamide, 3-oxo-N-(5-phenyl-2-pyrazinyl)-spiro[isobenzofuran-1(3H),4'-piperidine]-1'-carboxamide, N-(7-methyl-2-quinolyl)-3-oxospiro[isobenzofuran-1(3H),4'-piperidine]-1'-carboxamide, 3-oxo-N-(3-phenyl-5-isoxazolyl)spiro[isobenzofuran-1(3H),4'-piperidine]-1'-carboxamide, 3-oxo-N-(7-trifluoromethylpyrido[3,2-b]pyridin-2-yl)spiro[isobenzofuran-1(3H),4'-piperidine]-1'-carboxamide, 3-oxo-N-(5-phenyl-2-pyrimidinyl)spiro[isobenzofuran-1(3H),4'-piperidine]-1'-carboxamide, 3-oxo-N-[1-(3-quinolyl)-4-imidazolyl]spiro[isobenzofuran-1(3H),4'-piperidine]-1'-carboxamide, 3-oxo-N-(5-phenyl-3-pyrazolyl)spiro[isobenzofuran-1(3H), 4'-piperidine]-1'-carboxamide,
N-[5-(4-chlorophenyl)-3-pyrazolyl]-3-oxospiro [isobenzofuran-1(3H),4'-piperidine]-1'-carboxamide,
3-oxo-N-[5-(3-quinolyl)-3-pyrazolyl]spiro[isobenzofuran-1 (3H),4'-piperidine]-1'-carboxamide,
N-[5-(3-fluorophenyl)-2-pyrimidinyl]-3-oxospiro [isobenzofuran-1(3H),4'-piperidine]-1'-carboxamide,
3-oxo-N-[5-(3-trifluoromethylphenyl)-2-pyrimidinyl]spiro [isobenzofuran-1(3H),4'-piperidine]-1'-carboxamide,
N-[5-(3-chlorophenyl)-2-pyrimidinyl]-3-oxospiro [isobenzofuran-1(3H),4'-piperidine]-1'-carboxamide,
N-(7-difluoromethoxypyrido[3,2-b]pyridin-2-yl)-3-oxospiro[isobenzofuran-1(3H),4'-piperidine]-1'-carboxamide,
3-oxo-N-(5-phenyl-1,2,4-thiadiazol-3-yl)spiro [isobenzofuran-1(3H),4'-piperidine]-1'-carboxamide,
N-{1-[3-(2-hydroxyethyl)phenyl]-4-imidazolyl}-3-oxospiro [isobenzofuran-1(3H),4'-piperidine]-1'-carboxamide,
N-[4-(1-ethyl-2-imidazolyl)phenyl]- 3-oxospiro [isobenzofuran-1(3H),4'-piperidine]-1'-carboxamide,
N-[1-(3-methoxyphenyl)-4-imidazolyl]-3-oxospiro [isobenzofuran-1(3H),4'-piperidine]-1'-carboxamide,
6-fluoro-3-oxo-N-(5-phenyl-2-pyrazinyl)spiro [isobenzofuran-1(3H),4'-piperidine]-1'-carboxamide,
6-fluoro-3-oxo-N-(5-phenyl-2-pyrimidinyl)spiro [isobenzofuran-1(3H),4'-piperidine]-1'-carboxamide,
5-fluoro-3-oxo-N-(5-phenyl-2-pyrazinyl)spiro [isobenzofuran-1(3H),4'-piperidine]-1'-carboxamide,
5-fluoro-3-oxo-N-(5-phenyl-2-pyrimidinyl)spiro [isobenzofuran-1(3H),4'-piperidine]-1'-carboxamide,
N-(4-benzoylphenyl)-3,4-dihydro-3-oxospiro[1H-2-benzopyran-1,4'-piperidine]-1'-carboxamide,
3,4-dihydro-3-oxo-N-(5-phenyl-2-pyrazinyl)spiro[1H-2-benzopyran-1,4'-piperidine]-1'-carboxamide,
N-(5-benzoyl-2-pyrazinyl)-3,4-dihydro-3-oxospiro[1H-2-benzopyran-1,4'-piperidine]-1'-carboxamide,
N-[5-(4-hydroxyphenyl)-2-pyrazinyl]-3-oxospiro [isobenzofuran-1(3H),4'-piperidine]-1'-carboxamide,
N-(5-(3-hydroxyphenyl)-2-pyrazinyl]-3-oxospiro [isobenzofuran-1(3H),4'-piperidine]-1'-carboxamide,
4-fluoro-3-oxo-N-(5-phenyl-2-pyrimidinyl)spiro [isobenzofuran-1(3H),4'-piperidine]-1'-carboxamide,
7-fluoro-3-oxo-N-(5-phenyl-2-pyrimidinyl)spiro [isobenzofuran-1(3H),4'-piperidine]-1'-carboxamide,
6-ethyl-3-oxo-N-(5-phenyl-2-pyrazinyl)spiro [isobenzofuran-1(3H),4'-piperidine]-1'-carboxamide, or
6-hydroxy-3-oxo-N-(5-phenyl-2-pyrazinyl)spiro [isobenzofuran-1(3H),4'-piperidine]-1'-carboxamide.

13. The compound of claim 1, which is 3-oxo-N-(5-phenyl-2-pyrazinyl)-spiro[isobenzofuran-1(3H),4'-piperidine]-1'-carboxamide.

14. The compound of claim 1, which is 3-oxo-N-(7-trifluoromethylpyrido[3,2-b]pyridin-2-yl)spiro [isobenzofuran-1(3H),4'-piperidine]- 1'-carboxamide.

15. The compound of claim 1, which is N-[5-(3-fluorophenyl)-2-pyrimidinyl]-3-oxospiro[isobenzofuran-1 (3H),4'-piperidine]-1'-carboxamide.

16. A process for producing a compound of the general formula (I-1):

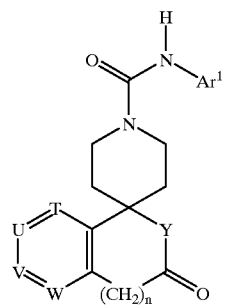

(I-1)

wherein Ar¹ represents an aryl or heteroaryl which may be substituted, the substituent being selected from the group consisting of halogen, nitro, lower alkyl, halo (lower)alkyl, hydroxy(lower)alkyl, cyclo(lower)alkyl, lower alkenyl, lower alkoxy, halo(lower)alkoxy, lower alkylthio, carboxyl, lower alkanoyl, lower alkoxycarbonyl, lower alkylene optionally substituted with oxo, and a group represented by formula of —Q—Ar²;

Ar² represents an aryl or heteroaryl which may be substituted, the substituent being selected from the group consisting of halogen, cyano, lower alkyl, halo (lower)alkyl, hydroxy(lower)alkyl, hydroxy, lower alkoxy, halo(lower)alkoxy, lower alkylamino, di-lower alkylamino, lower alkanoyl and aryl;

Q represents a single bond or carbonyl;

T, U, V and W each independently represent a nitrogen atom or a methine group which may have a substituent selected from the group consisting of halogen, lower alkyl, hydroxy and lower alkoxy, wherein at least two of which represent said methine group;

n and Y have the same meaning as described hereinafter; and a salt or ester thereof, which comprises:
reacting a compound of the general formula (II):

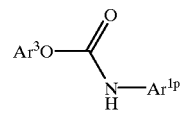

wherein $Ar^{1p}$ represents an aryl or heteroaryl which may be substituted, the substituent being selected from the group consisting of halogen, nitro, lower alkyl, halo (lower)alkyl, cyclo(lower)alkyl, lower alkenyl, lower alkoxy, halo(lower)alkoxy, lower alkylthio, lower alkanoyl, lower alkoxycarbonyl, a group of formula: —$Q^p$—$Ar^{2p}$, and an optionally protected, lower alkylene optionally substituted with oxo, hydroxy(lower) alkyl or carboxyl group;

$Ar^{2p}$ represents an aryl or heteroaryl which may be substituted, the substituent being selected from the group consisting of halogen, cyano, lower alkyl, halo (lower)alkyl, lower alkoxy, halo(lower)alkoxy, di-lower alkylamino, lower alkanoyl, aryl, and an optionally protected, hydroxy(lower)alkyl, hydroxy or lower alkyl amino group;

$Ar^3$ represents a phenyl which may be substituted by halogen or nitro;

$Q^p$ represents a single bond or optionally protected carbonyl;

with a compound of formula (III):

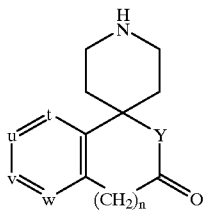

(III)

wherein n represents 0 or 1;
t, u, v and w each independently represent a nitrogen atom or a methine group which may have a substituent selected from the group consisting of halogen, lower alkyl, lower alkoxy and optionally protected hydroxy, wherein at least two of which represent said methine group;
Y represents an imino which may be substituted with a lower alkyl, or oxygen atom;
to provide a compound of formula (IV-1):

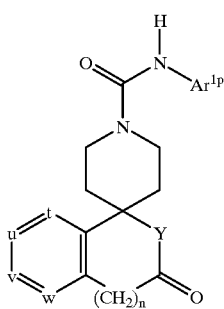

(IV-1)

wherein Ar$^{1p}$, n, t, u, v, w and Y have the same meaning as described above;
optionally followed by elimination of a protecting group.

17. Neuropeptide Y receptor antagonist which comprises a compound of the general formula (I):

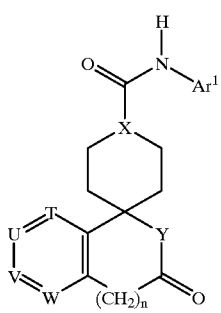

(I)

wherein Ar$^1$ represents an aryl or heteroaryl which may be substituted, the substituent being selected from the group consisting of halogen, nitro, lower alkyl, halo (lower)alkyl, hydroxy(lower)alkyl, cyclo(lower)alkyl, lower alkenyl, lower alkoxy, halo(lower)alkoxy, lower alkylthio, carboxyl, lower alkanoyl, lower alkoxycarbonyl, lower alkylene optionally substituted with oxo, and a group represented by formula of —Q—Ar$^2$;

Ar$^2$ represents an aryl or heteroaryl which may be substituted, the substituent being selected from the group consisting of halogen, cyano, lower alkyl, halo (lower)alkyl, hydroxy(lower)alkyl, hydroxy, lower alkoxy, halo(lower)alkoxy, lower alkylamino, di-lower alkylamino, lower alkanoyl and aryl;
n represents 0 or 1;
Q represents a single bond or carbonyl;
T, U, V and W each independently represent a nitrogen atom or a methine group which may have a substituent selected from the group consisting of halogen, with a lower alkyl, hydroxy and lower alkoxy, wherein at least two of which represent said methine group;
X represents nitrogen;
Y represents an imino which may be substituted with lower alkyl, or oxygen; and
a salt or ester thereof.

18. A method of the treatment of bulimia, obesity or diabetes, which comprises administering a therapeutically effective amount of a compound of the formula (I):

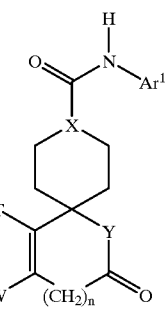

(I)

wherein Ar$^1$ represents an aryl or heteroaryl which may be substituted, the substituent being selected from the group consisting of halogen, nitro, lower alkyl, halo (lower)alkyl, hydroxy(lower)alkyl, cyclo(lower)alkyl, lower alkenyl, lower alkoxy, halo(lower)alkoxy, lower alkylthio, carboxyl, lower alkanoyl, lower alkoxycarbonyl, lower alkylene optionally substituted with oxo, and a group represented by formula of —Q—Ar$^2$;

Ar$^2$ represents an aryl or heteroaryl which may be substituted, the substituent being selected from the group consisting of halogen, cyano, lower alkyl, halo (lower)alkyl, hydroxy(lower)alkyl, hydroxy, lower alkoxy, halo(lower)alkoxy, lower alkylamino, di-lower alkylamino, lower alkanoyl and aryl;
n represents 0 or 1;
Q represents a single bond or carbonyl;
T, U, V and W each independently represent a nitrogen atom or a methine group which may have a substituent selected from the group consisting of halogen, lower alkyl, hydroxy or lower alkoxy, wherein at least two of which represent said methine group;
X represents nitrogen;
Y represents an imino which may be substituted with a lower alkyl, or oxygen; or
a salt or ester thereof.

19. A pharmaceutical composition for the treatment of bulimia, obesity or diabetes which comprises a pharmaceutically effective amount of a compound of claim 1 together with a pharmaceutically acceptable additive.

* * * * *